US011691992B2

(12) United States Patent
Jacobs et al.

(10) Patent No.: US 11,691,992 B2
(45) Date of Patent: *Jul. 4, 2023

(54) OXABOROLE ANALOGS AND USES THEREOF

(71) Applicants:Anacor Pharmaceuticals, Inc., New York, NY (US); The Government of the United States, as represented by the Secretary of the Army, Fort Detrick, MD (US)

(72) Inventors: Robert Toms Jacobs, Wake Forest, NC (US); Yang Liu, Foster City, CA (US); Richard J. Sciotti, Olney, MD (US); Jason D. Speake, Durham, NC (US); Gavin Alistair Whitlock, Canterbury (GB); Paul Alan Glossop, Canterbury (GB); Charles Eric Mowbray, Nyon (CH); Delphine Françoise Monique Launay, Ornex (FR); Stephen John Robinson, Geneva (CH)

(73) Assignees: Anacor Pharmaceuticals, Inc., New York, NY (US); The Government of the United States, as represented by the Secretary of the Army, Fort Detrick, MD (US)

(*) Notice: Subject to any disclaimer, the term of this patent is extended or adjusted under 35 U.S.C. 154(b) by 34 days.

This patent is subject to a terminal disclaimer.

(21) Appl. No.: 17/173,884

(22) Filed: Feb. 11, 2021

(65) Prior Publication Data
US 2021/0253605 A1    Aug. 19, 2021

Related U.S. Application Data

(63) Continuation of application No. 16/489,824, filed as application No. PCT/US2018/020464 on Mar. 1, 2018, now Pat. No. 10,961,261.

(60) Provisional application No. 62/465,294, filed on Mar. 1, 2017.

(51) Int. Cl.
*C07F 5/02* (2006.01)
*A61P 33/02* (2006.01)

(52) U.S. Cl.
CPC .............. *C07F 5/025* (2013.01); *A61P 33/02* (2018.01)

(58) Field of Classification Search
None
See application file for complete search history.

(56) References Cited

U.S. PATENT DOCUMENTS

| | | | |
|---|---|---|---|
| 10,961,261 B2 | 3/2021 | Jacobs et al. | |
| 2011/0065725 A1 | 3/2011 | Garzya et al. | |
| 2015/0344471 A1 | 12/2015 | Chatterjee et al. | |
| 2015/0361104 A1 | 12/2015 | Akama et al. | |
| 2020/0024289 A1 | 1/2020 | Jacobs et al. | |

FOREIGN PATENT DOCUMENTS

| | | |
|---|---|---|
| WO | WO-2004/056322 A2 | 7/2004 |
| WO | WO-2005/013892 A2 | 2/2005 |
| WO | WO-2005/123094 A2 | 12/2005 |
| WO | WO-2006/085932 A2 | 8/2006 |
| WO | WO-2007/095638 A2 | 8/2007 |
| WO | WO-2007/131072 A2 | 11/2007 |
| WO | WO-2007/146965 A2 | 12/2007 |
| WO | WO-2008/157726 A1 | 12/2008 |
| WO | WO-2009/111676 A2 | 9/2009 |
| WO | WO-2009/140309 A2 | 11/2009 |
| WO | WO-2010/027975 A1 | 3/2010 |
| WO | WO-2010/045503 A1 | 4/2010 |
| WO | WO-2010/045505 A1 | 4/2010 |
| WO | WO-2010/080558 A1 | 7/2010 |
| WO | WO-2011/017125 A1 | 2/2011 |
| WO | WO-2011/019618 A1 | 2/2011 |
| WO | WO-2011/022337 A1 | 2/2011 |
| WO | WO-2011/037731 A1 | 3/2011 |
| WO | WO-2011/049971 A1 | 4/2011 |
| WO | WO-2011/060196 A1 | 5/2011 |
| WO | WO-2011/094450 A1 | 8/2011 |
| WO | WO-2011/116348 A1 | 9/2011 |
| WO | WO-2012/033858 A2 | 3/2012 |
| WO | WO-2012/145734 A1 | 10/2012 |
| WO | WO-2013/078070 A1 | 5/2013 |
| WO | WO-2013/078071 A1 | 5/2013 |
| WO | WO-2014/121124 A1 | 8/2014 |
| WO | WO-2015/013318 A1 | 1/2015 |
| WO | WO-2018/160845 A1 | 9/2018 |

OTHER PUBLICATIONS

Akama, T., et al.. Discovery and structure-activity relationships of 6-(benzoylamino) benzoxaboroles as orally active anti-inflammatory agents. Bioorganic & medicinal chemistry letters, 23(21):5870-5873 (2013).
Baltz, T. et al., Cultivation in a semi-defined medium of animal infective forms of Trypanosoma brucei, T. equiperdum, T. evansi, T. rhodesiense and T. gambiense, EMBO J., 4(5):1273-1277 (1985).
Brun, R., et al., Development of novel drugs for human African trypanosomiasis, Future Microbiology, 6(6):677-691 (2011).
Buckner, F. et al., Efficient technique for screening drugs for activity against Trypanosoma cruzi using parasites expressing beta-galactosidase, Antimicrob Agents Chemother, 40(11):2592-2597 (1996).
Buckner, F.S, and Wilson, A.J., Colorimetric assay for screening compounds against Leishmania amastigotes grown in macrophages, Am J Trap Med Hyg., 72(5):600-605 (2005).
Ding, D., et al., Design, synthesis, and structure—activity relationship of Trypanosoma brucei leucyl-tRNA synthetase inhibitors as antitrypanosomal agents, Journal of medicinal chemistry, 54(5):1276-1287 (2011).

(Continued)

*Primary Examiner* — Po-Chih Chen
(74) *Attorney, Agent, or Firm* — Matthew J. Pugmire

(57) ABSTRACT

This application describes compounds, compositions, and methods which are useful in treating, preventing, inhibiting, ameliorating, or eradicating the pathology and/or symptomology of a disease caused by a parasite.

20 Claims, 3 Drawing Sheets

(56) References Cited

OTHER PUBLICATIONS

Haberland, A. et al., Chronic Chagas disease: from basics to laboratory medicine, Clin Chem Lab Med, 51(2):271-294 (2013).

Hussain, H. et al., Fruitful Decade for Antileishmanial Compounds from 2002 to Late 2011, Chem Reviews, 114(20):10369-428 (20141).

International Search Report for PCT/US2018/20464 (Novel Oxaborole Analogs and Uses Thereof, filed Mar. 1, 2008), issued by ISA/US, 2 pages (dated Apr. 24, 2018).

Jacobs, R. et al., SCYX-7158, an Orally-Active Benzoxaborole for the Treatment of Stage 2 Human African Trypanosomiasis, PLoS Negl Trop Dis, 5(6):e1151 (2011).

Jacobs, R et al., Benzoxaboroles: a new class of potential drugs for human African trypanosomiasis, Future Med Chem., 3(10):1259-1278 (2011).

Jacobs, R. et al., Boron-based drugs as antiprotozoals, Current opinion in infectious diseases, 24(6):586-592 (2011).

Kaiser, M. et al., Repurposing of the Open Access Malaria Box for Kinetoplastid Diseases Identifies Novel Active Scaffolds against Trypanosomatids, J Biomol Screen, 20(5):634-645 (2015).

Li, X., et al., Synthesis and SAR of acyclic HCV NS3 protease inhibitors with novel P4-benzoxaborole moieties, Bioorganic & medicinal chemistry letters, 21(7):2048-2054 (2011).

Sharlow, E. et al., Identification of potent chemotypes targeting Leishmania major using a high-throughput, low-stringency, computationally enhanced, small molecule screen, PLoS Negl Trap Dis., 3(11):e540 (2009).

Thuita, J. et al., Efficacy of the diamidine DB75 and its prodrug DB289, against murine models of human African trypanosomiasis, Acta Trop., 108(1):6-10 (2008).

Written Opinion for PCT/US2018/20464 (Novel Oxaborole Analogs and Uses Thereof, filed Mar. 1, 2008), issued by ISA/US, 7 pages (dated Apr. 24, 2018).

Wu, P., et al., Novel pyrrolobenzoxaboroles: Design, synthesis, and biological evaluation against Trypanosoma brucei, European journal of medicinal chemistry, 81:59-75 (2014).

Zhang, Y. et al., Benzoxaborole antimalarial agents. Part 4. Discovery of potent 6-(2-(alkoxycarbonyl) pyrazinyl-5-oxy)-1, 3-dihydro-1-hydroxy-2, 1-benzoxaboroles, Journal of medicinal chemistry, 58(13):5344-5354 (2015).

OXABOROLE ANALOGS AND USES THEREOF

CROSS REFERENCE TO RELATED APPLICATIONS

This application is a continuation application of U.S. patent application Ser. No. 16/489,824, filed on Aug. 29, 2019, which is the national phase entry of PCT App. No. PCT/US18/20464, filed Mar. 1, 2018, which claims priority to U.S. provisional application Ser. No. 62/465,294, filed on Mar. 1, 2017, the entirety of each of which is hereby incorporated by reference.

GOVERNMENT SUPPORT

This invention was made with government support under grant number W81XWH-14-2-0171 awarded by the United States Army Medical Research and Materiel Command. The government has certain rights in the invention.

BACKGROUND OF THE INVENTION

The most widely distributed kinetoplastid order are the *Leishmania*, which infect individuals in sub-tropical climates around the globe, including Asia, the Middle East, Africa, southern Europe, Central and South America. Diseases caused by *Leishmania* species range from relatively mild and ultimately self-resolving cutaneous leishmaniasis, through disfiguring mucocutaneous leishmaniasis to the potentially fatal visceral leishmaniasis. Since 2005, cutaneous leishmaniasis has been identified as a problem for military forces participating in conflicts in Afghanistan and Iraq. Mucocutaneous leishmaniasis is widely distributed in both southern Europe and the Americas, and represents a significant health problem, particularly in children. The most serious disease caused by *Leishmania* parasites, visceral leishmaniasis (VL), is most prevalent in India and eastern Africa, and significant mortality continues to be an issue in these areas.

Global incidence of symptomatic leishmaniasis is estimated at 2 million cases per year and is rapidly increasing, making leishmaniasis a top priority for the tropical disease program of the World Health Organization. Of the 2 million new cases of leishmaniasis that occur each year, approximately three-quarters are cases of cutaneous leishmaniasis (CL). Although CL does not result in death; the true socioeconomic impact of cutaneous leishmaniasis is difficult to quantify. Severe disfigurement, disability, and social/psychological stigma often results from CL infections.

Prevention of CL and VL is limited to personal protective measures such as insect repellent, bed nets, and control of disease reservoirs such as rodents and dogs; no chemoprophylactic or vaccine options are available. Treatment options for CL and VL are similarly limited. The drugs traditionally used to treat leishmaniasis, such as pentavalent antimony, pentamidine, and amphotericin B, have variable efficacy, due in part to resistance, and occasionally produce severe side effects. Newer agents such as nitroimidazoles, miltefosine, paromomycin (injectable and topical), and liposomal amphotericin B are either difficult to use or expensive.

Chagas disease, caused by the parasite *Trypanosoma cruzi*, is widely distributed across Central and South America, and is considered the leading infectious cause of cardiomyopathy and death due to parasitic infection in the western hemisphere. It is estimated that over 7 million individuals are infected with *T. cruzi* parasites, and over 100 million are at risk. The estimated global burden of the disease is 649,000 disability adjusted life years (the number of healthy years of life lost due to premature death and disability). Causing about 14,000 deaths annually, Chagas disease kills more people in Latin America than any other parasitic disease, including malaria. With continued global warming, northward expansion of *T. cruzi* infections into the United States has been observed. A particular challenge of Chagas disease is that the acute symptoms are relatively minor, such that the majority of patients are undiagnosed for decades; only 30% of chronically infected individuals will develop cardiovascular disease.

Trypanosomatids are a group of kinetoplastid protozoa distinguished by having only a single flagellum. Trypanosomatids are responsible for diseases such as South American trypanosomiasis (Chagas Disease) and African Animal Trypanosomosis (AAT).

*T. cruzi* is transmitted by various insect vectors that belong to the Reduviidae family. Transmission to humans is dependent on living conditions as these insects inhabit houses of mud and thatch which are common in lower socioeconomic areas. Infection may also be acquired by consuming contaminated food, congenitally, or via blood transfusion or organ transplantation. The acute phase of *T. cruzi* infection is generally controlled by the emerging immune response and is mild or asymptomatic and thus often undetected. However, the vast majority of infected individuals fail to clear the infection and thus remain chronically infected; 30-40% of these will eventually develop life-threatening heart or gastrointestinal disease. Chronic Chagas remains an incurable disease that causes long term severe disability or death in approximately one-third of infected individuals. In addition, disability caused by chronic Chagas disease has a great social and economic impact, including unemployment and decreased earning ability. In Brazil alone, losses of over US $1.3 billion in wages and industrial productivity were due to workers with Chagas disease. In addition to the loss in productivity, the medical costs to treat infected individuals who develop severe cardiac or chronic digestive problems are high.

It has long been established that *T. cruzi* can infect dogs, particularly those who are housed outdoors in the southern US, Central, and South America. A recent study in Texas suggested that shelter dogs serve as a good sentinel for all dogs, and found that 9% of shelter dogs evaluated across Texas harbored *T. cruzi*. In Texas, *T. cruzi* infection in dogs is considered a "notifiable condition"—any dog found to be harboring the parasite must be reported to the Texas Department of State Health Services. As there is no approved treatment for Chagas disease in dogs, animals may be euthanized.

Novel chemical entities with novel mechanisms of action are urgently needed to combat these diseases.

SUMMARY OF THE INVENTION

In certain embodiments, the present invention provides a compound of formula I:

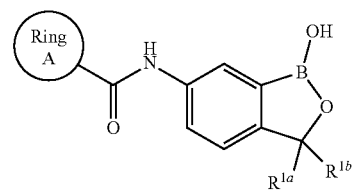

DETAILED DESCRIPTION OF CERTAIN EMBODIMENTS

In some embodiments, the present invention provides a compound of formula I:

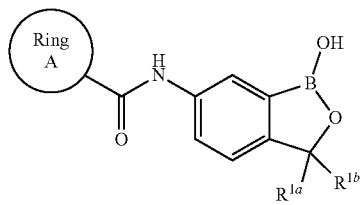

or a pharmaceutically acceptable salt thereof, wherein:
$R^{1a}$ and $R^{1b}$ are independently selected from hydrogen and optionally substituted $C_{1-6}$ aliphatic; wherein $R^{1a}$ and $R^{1b}$ are optionally taken together to form an optionally substituted 3- to 6-membered carbocyclic ring;
Ring A is triazolyl substituted with an $R^2$ group and an $R^3$ group;
$R^2$ is hydrogen or an optionally substituted group selected from $C_{1-6}$ aliphatic and 3- to 6-membered carbocyclyl;
$R^3$ is an optionally substituted group selected from phenyl, $C_{1-6}$ aliphatic, 3- to 8-membered carbocyclyl, and 5- to 6-membered heteroaryl containing 1-3 heteroatoms independently selected from nitrogen, oxygen, and sulfur.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocyclyl," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocyclyl" or "cycloalkyl") refers to a monocyclic $C_3$-$C_7$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl, or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In some embodiments, an 8-10 membered bicyclic aryl group is an optionally substituted naphthyl ring. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocyclyl," "heterocyclic radical," and "heterocyclic ring" are used interchangeably and refer to a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in this context in reference to a ring atom, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}$NR (as in A-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•$$_2$, —NO$_2$, —SiR$^•$$_3$, —OSiR$^•$$_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6- membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. The term "pharmaceutically acceptable salt" is understood in the context of the provided boron-containing compounds to comprise chemical species resulting from the addition of two or more distinct molecules to form a single chemical entity, including Lewis adducts and hydrates thereof.

In certain embodiments, the neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

In some embodiments, a pharmaceutically acceptable salt comprises a compound of formula I and arginine. In some embodiments, a pharmaceutically acceptable salt comprises a compound of formula II and arginine. In some embodiments, a pharmaceutically acceptable salt comprises a compound of formula III (e.g., compound I-84) and arginine. In some embodiments, a pharmaceutically acceptable salt comprises a compound of formula III (e.g., compound I-84), arginine, and water. In some embodiments, a pharmaceutically acceptable salt may be hydrated. In some embodiments, a pharmaceutically acceptable salt may be a monohydrate. In some embodiments, a pharmaceutically acceptable salt may be anhydrous.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention.

Such compounds are useful, for example, as analytical tools, as probes in biological assays, or as therapeutic agents in accordance with the present invention.

The symbol "⁓", except when used as a bond to depict unknown or mixed stereochemistry, denotes the point of attachment of a chemical moiety to the remainder of a molecule or chemical formula.

Compounds

As described above, in certain embodiments provided compounds are of formula I:

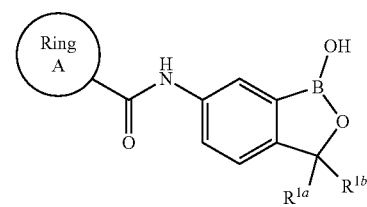

I or a pharmaceutically acceptable salt thereof, wherein each of R$^{1a}$, R$^{1b}$, and Ring A is as defined above and described in classes and subclasses herein, both singly and in combination.

As used herein, unless otherwise stated, references to formula I also include all subgenera of formula I defined and described herein (e.g., formulae II, III, IV, V, VI, VII, VIII, IX, and X).

In some embodiments, R$^{1a}$ and R$^{1b}$ are hydrogen.

In some embodiments, R$^{1a}$ and R$^{1b}$ are each independently C$_{1-6}$ aliphatic. In some embodiments, R$^{1a}$ and R$^{1b}$ are methyl.

In some embodiments, R$^{1a}$ and R$^{1b}$ are taken together with the carbon atom to which they are attached to form an optionally substituted 3- to 6-membered spiro carbocyclic ring. In some embodiments, R$^{1a}$ and R$^{1b}$ are taken together with the carbon atom to which they are attached to form a 6-membered spiro carbocyclic ring. In some embodiments, $R^{1a}$ and $R^{1b}$ are taken together with the carbon atom to which they are attached to form a 5-membered spiro carbocyclic ring. In some embodiments, $R^{1a}$ and $R^{1b}$ are taken together with the carbon atom to which they are attached to form a 4-membered spiro carbocyclic ring. In some embodiments, $R^{1a}$ and $R^{1b}$ are taken together with the carbon atom to which they are attached to form a 3-membered spiro carbocyclic ring.

In some embodiments, Ring A is triazolyl substituted with an $R^2$ group and an $R^3$ group. In some embodiments, Ring A is selected from the group consisting of:

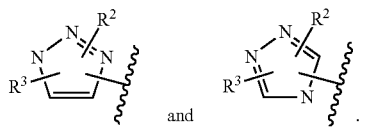

and

It will be appreciated that when a triazolyl group is drawn in a particular fashion herein, all resonance or tautomeric forms are contemplated and encompassed by the present disclosure. In addition, it will be understood that where a triazolyl group is depicted having a nitrogen without complete valency (e.g., 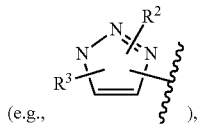 ), the nitrogen is intended to be substituted with one of the depicted substituent or attachment groups.

In some embodiments, Ring A is selected from the group consisting of:

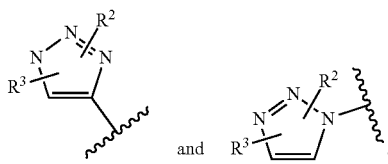

and

In some embodiments, Ring A is:

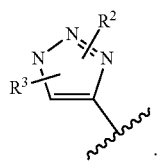

In some embodiments, Ring A is:

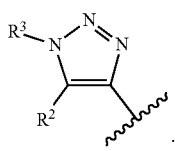

In some embodiments, Ring A is:

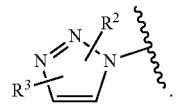

In some embodiments, Ring A is selected from the group consisting of:

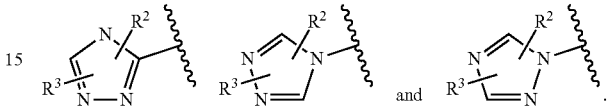

and

In some embodiments, Ring A is:

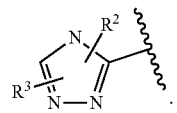

In some embodiments, $R^2$ is hydrogen or an optionally substituted group selected from $C_{1-6}$ aliphatic and 3-6 membered carbocyclyl.

In some embodiments, $R^2$ is hydrogen.

In some embodiments, $R^2$ is optionally substituted $C_{1-6}$ aliphatic. In some embodiments, $R^2$ is optionally substituted $C_{1-3}$ aliphatic. In some embodiments, $R^2$ is methyl, ethyl, n-propyl, or i-propyl. In some embodiments, $R^2$ is methyl.

In some embodiments, $R^2$ is $C_{1-6}$ aliphatic optionally substituted with halo, methoxy, or hydroxyl. In some embodiments, $R^2$ is $C_{1-3}$ aliphatic optionally substituted with halo, methoxy, or hydroxyl. In some embodiments, $R^2$ is trifluoromethyl or an optionally substituted group selected from methyl, ethyl, n-propyl, i-propyl, or cyclopropyl.

In some embodiments, $R^2$ is $C_{1-6}$ aliphatic optionally substituted with fluoro. In some embodiments, $R^2$ is $C_{1-3}$ aliphatic optionally substituted with fluoro. In some embodiments, $R^2$ is trifluoromethyl. In some embodiments, $R^2$ is optionally substituted 3-membered carbocyclyl. In some embodiments, $R^2$ is cyclopropyl.

In some embodiments, $R^3$ is optionally substituted 3- to 8-membered carbocyclyl. In some embodiments, $R^3$ is optionally substituted cyclopropyl. In some embodiments, $R^3$ is optionally substituted cyclobutyl. In some embodiments, $R^3$ is optionally substituted cyclopentyl. In some embodiments, $R^3$ is optionally substituted cyclohexyl. In some embodiments, $R^3$ is optionally substituted cycloheptyl. In some embodiments, $R^3$ is optionally substituted cyclooctyl.

In some embodiments, $R^3$ is optionally substituted $C_{1-6}$ aliphatic. In some embodiments, $R^3$ is optionally substituted methyl. In some embodiments, $R^3$ is optionally substituted ethyl. In some embodiments, $R^3$ is optionally substituted propyl. In some embodiments, $R^3$ is optionally substituted butyl. In some embodiments, $R^3$ is optionally substituted pentyl. In some embodiments, $R^3$ is optionally substituted hexyl.

In some embodiments, $R^3$ is optionally substituted phenyl or 5-6 membered heteroaryl containing 1-3 heteroatoms independently selected from nitrogen, oxygen, and sulfur.

In some embodiments, $R^3$ is optionally substituted phenyl. In some embodiments, $R^3$ is phenyl.

In some embodiments, $R^3$ is optionally substituted 5-6 membered heteroaryl containing 1-3 heteroatoms independently selected from nitrogen, oxygen, and sulfur. In some embodiments, $R^3$ is optionally substituted 5-6 membered heteroaryl containing 1-3 nitrogen atoms. In some embodiments, $R^3$ is optionally substituted pyridyl. In some embodiments, $R^3$ is

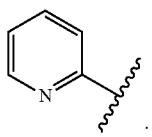

In some embodiments, provided compounds are of formula II:

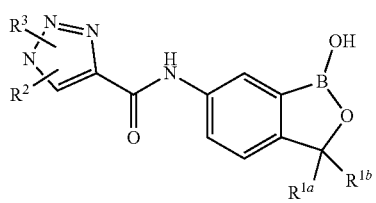

II or a pharmaceutically acceptable salt thereof, wherein each of $R^{1a}$, $R^{1b}$, $R^2$, and $R^3$ is as defined above and described in classes and subclasses herein, both singly and in combination.

In some embodiments, provided compounds are of formula III:

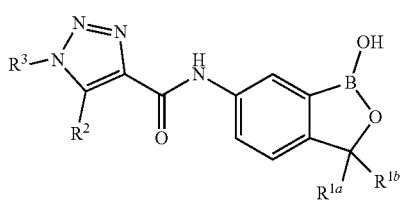

III or a pharmaceutically acceptable salt thereof, wherein each of $R^{1a}$, $R^{1b}$, $R^2$, and $R^3$ is as defined above and described in classes and subclasses herein, both singly and in combination.

In some embodiments, provided compounds are of formula IV:

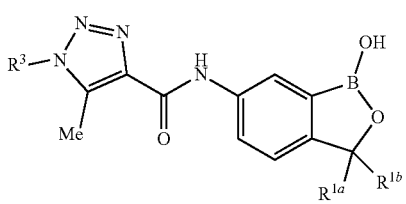

IV or a pharmaceutically acceptable salt thereof, wherein each of $R^{1a}$, $R^{1b}$, and $R^3$ is as defined above and described in classes and subclasses herein, both singly and in combination.

In some embodiments, provided compounds are of formula V:

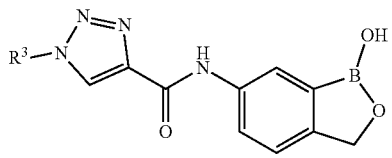

V or a pharmaceutically acceptable salt thereof, wherein each of $R^2$ and $R^3$ is as defined above and described in classes and subclasses herein, both singly and in combination.

In some embodiments, provided compounds are of formula VI:

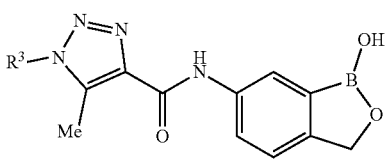

VI or a pharmaceutically acceptable salt thereof, wherein $R^3$ is as defined above and described in classes and subclasses herein, both singly and in combination.

In some embodiments, provided compounds are of formula VII:

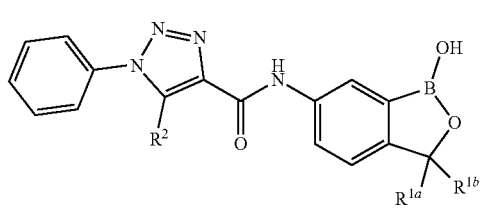

VII or a pharmaceutically acceptable salt thereof, wherein each of $R^{1a}$, $R^{1b}$, and $R^2$ is as defined above and described in classes and subclasses herein, both singly and in combination.

In some embodiments, provided compounds are of formula VIII:

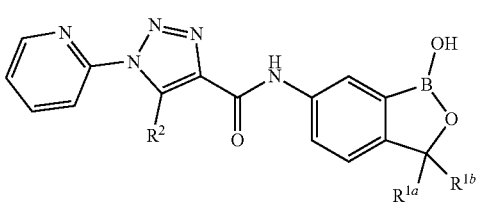

VIII or a pharmaceutically acceptable salt thereof, wherein each of $R^{1a}$, $R^{1b}$, and $R^2$ is as defined above and described in classes and subclasses herein, both singly and in combination.

In some embodiments, provided compounds are of formula IX:

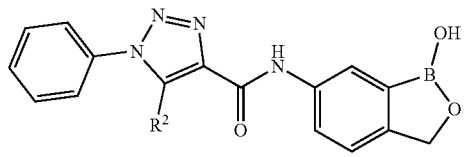

IX or a pharmaceutically acceptable salt thereof, wherein $R^2$ is as defined above and described in classes and subclasses herein, both singly and in combination.

In some embodiments, provided compounds are of formula X:

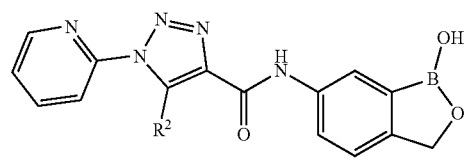

X or a pharmaceutically acceptable salt thereof, wherein $R^2$ is as defined above and described in classes and subclasses herein, both singly and in combination.

GENERAL METHODS OF PROVIDING COMPOUNDS

Figure 1A:
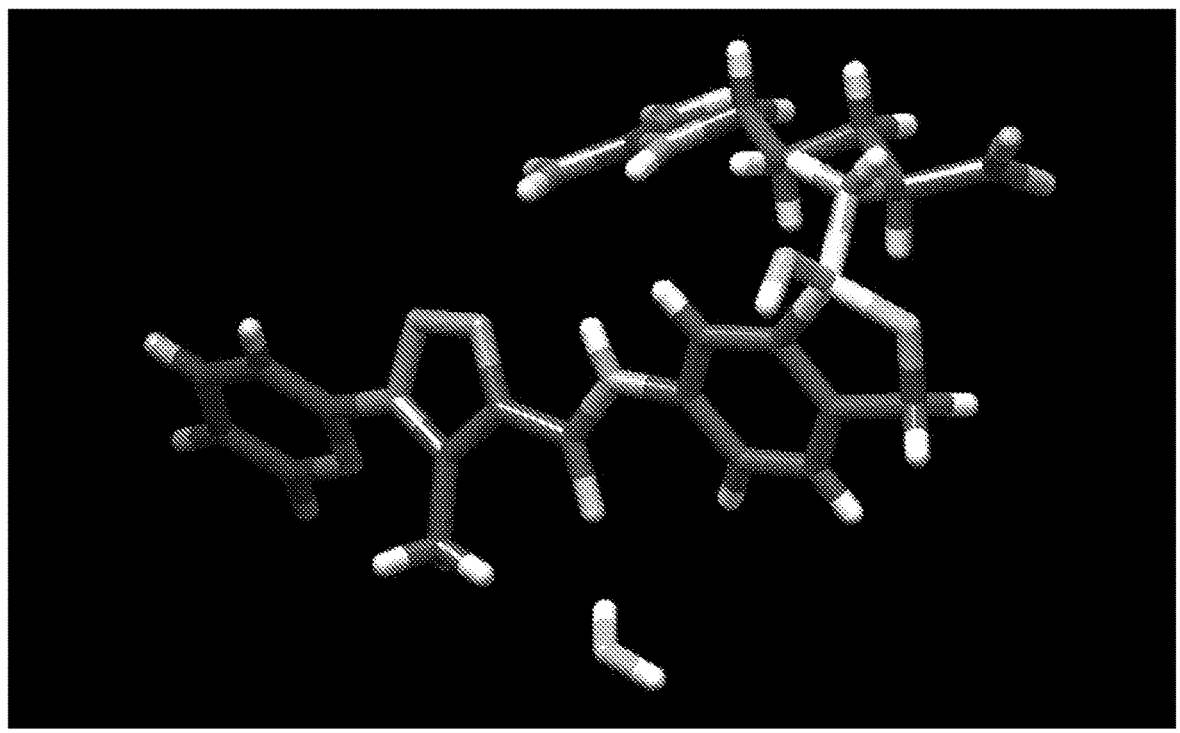
FIG. 1A and FIG. 1B each depict the crystal structure of N-(1-hydroxy-1,3-dihydrobenzo[c][1,2]oxaborol-6-yl)-5-methyl-1-(pyridin-2-yl)-1H-1,2,3-triazole-4-carboxamide arginine monohydrate (I-112).
Figure 1B:
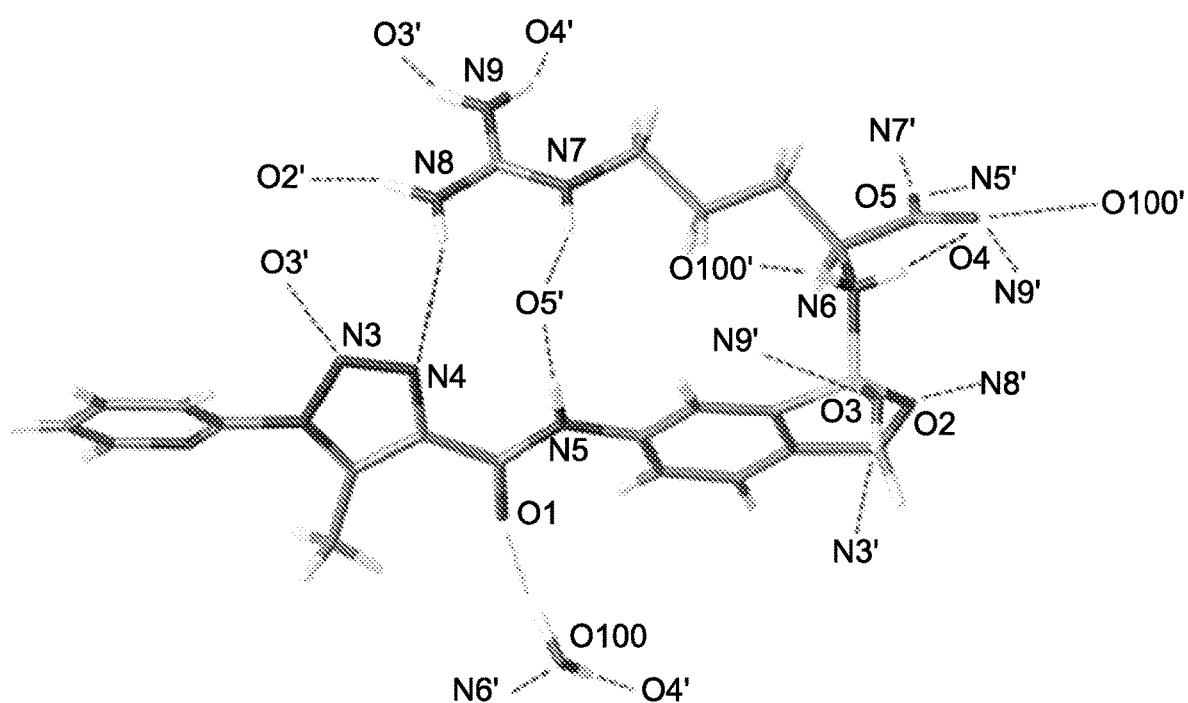
Figure 2:
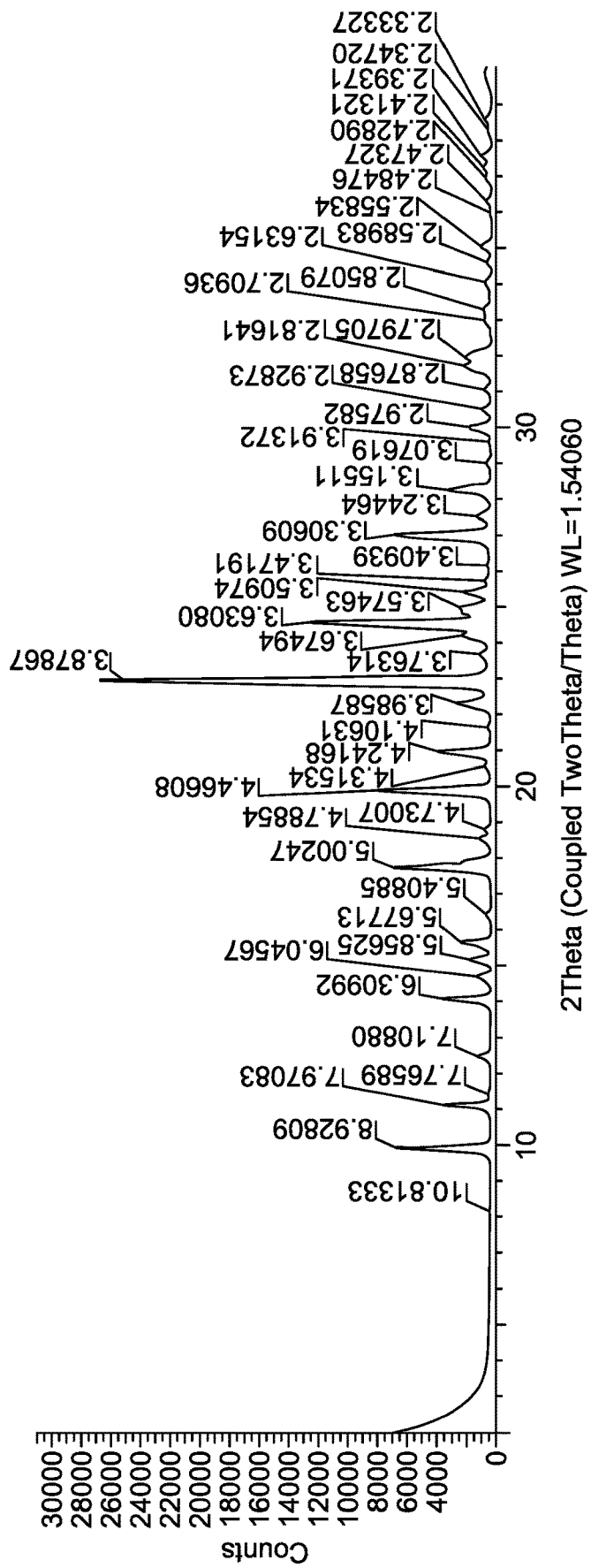
FIG. 2 depicts the XRPD spectrum of N-(1-hydroxy-1,3-dihydrobenzo[c][1,2]oxaborol-6-yl)-5-methyl-1-(pyridin-2-yl)-1H-1,2,3-triazole-4-carboxamide arginine monohydrate (I-112).
Figure 3:
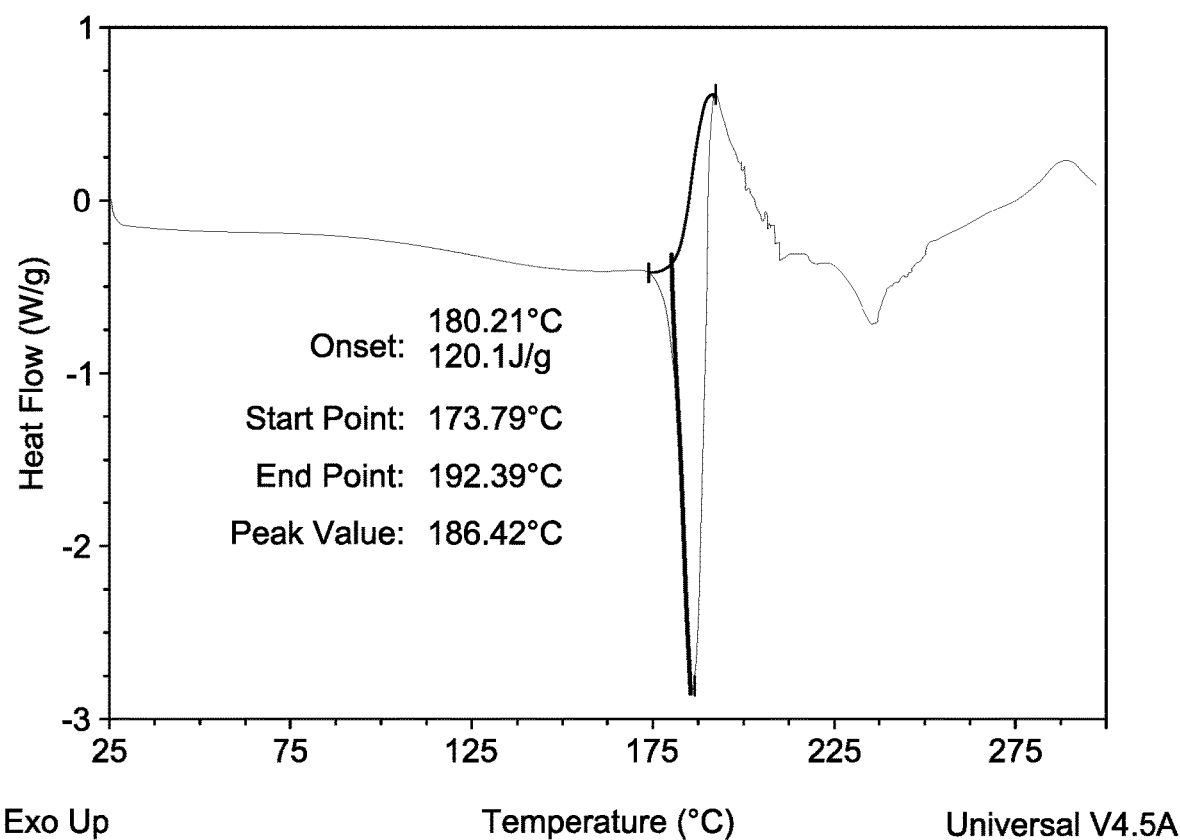
FIG. 3 depicts the differential scanning calorimetry (DSC) curve for N-(1-hydroxy-1,3-dihydrobenzo[c][1,2]oxaborol-6-yl)-5-methyl-1-(pyridin-2-yl)-1H-1,2,3-triazole-4-carboxamide arginine monohydrate (I-112).

Compounds of the present invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

In certain embodiments, certain compounds or intermediates are generally prepared according to Scheme A and General Methods 1-9 set forth below:

Scheme A

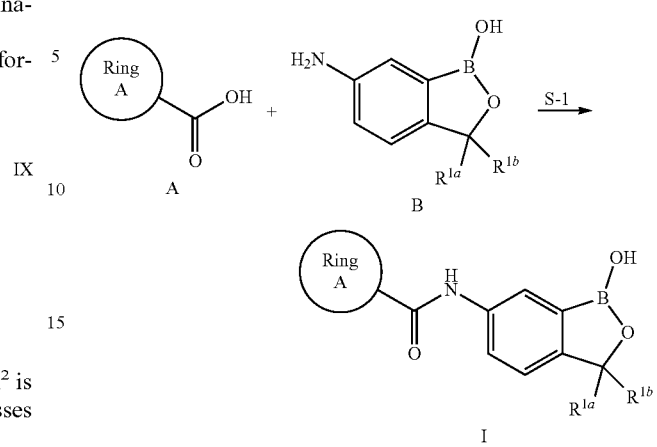

wherein each Ring A, $R^{1a}$, and $R^{1b}$ are defined and described in classes and subclasses herein. Syntheses of exemplary compounds A and B can be found below.

At Step S-1, compound A is coupled under suitable conditions with compound B to form compound I. In some embodiments, Step S-1 employs a suitable base. Such suitable bases and suitable conditions are known in the art. In some embodiments, a suitable base is an organic base. In some embodiments a suitable base is DIPEA. In some embodiments a suitable base is TEA. In some embodiments, Step S-1 employs a suitable coupling reagent. In some embodiments a suitable coupling reagent is HATU. In some embodiments, Step S-1 employs a suitable solvent. Such suitable solvents include, for example, polar aprotic solvents (i.e., THF, dioxane, DMF, DMSO, and combinations thereof). In some embodiments, a suitable solvent is DMF.

General Method 1: Synthesis of 1-aryl-[1H]-1,2,3-triazole-4-carboxylic acids

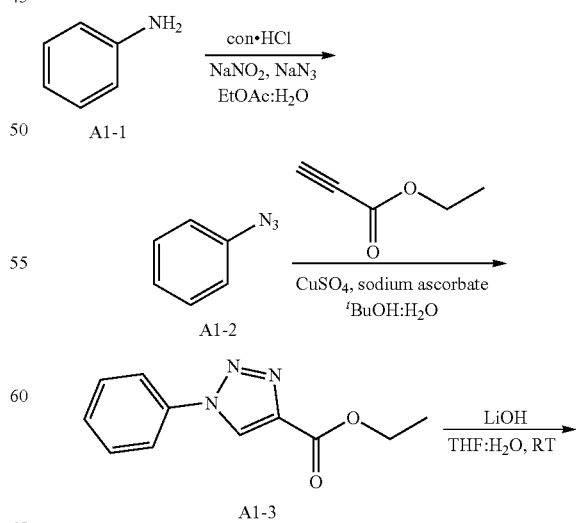

-continued
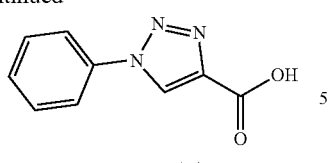
A1-4
General Method 2: Synthesis of 1-aryl-5-alkyl-[1H]-1,2,3-triazole-4-carboxylic acids
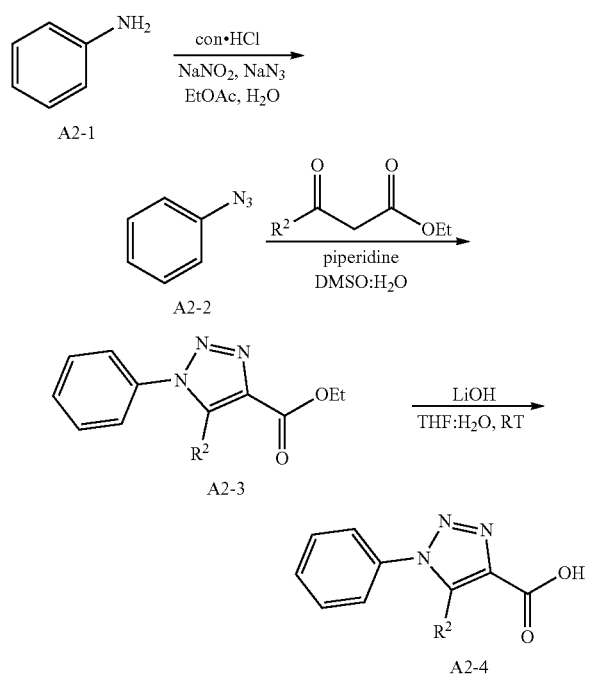
General Method 3: Synthesis of 1-substituted-5-alkyl-[1H]-1,2,3-triazole-4-carboxylic acids
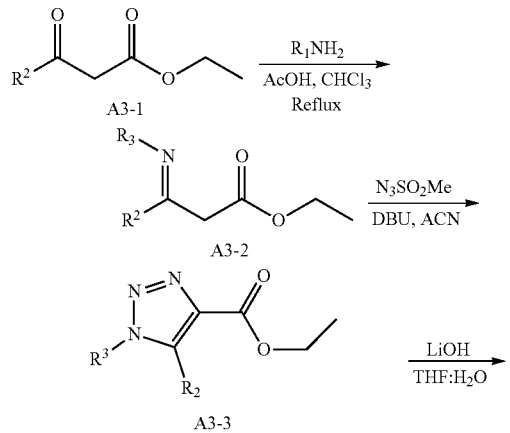
-continued
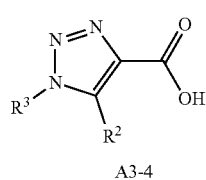
A3-4
General Method 4: Synthesis of 1-(2-pyridyl)-[1H]-1,2,3-triazole 4-carboxylic acids
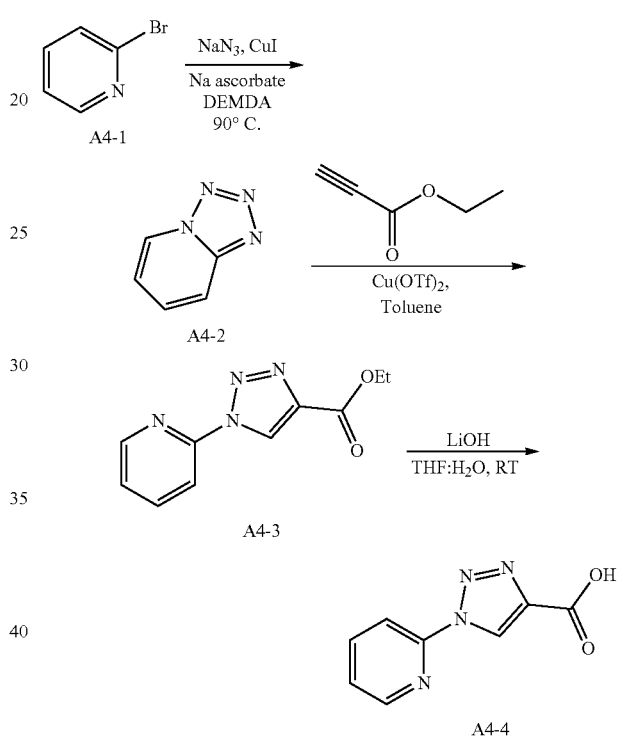
General Method 5: Synthesis of 1-(2-pyridyl)-5-methyl-[1H]-1,2,3-triazole-4-carboxylic acids
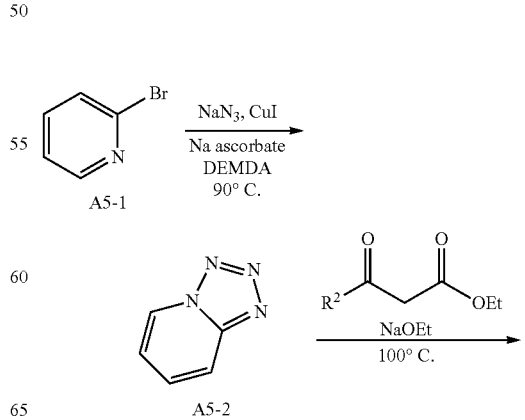

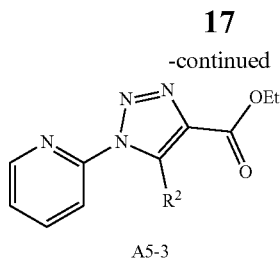
A5-3
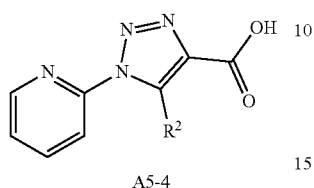
A5-4
General Method 6: Synthesis of 1-(3-pyridyl)-[1H]-1,2,3-triazole-4-carboxylic acids
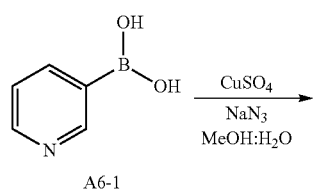
A6-1
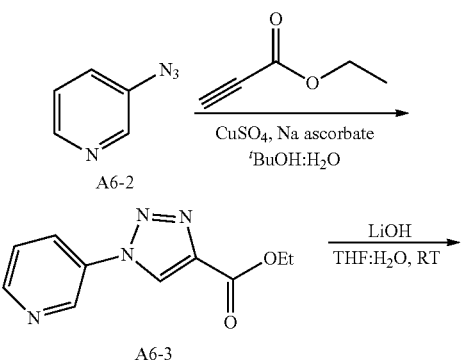
A6-3
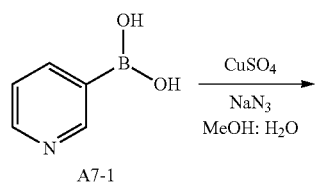
A6-4
General Method 7: Synthesis of 1-(3-pyridyl)-5-methyl-[1H]-1,2,3-triazole 4-carboxylic acids
A7-1
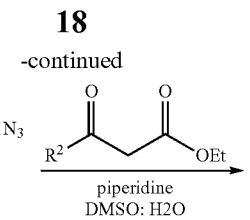
A7-2
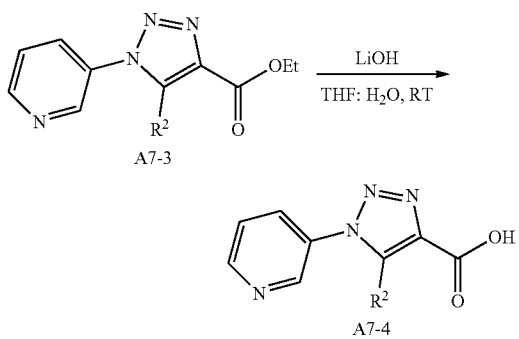
A7-3
A7-4
General Method 8: Synthesis of 1-methyl-5-(hetero)aryl-[1H]-1,2,4-triazole-3-carboxylic acids
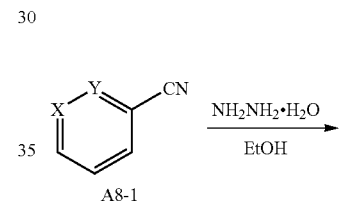
A8-1
A8-2
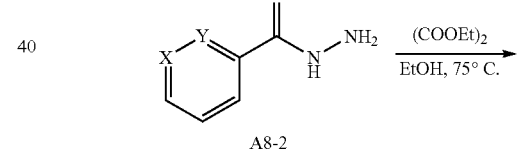
A8-3
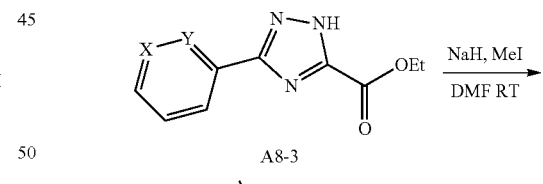
A8-4
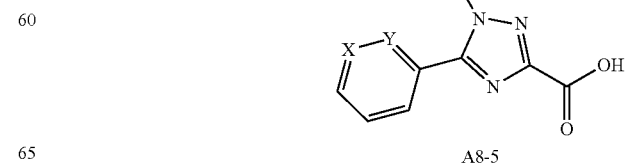
A8-5

General Method 9: Synthesis of 1-methyl-3-(hetero)aryl-[1H]-1,2,4-triazole-5-carboxylic acids

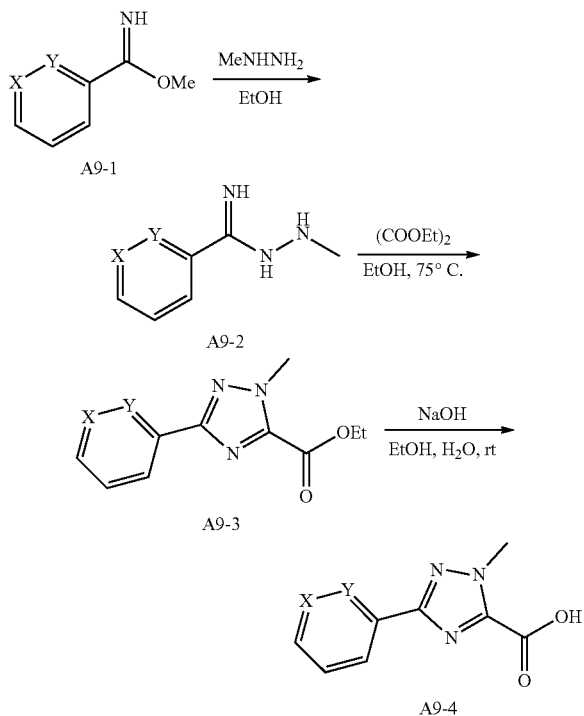

Methods of Use

In some embodiments, compounds of the present invention are useful in the treatment of parasitic infections. The term "parasitic infection" includes diseases or disorders involving parasites.

In some embodiments, compounds of the present invention are for use in medicine. In some embodiments, the compounds of the present invention are useful for treating a parasitic infection. In some embodiments, the compounds of the present invention are useful for treating, preventing, inhibiting, ameliorating, or eradicating the pathology and/or symptomology of a disease caused by a parasite. In some embodiments, the compounds of the present invention are useful for treating a parasitic infection associated with an organism belonging to Leishmania. In some embodiments, a parasitic infection is associated with L. major, L. donovani, L. mexicana, L. tropica, L. aethiopica, L. peruviana, L. guyanensis, L. braziliensis, L. infantum or combinations thereof. In some embodiments, a parasitic infection associated with a Leishmania species includes cutaneous, mucocutaneous, and visceral leishmaniasis. In some embodiments, a parasitic infection associated with Leishmania species includes cutaneous leishmaniasis. In some embodiments, a parasitic infection associated with Leishmania species includes mucocutaneous leishmaniasis. In some embodiments, a parasitic infection associated with Leishmania species includes visceral leishmaniasis. In some embodiments, the compounds of the present invention are useful for reducing the LDU of leishmaniasis in a host. In some embodiments, the compound of the present invention are useful in preventing and/or treating pathogen infections and/or a pathology associated with a pathogen infection. In certain embodiments, such pathogens are, or are associated with, a parasite as described herein.

The term "LDU" as used herein refers to Leishman-Donovan Unit, which is defined as multiplying the number of parasites per liver cell nucleus with the organ weight in milligrams. Methods for the determination of LDU are known in the art and defined in PCT publication number WO 2013/164359.

In some embodiments, compounds of the present invention are useful for treating a parasitic infection associated with L. major. In some embodiments, compounds of the present invention are useful for treating a parasitic infection associated with L. infantum. In some embodiments, compounds of the present invention are useful for treating a parasitic infection associated with L. donovani.

In some embodiments, compounds of the present invention are useful for treating a parasitic infection associated with an organism belonging to Trypanosoma such as T. cruzi, T. congolense, T. brucei, T. b. gambiense, and combinations thereof. In some embodiments, compounds of the present invention are useful for treating a parasitic infection associated with T. cruzi. In some embodiments, compounds of the present invention are useful for treating a parasitic infection associated with T. congolense. In some embodiments, compounds of the present invention are useful for treating a parasitic infection associated with T. brucei. In some embodiments, compounds of the present invention are useful for treating a parasitic infection associated with T. b. gambiense.

In certain embodiments, the present invention provides a method of treating a T. congolense-mediated disease or disorder in a subject comprising administering to a subject a provided compound. In some embodiments, the disease is trypanosomiasis. In some embodiments, the disease is African Animal Trypanosomosis (AAT).

In certain embodiments, the present invention provides a method of treating a T. vivix-mediated disease or disorder in a subject comprising administering to a subject a provided compound. In some embodiments, the disease is trypanosomiasis. In some embodiments, the disease is African Animal Trypanosomosis (AAT).

In some embodiments, the present invention provides a method of treating AAT comprising administering a provided compound to a subject suffering from AAT. In some embodiments, the subject suffering from AAT is a mammal. In some embodiments, the subject suffering from AAT is a cattle species. In some embodiments, the subject suffering from AAT a cow.

In certain embodiments, the present invention provides a method of treating a T. cruzi-mediated disease or disorder in a subject comprising administering to a subject a provided compound. In some embodiments, the disease is Chagas disease. In some embodiments, the present invention provides a method of treating Chagas disease comprising administering a provided compound to a subject suffering from Chagas disease. In some embodiments, the subject suffering from Chagas disease is a mammal. In some embodiments, the subject suffering from Chagas disease is a human. In some embodiments, the subject suffering from Chagas disease is a dog.

In some embodiments, the half maximal inhibitory concentration ($IC_{50}$) of the compound against a parasite is less than 1000 μM. In some embodiments, the $IC_{50}$ of the compound against a parasite is less than 500 μM In some embodiments, the $IC_{50}$ of the compound against a parasite is less than 100 μM. In some embodiments, the $IC_{50}$ of the compound against a parasite is less than 10 μM In some embodiments, the $IC_{50}$ of the compound against a parasite is less than 1 μM. In some embodiments, the $IC_{50}$ of the compound against a parasite is less than 0.1 μM. In some embodiments, the $IC_{50}$ of the compound against a parasite is less than 0.015 μM.

The term "treatment" (also "treat" or "treating"), as used herein, refers to any administration of a substance (e.g., pharmaceutical composition) that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder, and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The term "subject," as used herein, refers to a mammal/animal to whom a pharmaceutical composition is administered. In some embodiments, for any of the methods described herein, a subject is a mammal. In some embodiments, a mammal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In some embodiments, for any of the methods described herein, a mammal is a human.

Pharmaceutical Compositions

In another aspect, the present invention provides pharmaceutical compositions comprising a compound of formula I or a compound of formula I in combination with a pharmaceutically acceptable excipient (e.g., carrier).

The pharmaceutical compositions include optical isomers, diastereomers, or pharmaceutically acceptable salts of the inhibitors disclosed herein. The compound of formula I included in the pharmaceutical composition may be covalently attached to a carrier moiety, as described above. Alternatively, the compound of formula I included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethylcellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be coadministered to the subject. Coadministration is meant to include simultaneous or sequential administration of the compounds individually or in combination (more than one compound). The preparations can also be combined, when desired, with other active substances (e.g. to reduce metabolic degradation).

Combinations

The compounds of the invention may also be used in combination with additional therapeutic agents. The invention thus provides, in a further aspect, a combination comprising a compound described herein or a pharmaceutically acceptable salt thereof together with at least one additional therapeutic agent. In an exemplary embodiment, an additional therapeutic agent is a compound of the invention. In an exemplary embodiment, an additional therapeutic agent includes a boron atom.

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

Formulations

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In some embodiments, suitable carriers for parenteral administration will be selected for human administration. In some embodiments, suitable carriers for parenteral administration will be selected for veterinary administration. In particular, carriers for parenteral administration include aqueous solutions of dextrose, saline, pure water, ethanol, glycerol, glycerol formal, polyethylene glycol, propylene glycol, peanut oil, sesame oil, polyoxyethylene-block polymers, pyrrolidine, N-methyl pyrrolidione, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also be formulated as a food or drink supplement for humans.

Effective Dosage

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to a parasitic infection, such compositions will contain an amount of active ingredient effective to achieve the desired result.

The dosage and frequency (single or multiple doses) of compound administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of killing parasites and/or controlling their growth or reproduction as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring kinase inhibition and adjusting the dosage upwards or downwards, as described above. Therapeutically effective amounts for use in animals (e.g., cattle) may be determined from animal models (e.g., mouse models).

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

The following numbered embodiments, while non-limiting, are exemplary of certain aspects of the present disclosure:

1. A compound of formula I:

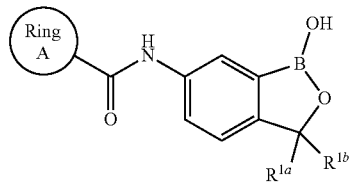

or a pharmaceutically acceptable salt thereof, wherein:
$R^{1a}$ is hydrogen or $C_{1-6}$-aliphatic;
$R^{1b}$ is hydrogen or $C_{1-6}$-aliphatic;
 wherein $R^{1a}$ and $R^{1b}$ are optionally taken together to form an optionally substituted 3- to 6-membered carbocyclic ring;
Ring A is triazolyl substituted with an $R^2$ group and an $R^3$ group;
$R^2$ is hydrogen or an optionally substituted group selected from $C_{1-6}$ aliphatic and 3-6 membered carbocyclyl;
$R^3$ is an optionally substituted group selected from phenyl, $C_{1-6}$ aliphatic, 3-8 membered carbocyclyl, and 5-6 membered heteroaryl containing 1-3 heteroatoms independently selected from nitrogen, oxygen, and sulfur.

2. The compound of embodiment 1, wherein Ring A is selected from:

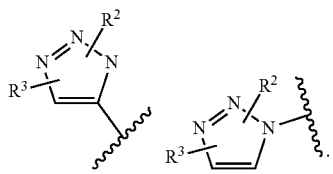

3. The compound of embodiment 1, wherein $R^{1a}$ is hydrogen or $C_{1-6}$-aliphatic and $R^{1b}$ is hydrogen or $C_{1-6}$-aliphatic.
4. The compound of embodiment 1, wherein $R^{1a}$ and $R^{1b}$ are taken together to form an optionally substituted 3- to 6-membered carbocyclic ring.
5. The compound of any one of the preceding embodiments, wherein $R^2$ is hydrogen.
6. The compound of any one of embodiments 1-4, wherein $R^2$ is an optionally substituted group selected from $C_{1-6}$ aliphatic and 3-6 membered carbocyclyl.
7. The compound of any one of the preceding embodiments, wherein $R^3$ is optionally substituted phenyl.
8. The compound of any one of embodiments 1-6, wherein $R^3$ is optionally substituted 5-6 membered heteroaryl containing 1-3 heteroatoms independently selected from nitrogen, oxygen, and sulfur.
9. The compound of embodiment 8, wherein $R^3$ is optionally substituted pyridyl.
10. The compound of any one of embodiments 1-9, wherein the compound is of formula II:

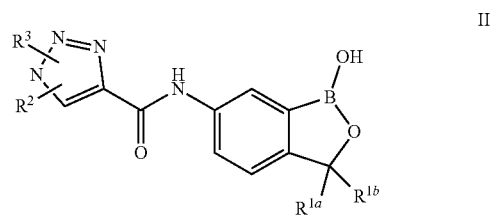

or a pharmaceutically acceptable salt thereof.
11. The compound of any one of embodiments 1-10, wherein the compound is of formula III:

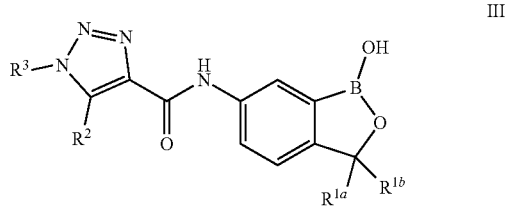

or a pharmaceutically acceptable salt thereof.
12. The compound of any one of embodiments 1-4 or 6-11, wherein the compound is of formula IV:

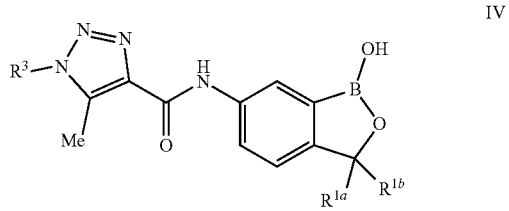

or a pharmaceutically acceptable salt thereof.
13. The compound of any one of embodiments 1-3 or 5-11, wherein the compound is of formula

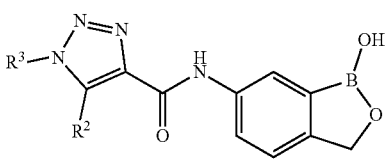

or a pharmaceutically acceptable salt thereof.
14. The compound of any one of embodiments 1-3 or 6-11, wherein the compound is of formula VI:

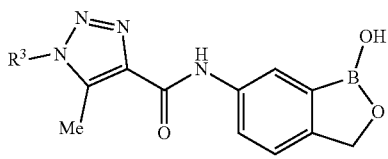

or a pharmaceutically acceptable salt thereof.
15. The compound of any one of embodiments 1-7 or 10-14, wherein the compound is of formula VII:

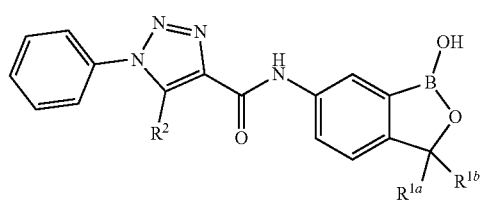

or a pharmaceutically acceptable salt thereof.
16. The compound of any one of embodiments 1-6 or 8-14, wherein the compound is of formula VIII:

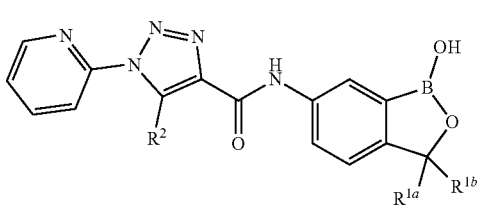

or a pharmaceutically acceptable salt thereof.
17. The compound of any one of embodiments 1-7 or 10-15, wherein the compound is of formula IX:

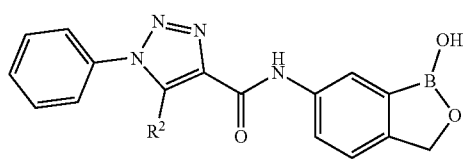

or a pharmaceutically acceptable salt thereof.
18. The compound of any one of embodiments 1-6, 8-14 or 16, wherein the compound is of formula X:

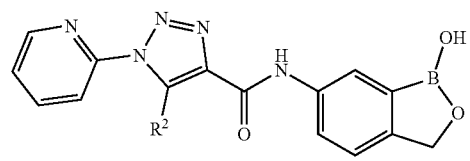

or a pharmaceutically acceptable salt thereof.
19. A compound of embodiment 11, wherein $R^3$ is optionally substituted phenyl.
20. A compound of embodiment 11, wherein $R^3$ is an optionally substituted group selected from $C_{1-6}$ aliphatic and 3- to 8-membered carbocyclyl.
21. A compound selected from the group consisting of:

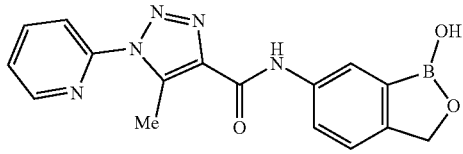 [SMILES: Cc1c(C(=O)Nc2ccc3c(c2)B(O)OC3)nnn1-c1ccccn1]

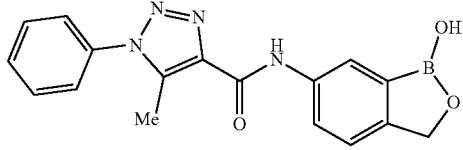 [SMILES: Cc1c(C(=O)Nc2ccc3c(c2)B(O)OC3)nnn1-c1ccccc1]

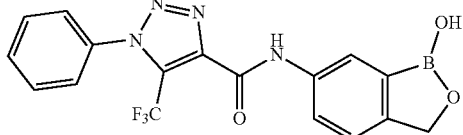

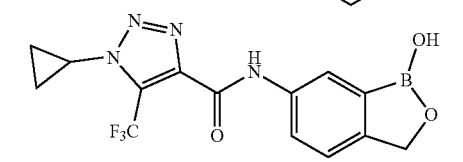

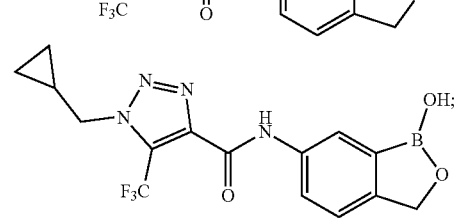

and

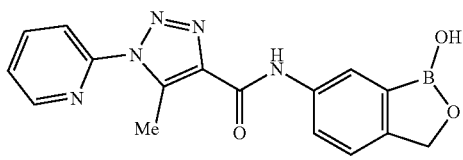

or a pharmaceutically acceptable salt thereof.
22. The compound of embodiment 21, wherein the compound is

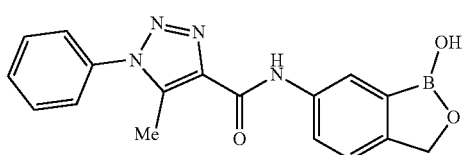

or a pharmaceutically acceptable salt thereof.
23. The compound of embodiment 21, wherein the compound is

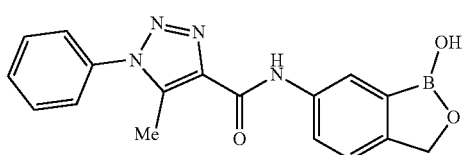

or a pharmaceutically acceptable salt thereof.

24. The compound of embodiment 21, wherein the compound is

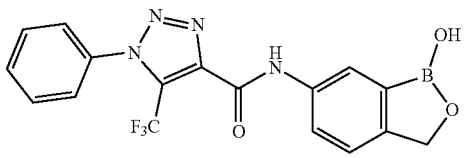 [SMILES: O=C(Nc1ccc2c(c1)B(O)OC2)c1nnn(-c2ccccc2)c1C(F)(F)F]

or a pharmaceutically acceptable salt thereof.
25. The compound of embodiment 21, wherein the compound is

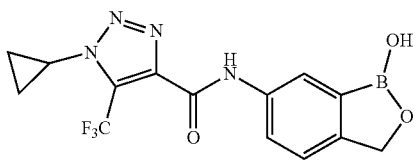 [SMILES: O=C(Nc1ccc2c(c1)B(O)OC2)c1nnn(C2CC2)c1C(F)(F)F]

or a pharmaceutically acceptable salt thereof.
26. The compound of embodiment 21, wherein the compound is

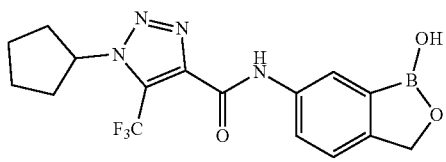 [SMILES: O=C(Nc1ccc2c(c1)B(O)OC2)c1nnn(C2CCCC2)c1C(F)(F)F]

or a pharmaceutically acceptable salt thereof.
27. The compound of embodiment 21, wherein the compound is

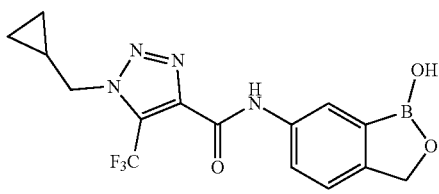 [SMILES: O=C(Nc1ccc2c(c1)B(O)OC2)c1nnn(CC2CC2)c1C(F)(F)F]

or a pharmaceutically acceptable salt thereof.
28. A compound of a formula as described in any of Examples 1-103.
29. The compound of embodiment 22, wherein the compound is N-(1-hydroxy-1,3-dihydrobenzo[c][1,2]oxaborol-6-yl)-5-methyl-1-(pyridin-2-yl)-1H-1,2,3-triazole-4-carboxamide arginine monohydrate.
30. A pharmaceutical composition comprising a compound of any one of embodiments 1-29 and a pharmaceutically acceptable excipient.
31. A method of treating or inhibiting a parasitic infection in a subject, the method comprising administering to the subject a compound of any one of embodiments 1-29.
32. A method of treating a parasitic infection associated with *Leishmania* comprising administering to a subject a compound of any one of embodiments 1-29.
33. The method of embodiment 31 or 32 wherein the parasitic infection is associated with *L. major, L. donovani,* *L. mexicana, L. tropica, L. aethiopica, L. peruviana, L. guyanensis, L. braziliensis,* or *L. infantum*.
34. The method of embodiment 33 wherein the parasitic infection is associated with *L. donovani*.
35. The method of embodiment 33 wherein the parasitic infection is associated with *L. infantum*.
36. A method of treating cutaneous leishmaniasis comprising administering to a subject a compound of any one of embodiments 1-29.
37. A method for treating, preventing, inhibiting, ameliorating, or eradicating the pathology and/or symptomology of a disease caused by a parasite, comprising administering to a subject in need thereof a compound of any one of embodiments 1-29.
38. The method of embodiment 37, wherein the disease is leishmaniasis.
39. The method of embodiment 38, wherein the disease is cutaneous leishmaniasis.
40. The method of embodiment 38, wherein the disease is mucocutaneous leishmaniasis or visceral leishmaniasis.
41. The method of embodiment 40, wherein the disease is visceral leishmaniasis.
42. A method of preventing and/or treating pathogen infections and/or a pathology associated with a pathogen infection in a patient in need thereof, comprising administering to the patient a compound of any one of embodiments 1-29.
43. A method of reducing the Leishman-Donovan Unit (LDU) of leishmaniasis in a host, comprising administering an a compound of any one of embodiments 1-29.
44. A method of treating a *T. congolense*-mediated disease or disorder in a subject comprising administering to a subject a compound of any one of embodiments 1-29 or a composition of embodiment 30.
45. A method of treating a *T. vivax*-mediated disease or disorder in a subject comprising administering to a subject a compound of any one of embodiments 1-29 or a composition of embodiment 30.
46. A method of treating a *T. cruzi*-mediated disease or disorder in a subject comprising administering to a subject a compound of any one of embodiments 1-29 or a composition of embodiment 30.
47. The method of embodiment 46, wherein the disease or disorder is Chagas disease.
48. The method of embodiment 46 or 47, wherein the subject is a mammal.
49. The method of any one of embodiments 46-48, wherein the subject is a human.
50. The method of any one of embodiments 46-48, wherein the subject is a dog.

EXAMPLES

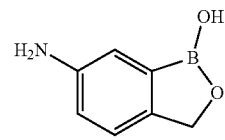

Amino-CBO 1

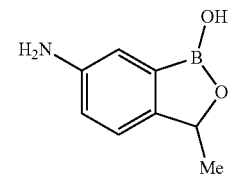

Amino-CBO 2

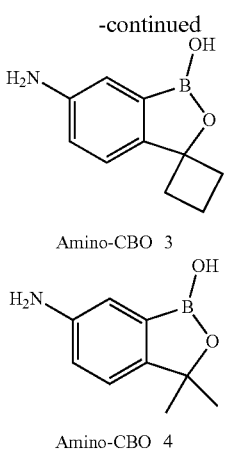

Amino-CBO 3

Amino-CBO 4

The synthesis of Amino-CBO-1, Amino-CBO-2 Amino-CBO-3 and Amino-CBO-4 were previously described in WO 2011/019618 and *Future Med. Chem.* 2011, 3, 1259-1278.

Example 1. N-(1-hydroxy-1,3-dihydrobenzo[c][1,2]oxaborol-6-yl)-5-methyl-1-phenyl-1H-Example 11,2,3-triazole-4-carboxamide (I-1)

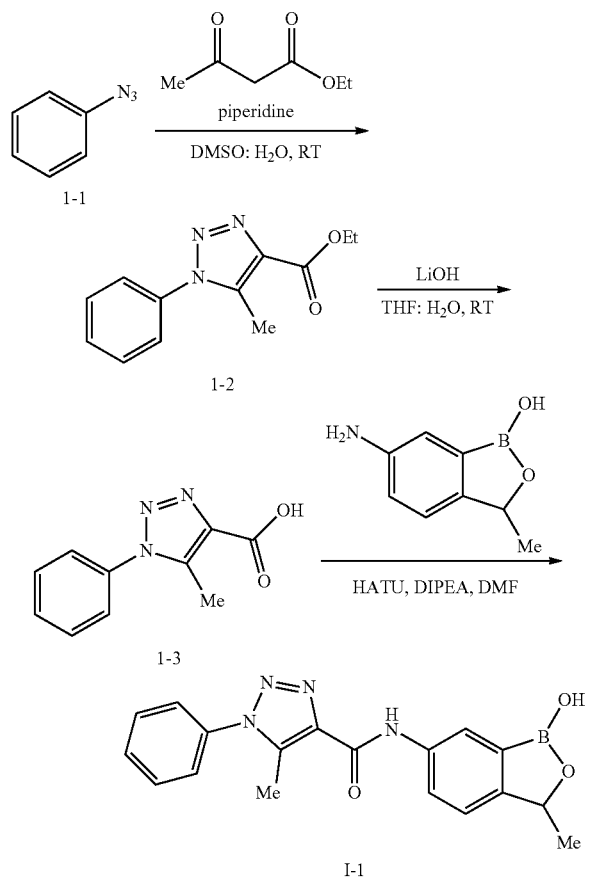

Step 1

To a solution of ethyl acetoacetate (1.2 equiv.) in a mixture of DMSO:H$_2$O (9:1, 10 vol) was added piperidine (0.2 equiv.) and was stirred at RT for 30 min. Then compound I-1 (5.0 g, 1.0 equiv.) was added to the reaction mixture and stirring was continued at RT for 24 h. The progress of the reaction was monitored by TLC. TLC indicated formation a polar spot with completed consumption of starting material. After work-up and column purification 1.9 g of compound I-2 was isolated.

Step 2

To a stirred solution of compound I-2 (1.9 g) in THF:H$_2$O (3:1, 10 vol) was added LiOH.H$_2$O (3 equiv.) at RT. The reaction mixture was stirred at RT for 16 h. The progress of the reaction was monitored by TLC. TLC indicated formation of a polar spot with completed consumption of starting material. The solvent was removed under reduced pressure to get the residue, which was acidified with 2N HCl at 0° C. until pH 3.0 to get solid compound. The resultant solid was filtered and dried under vacuum to give 1.3 g of compound I-3.

Step 3

To a stirred solution of compound I-3 (1.3 g) in DMF (13 mL) was added DIPEA (3.0 equiv.) and HATU (2.0 equiv.). The reaction mixture was stirred at RT for 15 min. Then Amino-CBO-2 (1.1 equiv.) was added to the reaction mixture and was stirred at RT for 18 h. TLC indicated formation of a polar spot with complete consumption of both the starting materials. After work-up, 1.4 g of crude compound was obtained. The crude mixture was purified via reverse phase chromatography to give 1.09 g of I-1 as a pale yellow solid. $^1$H NMR (300 MHz, DMSO-d$_6$): δ 10.54 (s, 1H), 9.14 (s, 1H), 8.22 (d, J=1.5 Hz, 1H), 7.82 (dd, J=8.1, 2.1 Hz, 1H), 7.67 (m, 5H), 7.38 (d, J=8.1 Hz, 1H), 5.20 (m, 1H), 2.55 (m, 3H), 1.40 (d, J=6.6 Hz, 3H); LC-MS: m/z=349.39 [M+H]$^+$. HPLC purity: 95.81% (220 nm) and 96.64% (254 nm), chiral HPLC purity is 96.87% (215 nm).

Example 2. N-(1-hydroxy-1,3-dihydrobenzo[c][1,2]oxaborol-6-yl)-1-phenyl-1H-1,2,3-triazole-4-carboxamide (I-2)

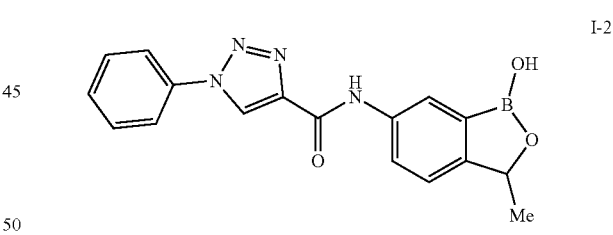

To a stirred solution of azidobenzene (1.0 g) in a mixture of tBuOH:H2O was added ethylpropiolate (1.0 eq). The reaction mixture was stirred at RT for 10 min, then CuSO$_4$ (0.1 eq) followed by sodium ascorbate (0.3 eq) was added. The reaction mixture was stirred at RT for 24 h. TLC indicated formation of polar spots along-with un-reacted starting material. After work-up and column purification 300 mg of ethyl 1-phenyl-1H-1,2,3-triazole-4-carboxylate was isolated. $^1$H NMR (400 MHz, DMSO-d$_6$): δ 9.48 (s, 1H), 8.02 (d, J=7.8 Hz, 2H), 7.60 (m, 3H), 4.38 (q, J=7.4 Hz, 2H), 1.36 (t, J=7.4 Hz, 3H); LC-MS: m/z 218.3 [M+H]+.

To a stirred solution of ethyl 1-phenyl-1H-1,2,3-triazole-4-carboxylate (300 mg) in a mixture of THF/water (7:3) was lithium hydroxide monohydrate (3.0 equiv). The reaction mixture was stirred at RT for 16 h. TLC indicated complete consumption of starting material. After acidification and extraction with ethyl acetate, the organic layer was separated, dried and evaporated to afford the crude product, which was triturated with diethyl ether/pentane to give 200 mg of 1-phenyl-1H-1,2,3-triazole-4-carboxylic acid. $^1$H NMR (400 MHz, DMSO-d$_6$): δ 13.2 (s, 1H), 9.38 (s, 1H), 7.98 (d, J=7.8 Hz, 2H), 7.52 (m, 3H); LC-MS: m/z 190.2 [M+H]+.

Compound I-2 was prepared in a similar manner to step 3 of Example 1 with 1-phenyl-1H-1,2,3-triazole-4-carboxylic acid replacing 5-methyl-1-phenyl-1H-1,2,3-triazole-4-carboxylic acid. $^1$H NMR (400 MHz, DMSO-d$_6$): δ 10.60 (s, 1H), 9.44 (s, 1H), 9.17 (s, 1H), 8.18 (d, J=1.6 Hz, 1H), 8.02 (d, J=7.8 Hz, 2H), 7.81 (dd, J=8.4, 2 Hz, 1H), 7.64 (m, 2H), 7.55 (m, 1H), 7.38 (d, J=7.8 Hz, 1H), 5.19 (m, 1H), 1.40 (d, J=9.2 Hz, 3H); LC-MS: m/z=335.4 [M+H]$^+$. HPLC purity: 98.61% (220 nm) and 99.15% (254 nm), chiral HPLC purity is 97.63% (215 nm).

Example 3. N-(1-hydroxy-1H-spiro[benzo[c][1,2]oxaborole-3,1'-cyclobutan]-6-yl)-1-phenyl-1H-1,2,3-triazole-4-carboxamide (I-3)

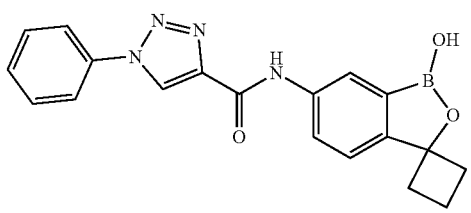

This compound was prepared in a similar manner to Example 2 with Amino-CBO-3 replacing Amino-CBO-2. $^1$H NMR (400 MHz, DMSO-d$_6$): δ 10.62 (s, 1H), 9.44 (s, 1H), 9.22 (s, 1H), 8.12 (d, J=2 Hz, 1H), 8.02 (d, J=8 Hz, 2H), 7.88 (dd, J=8.2 Hz, 1H), 7.66 (m, 3H), 7.56 (d, J=7.8 Hz, 1H), 2.34-2.44 (m, 4H), 2.04 (m, 2H); LC-MS: m/z=361.4 [M+H]$^+$. HPLC purity: 97.15% (220 nm) and 95.98% (254 nm), chiral HPLC purity is 97.74% (215 nm).

Example 4. N-(1-hydroxy-1H-spiro[benzo[c][1,2]oxaborole-3,1'-cyclobutan]-6-yl)-5-methyl-1-phenyl-1H-1,2,3-triazole-4-carboxamide (I-4)

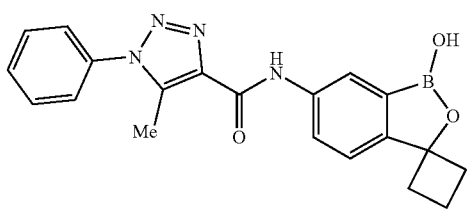

This compound was prepared in a similar manner to step 3 of Example 1 with Amino-CBO-2 replacing Amino-CBO-3. $^1$H NMR (300 MHz, DMSO-d$_6$): δ 10.56 (s, 1H), 9.20 (s, 1H), 8.17 (d, J=1.8 Hz, 1H), 7.88 (dd, J=8.1, 2.4 Hz, 1H), 7.67 (m, 5H), 7.63 (s, 3H), 2.51 (s, 3H), 2.30-2.47 (m, 4H), 2.04 (m, 2H); LC-MS: m/z=375.4 [M+H]$^+$. HPLC purity: 97.17% (220 nm) and 97.25% (254 nm), chiral HPLC purity is 96.97% (215 nm).

Example 5. 1-(4-fluorophenyl)-N-(1-hydroxy-1,3-dihydrobenzo[c][1,2]oxaborol-6-yl)-1H-1,2,3-triazole-4-carboxamide (I-5)

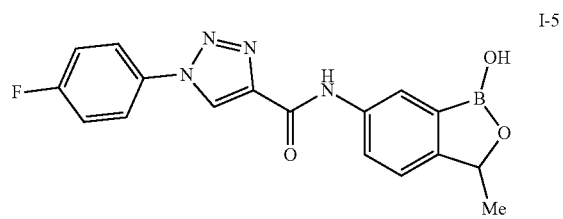 [SMILES: CC1OB(O)c2cc(NC(=O)c3cn(-c4ccc(F)cc4)nn3)ccc21]

This compound was prepared in a similar manner to Example 2 with 1-(4-fluorophenyl)-1H-1,2,3-triazole-4-carboxylic acid (Prepared via General Method 1) replacing 1-phenyl-1H-1,2,3-triazole-4-carboxylic acid. $^1$H NMR (400 MHz, DMSO-d$_6$): δ 10.60 (s, 1H), 9.42 (s, 1H), 9.17 (s, 1H), 8.18 (d, J=2 Hz, 1H), 8.06 (m, 2H), 7.82 (dd, J=8.4, 2.4 Hz, 1H), 7.50 (m, 2H), 7.38 (d, J=8.4 Hz, 1H), 5.20 (m, 1H), 1.40 (d, J=6.8 Hz, 3H); LC-MS: m/z=353.38 [M+H]$^+$. HPLC purity: 98.17% (220 nm) and 97.96% (254 nm), chiral HPLC purity is 99.53% (215 nm).

Example 6. 1-(4-fluorophenyl)-N-(1-hydroxy-3-methyl-1,3-dihydrobenzo[c][1,2]oxaborol-6-yl)-5-methyl-1H-1,2,3-triazole-4-carboxamide (I-6)

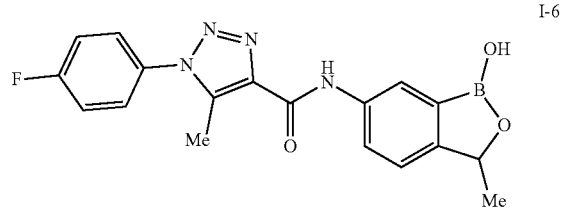 [SMILES: Cc1c(C(=O)Nc2ccc3c(c2)B(O)OC3C)nnn1-c1ccc(F)cc1]

This compound was prepared in a similar manner to Example 1 with 1-(4-fluorophenyl)-5-methyl-1H-1,2,3-triazole-4-carboxylic acid (Prepared via General Method 2) replacing 5-methyl-1-phenyl-1H-1,2,3-triazole-4-carboxylic acid. $^1$H NMR (300 MHz, DMSO-d$_6$): δ 10.60 (s, 1H), 9.17 (s, 1H), 8.22 (s, 1H), 8.06 (m, 2H), 7.65-7.82 (m, 3H), 7.52 (d, J=9 Hz, 2H), 7.38 (d, J=8.1 Hz, 1H), 5.20 (m, 1H), 1.40 (d, J=6.8 Hz, 3H); LC-MS: m/z=367.41 [M+H]$^+$. HPLC purity: 98.88% (220 nm) and 98.98% (254 nm), chiral HPLC purity is 97.39% (215 nm).

Example 7. 1-(4-fluorophenyl)-N-(1-hydroxy-1H-spiro[benzo[c][1,2]oxaborole-3,1'-cyclobutan]-6-yl)-1H-1,2,3-triazole-4-carboxamide (I-7)

This compound was prepared in a similar manner to Example 2 with 1-(4-fluorophenyl)-1H-1,2,3-triazole-4-carboxylic acid (Prepared via General Method 1) replacing 1-phenyl-1H-1,2,3-triazole-4-carboxylic acid and Amino-CBO-3 replacing Amino-CBO-2. $^1$H NMR (400 MHz, DMSO-d$_6$): δ 10.62 (s, 1H), 9.44 (s, 1H), 9.22 (s, 1H), 8.12 (d, J=1.6 Hz, 1H), 8.06 (m, 2H), 7.88 (dd, J=8.4, 2 Hz, 1H), 7.66 (d, J=8.4 Hz, 1H), 7.50 (t, J=8.4 Hz, 2H), 2.34-2.44 (m, 4H), 2.04 (m, 2H); LC-MS: m/z=379.39 [M+H]$^+$. HPLC purity: 96.31% (220 nm) and 96.07% (254 nm), chiral HPLC purity is 99.60% (215 nm).

Example 8. N-(1-hydroxy-1H-spiro[benzo[c][1,2]oxaborole-3,1'-cyclobutan]-6-yl)-1-(pyridin-3-yl)-1H-1,2,3-triazole-4-carboxamide (I-8)

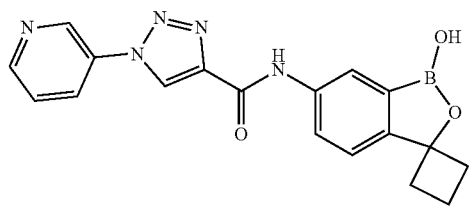

I-8

This compound was prepared in a similar manner to Example 2 with 1-(pyridin-3-yl)-1H-1,2,3-triazole-4-carboxylic acid (Prepared via General Method 6) replacing 1-phenyl-1H-1,2,3-triazole-4-carboxylic acid and Amino-CBO-3 replacing Amino-CBO-2. $^1$H NMR (300 MHz, DMSO-d$_6$): δ 10.67 (s, 1H), 9.54 (s, 1H), 9.24 (s, 2H), 8.75 (d, J=4.8 Hz, 1H), 8.40-8.48 (m, 1H), 8.13 (d, J=1.8 Hz, 1H), 7.88 (dd, J=8.4, 2.1 Hz, 1H), 7.60-7.73 (m, 2H), 2.34-2.44 (m, 4H), 2.04 (m, 2H); LC-MS: m/z=362.39 [M+H]$^+$. HPLC purity: 97.78% (220 nm) and 96.78% (254 nm), chiral HPLC purity is 95.41% (215 nm).

Example 9. 1-(4-fluorophenyl)-N-(1-hydroxy-1H-spiro[benzo[c][1,2]oxaborole-3,1'-cyclobutan]-6-yl)-5-methyl-1H-1,2,3-triazole-4-carboxamide (I-9)

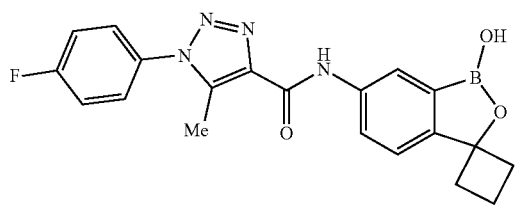

I-9

This compound was prepared in a similar manner to Example 2 with 1-(4-fluorophenyl)-5-methyl-1H-1,2,3-triazole-4-carboxylic acid (Prepared via General Method 2) replacing 1-phenyl-1H-1,2,3-triazole-4-carboxylic acid and Amino-CBO-3 replacing Amino-CBO-2. $^1$H NMR (300 MHz, DMSO-d$_6$): δ 10.56 (s, 1H), 9.20 (s, 1H), 8.16 (d, J=1.5 Hz, 1H), 7.87 (dd, J=8.4, 2.1 Hz, 1H), 7.72-7.77 (m, 2H), 7.65 (d, J=8.1 Hz, 1H), 7.52 (t, J=8.7 Hz, 2H), 2.57 (s, 3H), 2.34-2.44 (m, 4H), 2.04 (m, 2H); LC-MS: m/z=393.41 [M+H]$^+$. HPLC purity: 98.66% (220 nm) and 99% (254 nm), chiral HPLC purity is 99.87% (215 nm).

Example 10. N-(1-hydroxy-1,3-dihydrobenzo[c][1,2]oxaborol-6-yl)-1-(p-tolyl)-1H-1,2,3-triazole-4-carboxamide (MO)

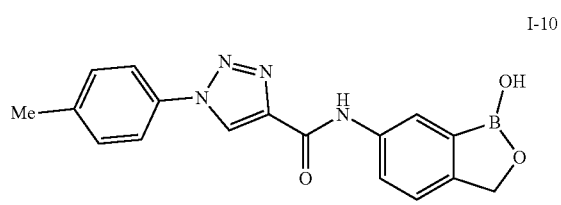 [SMILES: Cc1ccc(-n2cc(C(=O)Nc3ccc4c(c3)B(O)OC4)nn2)cc1]

I-10

This compound was prepared in a similar manner to Example 2 with 1-(p-tolyl)-1H-1,2,3-triazole-4-carboxylic acid (Prepared via General Method 1) replacing 1-phenyl-1H-1,2,3-triazole-4-carboxylic acid and Amino-CBO-1 replacing Amino-CBO-2. $^1$H NMR (300 MHz, DMSO-d$_6$): δ 10.58 (s, 1H), 9.39 (s, 1H), 9.24 (s, 1H), 8.23 (d, J=1.8 Hz, 1H), 7.88 (d, J=8.4 Hz, 2H), 7.82 (dd, J=8.4, 2.1 Hz, 1H), 7.44 (d, J=8.1 Hz, 2H), 7.39 (d, J=8.4 Hz, 1H), 4.97 (s, 2H), 2.41 (s, 3H); LC-MS: m/z=335.37 [M+H]$^+$. HPLC purity: 96.73% (220 nm) and 97.48% (254 nm), chiral HPLC purity is 97.28% (215 nm).

Example 11. N-(1-hydroxy-1,3-dihydrobenzo[c][1,2]oxaborol-6-yl)-5-methyl-1-(p-tolyl)-1H-1,2,3-triazole-4-carboxamide (I-11)

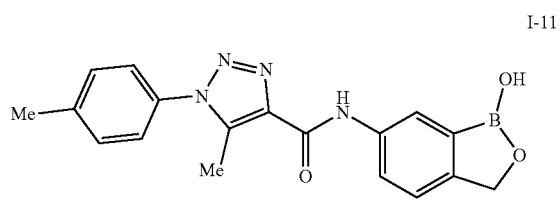 [SMILES: Cc1ccc(-n2nnc(C(=O)Nc3ccc4c(c3)B(O)OC4)c2C)cc1]

I-11

This compound was prepared in a similar manner to Example 1 with 5-methyl-1-(p-tolyl)-1H-1,2,3-triazole-4-carboxylic acid (Prepared via General Method 2) replacing 5-methyl-1-phenyl-1H-1,2,3-triazole-4-carboxylic acid and Amino-CBO-1 replacing Amino-CBO-2. $^1$H NMR (400 MHz, DMSO-d$_6$): δ 10.60 (s, 1H), 9.22 (s, 1H), 8.27 (d, J=1.6 Hz, 1H), 7.82 (dd, J=8.4, 2.4 Hz, 1H), 7.54 (d, J=8.4 Hz, 2H), 7.46 (d, J=8.4 Hz, 2H), 7.38 (d, J=8.4 Hz, 1H), 4.97 (s, 2H), 2.57 (s, 3H), 2.33 (s, 3H); LC-MS: m/z=349.39 [M+H]$^+$. HPLC purity: 99.60% (220 nm) and 99.78% (254 nm), chiral HPLC purity is 99.76% (215 nm).

Example 12. N-(1-hydroxy-3-methyl-1,3-dihydrobenzo[c][1,2]oxaborol-6-yl)-1-(pyridin-3-yl)-1H-1,2,3-triazole-4-carboxamide (I-12)

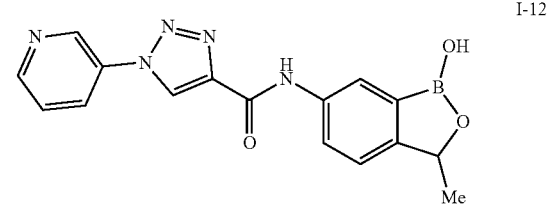 [SMILES: CC1OB(O)c2cc(NC(=O)c3cn(-c4cccnc4)nn3)ccc21]

I-12

This compound was prepared in a similar manner to Example 2 with 1-(pyridin-3-yl)-1H-1,2,3-triazole-4-carboxylic acid (Prepared via General Method 2) replacing 1-phenyl-1H-1,2,3-triazole-4-carboxylic acid. $^1$H NMR (300 MHz, DMSO-d$_6$): δ 10.65 (s, 1H), 9.54 (s, 1H), 9.24 (d, J=2.4 Hz, 1H), 9.17 (s, 1H), 8.75 (dd, J=4.8, 1.5 Hz, 1H), 8.40-8.48 (m, 1H), 8.18 (d, J=1.8 Hz, 1H), 7.82 (dd, J=8.1, 2.1 Hz, 1H), 7.70 (m, 1H), 7.39 (d, J=8.4 Hz, 1H), 5.20 (m, 1H), 1.40 (d, J=6.3 Hz, 3H); LC-MS: m/z=336.36 [M+H]$^+$. HPLC purity: 97.20% (220 nm) and 96.55% (254 nm), chiral HPLC purity is 98.66% (215 nm).

Example 13. N-(1-hydroxy-3-methyl-1,3-dihydrobenzo[c][1,2]oxaborol-6-yl)-5-methyl-1-(p-tolyl)-1H-1,2,3-triazole-4-carboxamide (I-13)

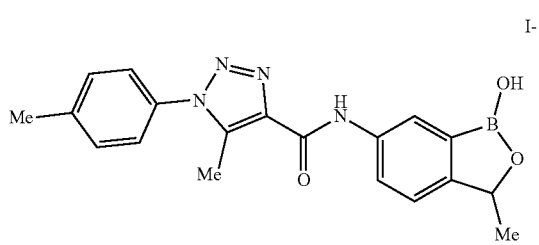

I-13

This compound was prepared in a similar manner to Example 1 with 5-methyl-1-(p-tolyl)-1H-1,2,3-triazole-4-carboxylic acid (Prepared via General Method 2) replacing 5-methyl-1-phenyl-1H-1,2,3-triazole-4-carboxylic acid. $^1$H NMR (400 MHz, DMSO-d$_6$): δ 10.60 (s, 1H), 9.13 (s, 1H), 8.22 (d, J=1.6 Hz, 1H), 7.81 (dd, J=8.4, 2 Hz, 1H), 7.54 (d, J=8 Hz, 2H), 7.46 (d, J=8.4 Hz, 2H), 7.37 (d, J=8 Hz, 1H), 5.20 (m, 1H), 2.56 (d, J=4.8 Hz, 3H), 2.48 (d, 7=3.6 Hz, 3H), 1.40 (d, J=6.4 Hz, 3H); LC-MS: m/z=363.42 [M+H]$^+$. HPLC purity: 97.58% (220 nm) and 97.24% (254 nm), chiral HPLC purity is 97.17% (215 nm).

Example 14. N-(1-hydroxy-1,3-dihydrobenzo[c][1,2]oxaborol-6-yl)-5-methyl-1-phenyl-1H-1,2,3-triazole-4-carboxamide (I-14)

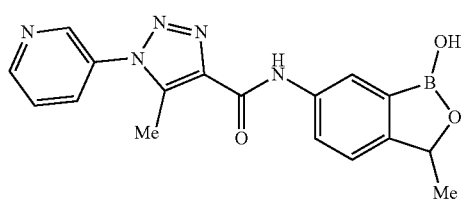

I-14

This compound was prepared in a similar manner to Example 1 with 5-methyl-1-(pyridin-3-yl)-1H-1,2,3-triazole-4-carboxylic acid (Prepared via General Method 7) replacing 5-methyl-1-phenyl-1H-1,2,3-triazole-4-carboxylic acid. $^1$H NMR (300 MHz, DMSO-d$_6$): δ 10.58 (s, 1H), 9.14 (s, 1H), 8.92 (s, 1H), 8.84 (d, J=4.8 Hz, 1H), 8.16-8.24 (m, 2H), 7.82 (d, J=9.9 Hz, 1H), 7.74 (m, 1H), 7.37 (d, J=8.4 Hz, 1H), 5.20 (m, 1H), 2.62 (s, 3H), 1.40 (d, J=6.6 Hz, 3H); LC-MS: m/z=350.41 [M+H]$^+$. HPLC purity: 96.72% (220 nm) and 97.35% (254 nm), chiral HPLC purity is 98.27% (215 nm).

Example 15. N-(1-hydroxy-1,3-dihydrobenzo[c][1,2]oxaborol-6-yl)-5-methyl-1-phenyl-1H-1,2,3-triazole-4-carboxamide (I-15)

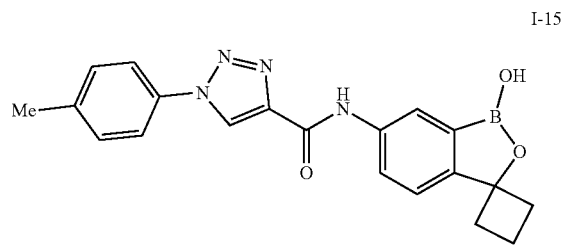 [SMILES: Cc1ccc(-n2cc(C(=O)Nc3ccc4c(c3)B(O)OC43CCC3)nn2)cc1]

I-15

This compound was prepared in a similar manner to Example 2 with 1-(p-tolyl)-1H-1,2,3-triazole-4-carboxylic acid (Prepared via General Method 1) replacing 1-phenyl-1H-1,2,3-triazole-4-carboxylic acid and Amino-CBO-3 replacing Amino-CBO-2. $^1$H NMR (400 MHz, DMSO-d$_6$): δ 10.60 (s, 1H), 9.39 (s, 1H), 9.22 (s, 1H), 8.12 (d, J=2 Hz, 1H), 7.88 (m, 3H), 7.66 (d, J=8.4 Hz, 1H), 7.44 (d, J=8.4 Hz, 2H), 2.34-2.44 (m, 7H), 2.04 (m, 2H); LC-MS: m/z=375.43 [M+H]$^+$. HPLC purity: 96.53% (220 nm) and 96.99% (254 nm), chiral HPLC purity is 99.40% (215 nm).

Example 16. N-(1-hydroxy-1H-spiro[benzo[c][1,2]oxaborole-3,1'-cyclobutan]-6-yl)-5-methyl-1-(p-tolyl)-1H-1,2,3-triazole-4-carboxamide (I-16)

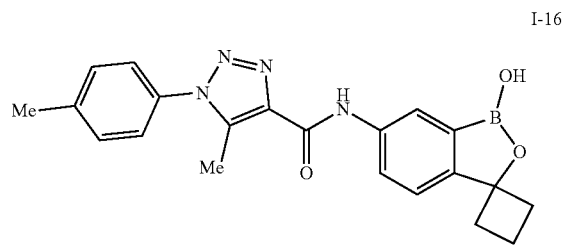 [SMILES: Cc1ccc(-n2nnc(C(=O)Nc3ccc4c(c3)B(O)OC43CCC3)c2C)cc1]

I-16

This compound was prepared in a similar manner to Example 1 with 5-methyl-1-(p-tolyl)-1H-1,2,3-triazole-4-carboxylic acid (Prepared via General Method 2) replacing 5-methyl-1-phenyl-1H-1,2,3-triazole-4-carboxylic acid and Amino-CBO-3 replacing Amino-CBO-2. $^1$H NMR (400 MHz, DMSO-d$_6$): δ 10.54 (s, 1H), 9.20 (s, 1H), 8.16 (d, J=2 Hz, 1H), 7.86 (dd, J=8.4, 2 Hz, 1H), 7.64 (d, J=8.4 Hz, 1H), 7.54 (d, J=8.4 Hz, 2H), 7.46 (d, J=8.4 Hz, 2H), 2.56 (s, 3H), 2.43 (s, 3H), 2.34-2.44 (m, 4H), 2.04 (m, 2H); LC-MS: m/z=389.45 [M+H]$^+$. HPLC purity: 99.44% (220 nm) and 97.74% (254 nm), chiral HPLC purity is 98.06% (215 nm).

Example 17. N-(1-hydroxy-1H-spiro[benzo[c][1,2]oxaborole-3,1'-cyclobutan]-6-yl)-5-methyl-1-(pyridin-3-yl)-1H-1,2,3-triazole-4-carboxamide (I-17)

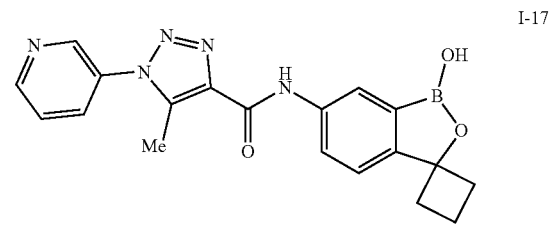 [SMILES: Cc1c(C(=O)Nc2ccc3c(c2)B(O)OC32CCC2)nnn1-c1cccnc1]

I-17

This compound was prepared in a similar manner to Example 1 with 5-methyl-1-(pyridin-3-yl)-1H-1,2,3-triazole-4-carboxylic acid (Prepared via General Method 7) replacing 5-methyl-1-phenyl-1H-1,2,3-triazole-4-carboxylic acid and Amino-CBO-3 replacing Amino-CBO-2. $^1$H NMR (300 MHz, DMSO-$d_6$): δ 10.60 (s, 1H), 9.20 (s, 1H), 8.92 (d, J=2.7 Hz, 1H), 8.84 (dd, J=4.5, 1.5 Hz, 1H), 8.16-8.24 (m, 2H), 7.87 (dd, J=8.4, 1.8 Hz, 1H), 7.74 (m, 1H), 7.37 (d, J=8.4 Hz, 1H), 2.62 (s, 3H), 2.34-2.44 (m, 4H), 2.04 (m, 2H); LC-MS: m/z=376.39 [M+H]$^+$. HPLC purity: 99.63% (220 nm) and 99.69% (254 nm), chiral HPLC purity is 99.62% (215 nm).

Example 18. N-(1-hydroxy-3-methyl-1,3-dihydrobenzo[c][1,2]oxaborol-6-yl)-1-(p-tolyl)-1H-1,2,3-triazole-4-carboxamide (I-18)

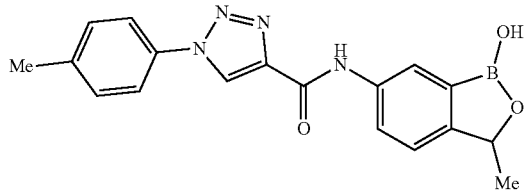

I-18

This compound was prepared in a similar manner to Example 2 with 1-(p-tolyl)-1H-1,2,3-triazole-4-carboxylic acid (Prepared via General Method 1) replacing 1-phenyl-1H-1,2,3-triazole-4-carboxylic acid. $^1$H NMR (400 MHz, DMSO-$d_6$): δ 10.58 (s, 1H), 9.38 (s, 1H), 9.16 (s, 1H), 8.18 (d, J=1.2 Hz, 1H), 7.88 (d, J=8.4 Hz, 2H), 7.81 (dd, J=8.4, 2 Hz, 1H), 7.44 (d, J=8.4 Hz, 2H), 7.38 (d, J=8.4 Hz, 1H), 5.20 (m, 1H), 2.41 (s, 3H), 1.40 (d, J=6 Hz, 3H); LC-MS: m/z=349.42 [M+H]$^+$. HPLC purity: 96.71% (220 nm) and 96.37% (254 nm), chiral HPLC purity is 97.14% (215 nm).

Example 19. N-(1-hydroxy-3-methyl-1,3-dihydrobenzo[c][1,2]oxaborol-6-yl)-1-(4-methoxyphenyl)-5-methyl-1H-1,2,3-triazole-4-carboxamide (I-19)

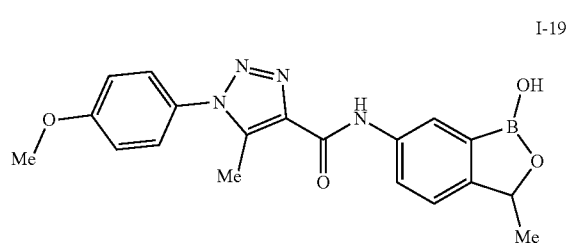 [SMILES: COc1ccc(-n2nnc(C(=O)Nc3ccc4c(c3)B(O)OC4C)c2C)cc1]

I-19

This compound was prepared in a similar manner to Example 1 with 1-(4-methoxyphenyl)-5-methyl-1H-1,2,3-triazole-4-carboxylic acid (Prepared via General Method 2) replacing 5-methyl-1-phenyl-1H-1,2,3-triazole-4-carboxylic acid. $^1$H NMR (400 MHz, DMSO-$d_6$): δ 10.50 (s, 1H), 9.14 (s, 1H), 8.22 (d, J=2 Hz, 1H), 7.81 (dd, J=8.4, 2 Hz, 1H), 7.58 (d, J=8.8 Hz, 2H), 7.37 (d, J=8.4 Hz, 1H), 7.18 (d, J=8.8 Hz, 2H), 5.20 (m, 1H), 3.87 (s, 3H), 2.55 (s, 3H), 1.40 (d, J=6.4 Hz, 3H); LC-MS: m/z=379.42 [M+H]$^+$. HPLC purity: 99.08% (220 nm) and 99.75% (254 nm), chiral HPLC purity is 98.84% (215 nm).

Example 20. N-(1-hydroxy-1H-spiro[benzo[c][1,2]oxaborole-3,1'-cyclobutan]-6-yl)-1-(4-methoxyphenyl)-5-methyl-1H-1,2,3-triazole-4-carboxamide (I-20)

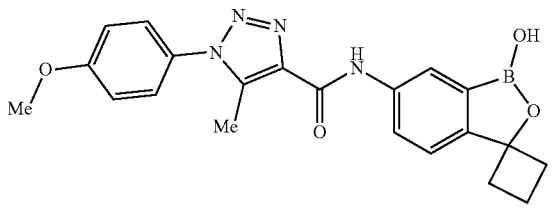

I-20

This compound was prepared in a similar manner to Example 1 with 1-(4-methoxyphenyl)-5-methyl-1H-1,2,3-triazole-4-carboxylic acid (Prepared via General Method 2) replacing 5-methyl-1-phenyl-1H-1,2,3-triazole-4-carboxylic acid and Amino-CBO-3 replacing Amino-CBO-2. $^1$H NMR (300 MHz, DMSO-$d_6$): δ 10.52 (s, 1H), 9.20 (s, 1H), 8.17 (s, 1H), 7.87 (dd, J=8.4, 1.8 Hz, 1H), 7.64 (d, J=8.4 Hz, 1H), 7.58 (d, J=8.7 Hz, 2H), 7.18 (d, J=9.3 Hz, 2H), 3.87 (s, 3H), 2.55 (s, 3H), 2.34-2.47 (m, 4H), 2.04 (m, 2H); LC-MS: m/z=405.43 [M+H]$^+$. HPLC purity: 99.05% (220 nm) and 98.51% (254 nm), chiral HPLC purity is 99.40% (215 nm).

Example 21. N-(1-hydroxy-1,3-dihydrobenzo[c][1,2]oxaborol-6-yl)-1-(4-methoxyphenyl)-1H-1,2,3-triazole-4-carboxamide (I-21)

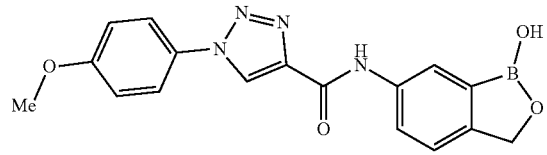

I-21

This compound was prepared in a similar manner to Example 2 with 1-(4-methoxyphenyl)-5-methyl-1H-1,2,3-triazole-4-carboxylic acid (Prepared via General Method 1) replacing 1-phenyl-1H-1,2,3-triazole-4-carboxylic acid and Amino-CBO-1 replacing Amino-CBO-2. $^1$H NMR (300 MHz, DMSO-$d_6$): δ 10.58 (s, 1H), 9.34 (s, 1H), 9.24 (s, 1H), 8.23 (d, J=1.5 Hz, 1H), 7.92 (d, J=9.3 Hz, 2H), 7.83 (dd, J=8.1, 1.8 Hz, 1H), 7.40 (d, J=8.1 Hz, 1H), 111 (d, J=9.3 Hz, 2H), 4.97 (s, 2H), 3.85 (s, 3H); LC-MS: m/z=351.40 [M+H]$^+$. HPLC purity: 97.68% (220 nm) and 97.68% (254 nm), chiral HPLC purity is 95.51% (215 nm).

Example 22. N-(1-hydroxy-3-methyl-1,3-dihydrobenzo[c][1,2]oxaborol-6-yl)-1-(4-methoxyphenyl)-1H-1,2,3-triazole-4-carboxamide (I-22)

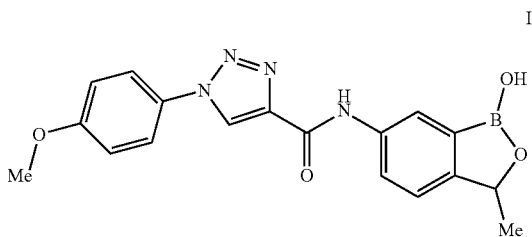

I-22

This compound was prepared in a similar manner to Example 2 with 1-(4-methoxyphenyl)-5-methyl-1H-1,2,3-triazole-4-carboxylic acid (Prepared via General Method 1) replacing 1-phenyl-1H-1,2,3-triazole-4-carboxylic acid. $^1$H NMR (300 MHz, DMSO-$d_6$): δ 10.58 (s, 1H), 9.33 (s, 1H), 9.16 (s, 1H), 8.18 (s, 1H), 7.92 (d, J=8.7 Hz, 2H), 7.83 (d, J=8.1 Hz, 1H), 7.39 (d, J=8.4 Hz, 1H), 7.17 (d, J=9 Hz, 2H), 5.20 (m, 1H), 3.85 (s, 3H), 1.40 (d, J=6.6 Hz, 3H); LC-MS: m/z=365.46 [M+H]$^+$. HPLC purity: 97.66% (220 nm) and 96.46% (254 nm), chiral HPLC purity is 95.14% (215 nm).

Example 23. N-(1-hydroxy-3-methyl-1,3-dihydrobenzo[c][1,2]oxaborol-6-yl)-1-(pyridin-2-yl)-1H-1,2,3-triazole-4-carboxamide (I-23)

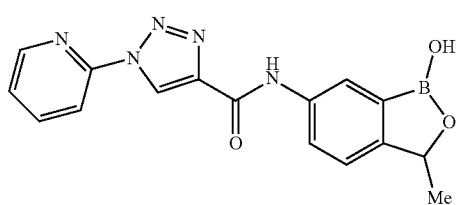

I-23

This compound was prepared in a similar manner to Example 2 with 1-(pyridin-2-yl)-1H-1,2,3-triazole-4-carboxylic acid (Prepared via General Method 4) replacing 1-phenyl-1H-1,2,3-triazole-4-carboxylic acid. $^1$H NMR (300 MHz, DMSO-$d_6$): δ 10.65 (s, 1H), 9.38 (s, 1H), 9.17 (s, 1H), 8.67 (d, J=4.8 Hz, 1H), 8.16-8.24 (m, 3H), 7.82 (dd, J=8.1, 1.8 Hz, 1H), 7.63 (m, 1H), 7.39 (d, J=8.1 Hz, 1H), 5.20 (m, 1H), 1.40 (d, J=6.6 Hz, 3H); LC-MS: m/z=336.42 [M+H]$^+$. HPLC purity: 99.09% (220 nm) and 99.41% (254 nm), chiral HPLC purity is 98.22% (215 nm).

Example 24. N-(1-hydroxy-3-methyl-1,3-dihydrobenzo[c][1,2]oxaborol-6-yl)-5-methyl-1-(pyridin-2-yl)-1H-1,2,3-triazole-4-carboxamide (I-24)

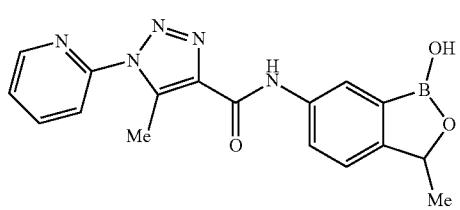

I-24

This compound was prepared in a similar manner to Example 1 with 5-methyl-1-(pyridin-2-yl)-1H-1,2,3-triazole-4-carboxylic acid (Prepared via General Method 5) replacing 5-methyl-1-phenyl-1H-1,2,3-triazole-4-carboxylic acid. $^1$H NMR (300 MHz, DMSO-$d_6$): δ 10.56 (s, 1H), 9.14 (s, 1H), 8.71 (d, J=3.9 Hz, 1H), 8.16-8.24 (m, 2H), 7.97 (d, J=8.1, 1.8 Hz, 1H), 7.82 (dd, J=8.1 Hz, 1H), 7.67 (m, 1H), 7.37 (d, J=8.1 Hz, 1H), 5.20 (m, 1H), 2.82 (s, 3H), 1.40 (d, J=6.6 Hz, 3H); LC-MS: m/z=350.45 [M+H]$^+$. HPLC purity: 98.19% (220 nm) and 98.16% (254 nm), chiral HPLC purity is 96.34% (215 nm).

Example 25. N-(1-hydroxy-1H-spiro[benzo[c][1,2]oxaborole-3,1'-cyclobutan]-6-yl)-1-(4-methoxyphenyl)-1H-1,2,3-triazole-4-carboxamide (I-25)

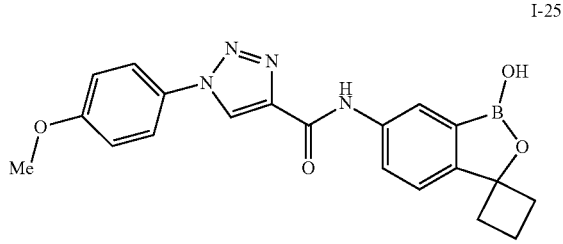 [SMILES: COc1ccc(-n2cc(C(=O)Nc3ccc4c(c3)B(O)OC43CCC3)nn2)cc1]

I-25

This compound was prepared in a similar manner to Example 2 with 1-(4-methoxyphenyl)-5-methyl-1H-1,2,3-triazole-4-carboxylic acid (Prepared via General Method 1) replacing 1-phenyl-1H-1,2,3-triazole-4-carboxylic acid and Amino-CBO-3 replacing Amino-CBO-2. $^1$H NMR (300 MHz, DMSO-$d_6$): δ 10.58 (s, 1H), 9.36 (s, 1H), 9.22 (s, 1H), 8.12 (d, J=1.5 Hz, 1H), 7.84-7.94 (m, 3H), 7.66 (d, J=8.4 Hz, 1H), 7.17 (d, J=9.3 Hz, 2H), 3.85 (s, 3H), 2.34-2.44 (m, 7H), 2.04 (m, 2H); LC-MS: m/z=391.50 [M+H]$^+$. HPLC purity: 97.71% (220 nm) and 97.15% (254 nm), chiral HPLC purity is 97.11% (215 nm).

Example 26. N-(1-hydroxy-1H-spiro[benzo[c][1,2]oxaborole-3,1'-cyclobutan]-6-yl)-1-(pyridin-2-yl)-1H-1,2,3-triazole-4-carboxamide (I-26)

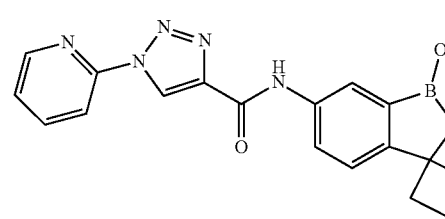

I-26

This compound was prepared in a similar manner to Example 2 with 1-(pyridin-2-yl)-1H-1,2,3-triazole-4-carboxylic acid (Prepared via General Method 4) replacing 1-phenyl-1H-1,2,3-triazole-4-carboxylic acid and Amino-CBO-3 replacing Amino-CBO-2. $^1$H NMR (300 MHz, DMSO-$d_6$): δ 10.61 (s, 1H), 9.39 (s, 1H), 9.24 (s, 1H), 8.68 (d, J=4.8 Hz, 1H), 8.10-8.23 (m, 3H), 7.88 (dd, J=8.4, 1.8 Hz, 1H), 7.60-7.70 (m, 2H), 2.34-2.44 (m, 4H), 2.04 (m, 2H); LC-MS: m/z=362.43 [M+H]$^+$. HPLC purity: 96.67% (220 nm) and 97.52% (254 nm), chiral HPLC purity is 96.91% (215 nm).

Example 27. N-(1-hydroxy-1H-spiro[benzo[c][1,2]oxaborole-3,1'-cyclobutan]-6-yl)-5-methyl-1-(pyridin-2-yl)-1H-1,2,3-triazole-4-carboxamide (I-27)

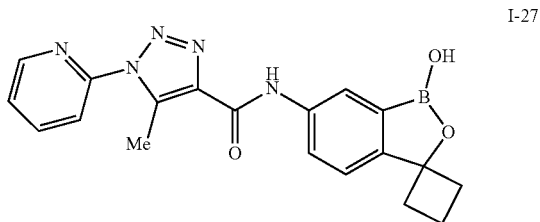 [SMILES: Cc1c(C(=O)Nc2ccc3c(c2)B(O)OC32CCC2)nnn1-c1ccccn1]

This compound was prepared in a similar manner to Example 1 with 5-methyl-1-(pyridin-2-yl)-1H-1,2,3-triazole-4-carboxylic acid (Prepared via General Method 5) replacing 5-methyl-1-phenyl-1H-1,2,3-triazole-4-carboxylic acid and Amino-CBO-3 replacing Amino-CBO-2. $^1$H NMR (400 MHz, DMSO-d$_6$): δ 10.58 (s, 1H), 9.20 (s, 1H), 8.71 (d, J=4.4 Hz, 1H), 8.15-8.22 (m, 2H), 7.97 (d, J=8 Hz, 1H), 7.87 (d, J=8.4 Hz, 1H), 7.67 (m, 2H), 2.82 (s, 3H), 2.34-2.44 (m, 4H), 2.04 (m, 2H); LC-MS: m/z=376.45 [M+H]$^+$. HPLC purity: 97.86% (220 nm) and 98.31% (254 nm), chiral HPLC purity is 99.35% (215 nm).

Example 28. 1-ethyl-N-(1-hydroxy-1,3-dihydrobenzo[c][1,2]oxaborol-6-yl)-5-(trifluoromethyl)-1H-1,2,3-triazole-4-carboxamide (I-28)

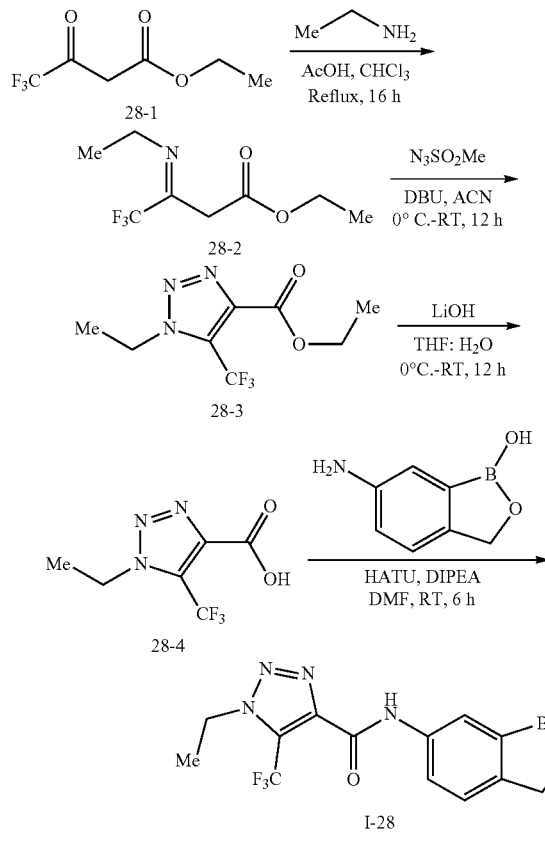

Step 1

To a stirred solution of compound 28-1 (1.0 g, 1.0 equiv.) and ethyl amine (1.1 equiv.) in CHCl$_3$ (10 vol) was added AcOH (1.1 equiv.) portion wise at RT for 16 h. The reaction mixture was stirred at reflux. The progress of the reaction was monitored by TLC. TLC indicated formation a polar spot with completed consumption of starting material. After work-up and column purification of the crude mixture 500 mg of compound 28-2 was isolated.

Step 2

To a stirred solution of compound 28-2 (500 mg 1.0 equiv.) in CAN (10 vol) was added DBU (0.34 equiv.) at 0° C. followed by N$_3$SO$_2$Me (0.34 equiv.). The reaction mixture was stirred at RT for 12 h. The reaction mixture was stirred at reflux temperature for 12 h. The progress of the reaction was monitored by TLC. TLC indicated formation a polar spot with completed consumption of the starting material. After work-up and column purification give 230 mg of compound 28-3.

Step 3

To a stirred solution of compound 28-3 (230 mg) in THF:H$_2$O (3:1, 10 vol) was added LiOH.H$_2$O (3 equiv.) at RT. The reaction mixture was stirred at RT for 12 h. The progress of the reaction was monitored by TLC. TLC indicated formation of a polar spot with completed consumption of starting material. The solvent was removed under reduced pressure to get the residue, which was acidified with 2N HCl at 0° C. until pH 3.0 to get solid compound. The resultant solid was filtered and dried under vacuum to give 100 mg of compound 28-4. $^1$H NMR and LC-MS were as expected (not shown).

Step 4

To a stirred solution of compound 28-4 (100 mg) in DMF (13 mL) was added DIPEA (3.0 equiv.) and HATU (2.0 equiv.). The reaction mixture was stirred at RT for 15 min. Then Amino-CBO-1 (1.1 equiv.) was added to the reaction mixture and was stirred at RT for 6 h. TLC indicated formation of a polar spot with complete consumption of both the starting materials. After work-up, the crude mixture was purified via reverse phase chromatography to give 100 mg of I-28 as an off-white solid. $^1$H NMR (300 MHz, DMSO-d$_6$): δ 10.84 (s, 1H), 9.26 (s, 1H), 8.24 (s, 1H), 7.75 (d, J=8.4 Hz, 1H), 7.40 (d, J=8.1 Hz, 1H), 7.40 (d, J=8.1 Hz, 1H), 7.17 (d, J=9.3 Hz, 2H), 4.98 (s, 2H), 4.68 (q, J=7.2 Hz, 2H), 1.52 (t, J=7.2 Hz, 3H); LC-MS: m/z=341.19 [M+H]$^+$. HPLC purity: 98.95% (220 nm) and 98.79% (254 nm), chiral HPLC purity is 99.86% (215 nm).

Example 29. 1-cyclopropyl-N-(1-hydroxy-1,3-dihydrobenzo[c][1,2]oxaborol-6-yl)-5-(trifluoromethyl)-1H-1,2,3-triazole-4-carboxamide (I-29)

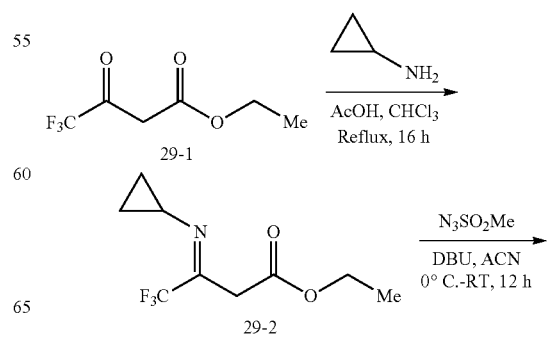

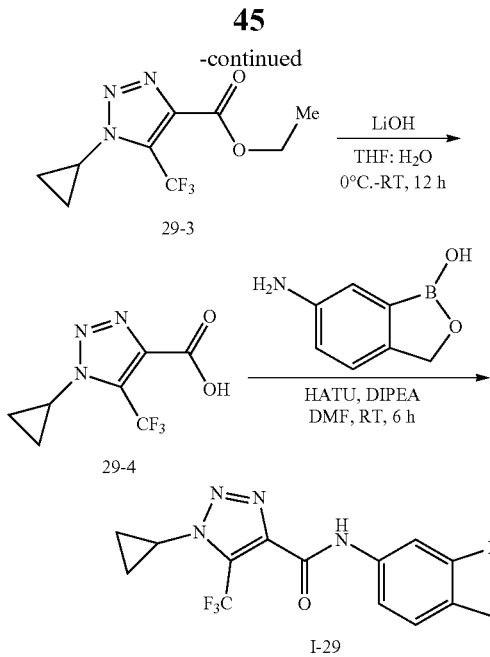

δ 10.83 (s, 1H), 9.25 (s, 1H), 8.22 (d, J=1.2 Hz, 1H), 7.74 (dd, J=8, 2 Hz, 1H), 7.39 (d, J=8 Hz, 1H), 7.40 (d, J=8.1 Hz, 1H), 4.97 (s, 2H), 4.09 (m, 1H), 1.38 (m, 2H), 1.28 (m, 2H); LC-MS: m/z=353.15 [M+H]⁺. HPLC purity: 99.15% (220 nm) and 99.77% (254 nm), chiral HPLC purity is 99.04% (215 nm).

Example 30. 1-cyclopentyl-N-(1-hydroxy-1,3-dihydrobenzo[c][1,2]oxaborol-6-yl)-5-(trifluoromethyl)-1H-1,2,3-triazole-4-carboxamide (I-30)

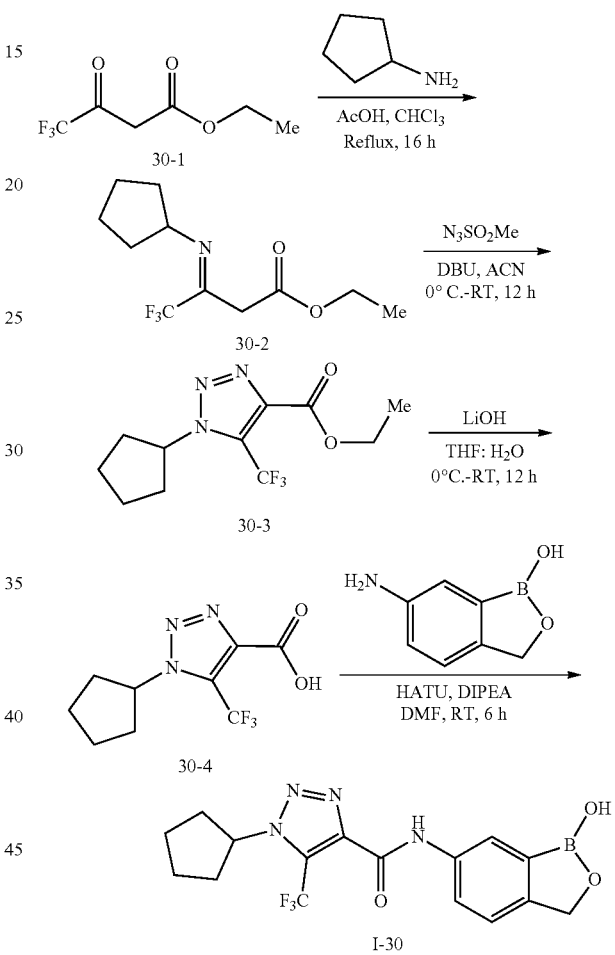

Step 1
To a stirred solution of compound 29-1 (1.0 g, 1.0 equiv.) and cyclopropyl amine (1.1 equiv.) in CHCl₃ (10 vol) was added AcOH (1.1 equiv.) portion wise at RT for 16 h. The reaction mixture was stirred at reflux. The progress of the reaction was monitored by TLC. TLC indicated formation a polar spot with completed consumption of starting material. After work-up and column purification of the crude mixture 400 mg of compound 29-2 was isolated. LC/MS m/z 224 [M+H]⁺.

Step 2
To a stirred solution of compound 29-2 (400 mg 1.0 equiv.) in ACN (10 vol) was added DBU (0.34 equiv.) at 0° C. followed by N₃SO₂Me (0.34 equiv.). The reaction mixture was stirred at RT for 12 h. The reaction mixture was stirred at reflux temperature for 12 h. The progress of the reaction was monitored by TLC. TLC indicated formation a polar spot with complete consumption of the starting material. After work-up and column purification 300 mg of compound 29-3 were recovered. LC/MS m/z 250 [M+H]⁺.

Step 3
To a stirred solution of compound 29-3 (300 mg) in THF:H₂O (3:1, 10 vol) was added LiOH.H₂O (3 equiv.) at RT. The reaction mixture was stirred at RT for 12 h. The progress of the reaction was monitored by TLC. TLC indicated formation of a polar spot with completed consumption of starting material. The solvent was removed under reduced pressure to get the residue, which was acidified with 2N HCl at 0° C. until pH 3.0 to get solid compound. The resultant solid was filtered and dried under vacuum to give 150 mg of compound 29-4. ¹H NMR and LC-MS were as expected (not shown).

Step 4
To a stirred solution of compound 29-4 (150 mg) in DMF (10 mL) was added DIPEA (3.0 equiv.) and HATU (2.0 equiv.). The reaction mixture was stirred at RT for 15 min. Then Amino-CBO-1 (1.1 equiv.) was added to the reaction mixture and was stirred at RT for 6 h. TLC indicated formation of a polar spot with complete consumption of both the starting materials. After work-up, the crude mixture was purified via reverse phase chromatography to give 84 mg of I-29 as an off-white solid. ¹H NMR (400 MHz, DMSO-d₆):

Step 1
To a stirred solution of compound 30-1 (1.0 g, 1.0 equiv.) and cyclopentyl amine (1.1 equiv.) in CHCl₃ (10 vol) was added AcOH (1.1 equiv.) portion wise at RT for 16 h. The reaction mixture was stirred at reflux. The progress of the reaction was monitored by TLC. TLC indicated formation a polar spot with completed consumption of starting material. After work-up and column purification of the crude mixture 700 mg of compound 30-2 was isolated. LC/MS m/z 252 [M+H]⁺.

Step 2
To a stirred solution of compound 30-2 (700 mg 1.0 equiv.) in ACN (10 vol) was added DBU (0.34 equiv.) at 0° C. followed by N₃SO₂Me (0.34 equiv.). The reaction mixture was stirred at RT for 12 h. The reaction mixture was stirred at reflux temperature for 12 h. The progress of the reaction was monitored by TLC. TLC indicated formation a polar spot with complete consumption of the starting material. After work-up and column purification 400 mg of compound 30-3 were recovered. LC/MS m/z 278 [M+H]⁺.

Step 3

To a stirred solution of compound 30-3 (400 mg) in THF:H₂O (3:1, 10 vol) was added LiOH.H₂O (3 equiv.) at RT. The reaction mixture was stirred at RT for 12 h. The progress of the reaction was monitored by TLC. TLC indicated formation of a polar spot with completed consumption of starting material. The solvent was removed under reduced pressure to get the residue, which was acidified with 2N HCl at 0° C. until pH 3.0 to get solid compound. The resultant solid was filtered and dried under vacuum to give 200 mg of compound 30-4. LC/MS m/z 250 [M+H]⁺.

Step 4

To a stirred solution of compound 30-4 (150 mg) in DMF (10 mL) was added DIPEA (3.0 equiv.) and HATU (2.0 equiv.). The reaction mixture was stirred at RT for 15 min. Then Amino-CBO-1 (1.1 equiv.) was added to the reaction mixture and was stirred at RT for 6 h. TLC indicated formation of a polar spot with complete consumption of both the starting materials. After work-up, the crude mixture was purified via reverse phase chromatography to give 54 mg of I-30 as an off-white solid. ¹H NMR (400 MHz, DMSO-d₆): δ 10.84 (s, 1H), 9.26 (s, 1H), 8.19 (d, J=1.2 Hz, 1H), 7.72 (dd, J=8, 2 Hz, 1H), 7.39 (d, J=8.4 Hz, 1H), 5.16 (m, 1H), 4.97 (s, 2H), 2.26 (m, 2H), 2.15 (m, 2H), 1.89 (m, 2H), 1.76 (m, 2H); LC-MS: m/z=381.19 [M+H]⁺. HPLC purity: 98.85% (220 nm) and 99.15% (254 nm), chiral HPLC purity is 99.69% (215 nm).

Example 31. N-(1-hydroxy-1,3-dihydrobenzo[c][1,2]oxaborol-6-yl)-1-propyl-5-(trifluoromethyl)-1H-1,2,3-triazole-4-carboxamide (I-31)

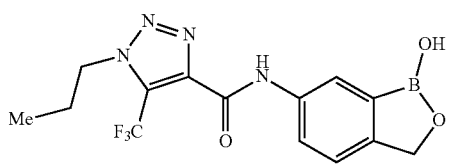

I-31

This compound was prepared in a similar manner to step 4 of Example 28 with 1-propyl-5-(trifluoromethyl)-1H-1,2,3-triazole-4-carboxylic acid (Prepared via General Method 3) replacing 1-ethyl-5-(trifluoromethyl)-1H-1,2,3-triazole-4-carboxylic acid, ¹H NMR (400 MHz, DMSO-d₆): δ 10.84 (s, 1H), 9.25 (s, 1H), 8.23 (s, 1H), 7.74 (dd, J=8, 1.6 Hz, 1H), 7.39 (d, J=8.4 Hz, 1H), 4.97 (s, 2H), 4.61 (t, J=7.2 Hz, 1H), 1.92 (m, 2H), 0.92 (t, J=7.2 Hz, 3H); LC-MS: m/z=355.25 [M+H]⁺. HPLC purity: 99.51% (220 nm) and 99.47% (254 nm), chiral HPLC purity is 99.56% (215 nm).

Example 32. N-(1-hydroxy-1,3-dihydrobenzo[c][1,2]oxaborol-6-yl)-1-isopropyl-5-(trifluoromethyl)-1H-1,2,3-triazole-4-carboxamide (I-32)

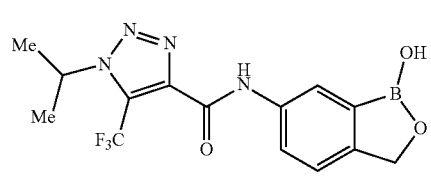

I-32

This compound was prepared in a similar manner to step 4 of Example 28 with 1-isopropyl-5-(trifluoromethyl)-1H-1,2,3-triazole-4-carboxylic acid (Prepared via General Method 3) replacing 1-ethyl-5-(trifluoromethyl)-1H-1,2,3-triazole-4-carboxylic acid. ¹H NMR (400 MHz, DMSO-d₆): δ 10.85 (s, 1H), 9.25 (s, 1H), 8.19 (d, J=1.2 Hz, 1H), 7.73 (dd, J=8, 2 Hz, 1H), 7.40 (d, J=8 Hz, 1H), 5.00 (m, 1H), 4.97 (s, 2H), 1.63 (d, J=6.4 Hz, 6H); LC-MS: m/z=355.22 [M+H]⁺. HPLC purity: 98.62% (220 nm) and 99.87% (254 nm), chiral HPLC purity is 97.70% (215 nm).

Example 33. N-(1-hydroxy-1,3-dihydrobenzo[c][1,2]oxaborol-6-yl)-1-(2-methoxyethyl)-5-(trifluoromethyl)-1H-1,2,3-triazole-4-carboxamide (I-33)

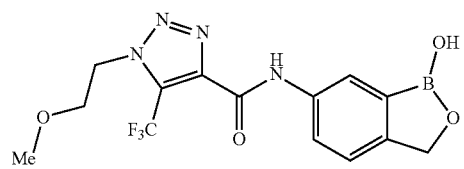

I-33

This compound was prepared in a similar manner to step 4 of Example 28 with 1-(2-methoxyethyl)-5-(trifluoromethyl)-1H-1,2,3-triazole-4-carboxylic acid (Prepared via General Method 3) replacing 1-ethyl-5-(trifluoromethyl)-1H-1,2,3-triazole-4-carboxylic acid, ¹H NMR (400 MHz, DMSO-d₆): δ 10.84 (s, 1H), 9.25 (s, 1H), 8.23 (d, J=1.6 Hz, 1H), 7.75 (dd, J=8.4, 2 Hz, 1H), 7.39 (d, J=8 Hz, 1H), 4.97 (s, 2H), 4.82 (t, J=4.8 Hz, 2H), 3.80 (t, J=4.8 Hz, 2H), 3.25 (s, 3H); LC-MS: m/z=371.26 [M+H]⁺. HPLC purity: 99.88% (220 nm) and 99.08% (254 nm), chiral HPLC purity is 99.58% (215 nm).

Example 34. 1-(cyclopropylmethyl)-N-(1-hydroxy-1,3-dihydrobenzo[c][1,2]oxaborol-6-yl)-5-(trifluoromethyl)-1H-1,2,3-triazole-4-carboxamide (I-34)

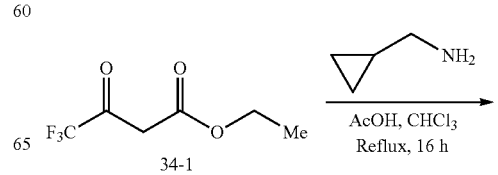

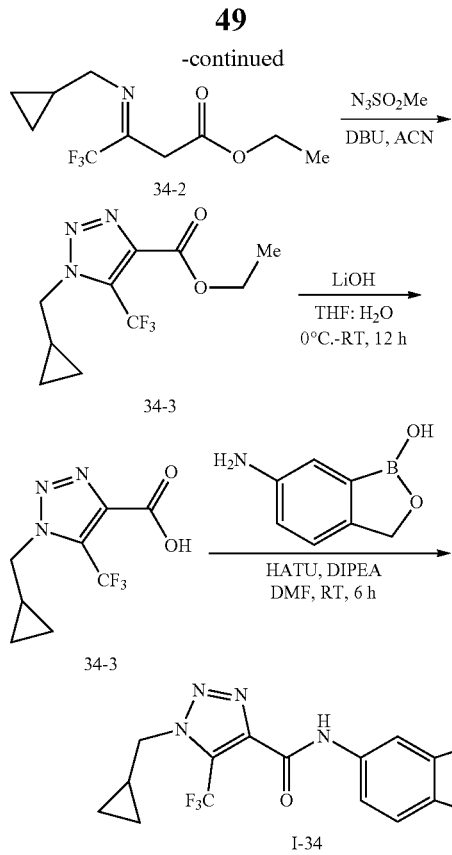

Step 1

To a stirred solution of compound 34-1 (1.0 g, 1.0 equiv.) and cyclopropylmethyl amine (1.1 equiv.) in CHCl₃ (10 vol) was added AcOH (1.1 equiv.) portion wise at RT for 16 h. The reaction mixture was stirred at reflux. The progress of the reaction was monitored by TLC. TLC indicated formation a polar spot with completed consumption of starting material. After work-up and column purification of the crude mixture 700 mg of compound 34-2 was isolated. ¹H NMR (400 MHz, DMSO-d₆): δ 8.30 (s, 1H), 4.98 (s, 1H), 4.14 (q, J=7.4 Hz, 2H), 3.16 (m, 2H), 1.22 (t, J=7.4 Hz, 3H), 1.04 (m, 1H), 0.50 (m, 2H), 0.25 (m, 2H); LC/MS m/z 238 [M+H]⁺.

Step 2

To a stirred solution of compound 34-2 (700 mg 1.0 equiv.) in ACN (10 vol) was added DBU (0.34 equiv.) at 0° C. followed by N₃SO₂Me (0.34 equiv.). The reaction mixture was stirred at RT for 12 h. The reaction mixture was stirred at reflux temperature for 12 h. The progress of the reaction was monitored by TLC. TLC indicated formation a polar spot with complete consumption of the starting material. After work-up and column purification 400 mg of compound 34-3 was recovered. LC/MS m/z 264 [M+H]⁺.

Step 3

To a stirred solution of compound 34-3 (400 mg) in THF:H₂O (3:1, 10 vol) was added LiOH.H₂O (3 equiv.) at RT. The reaction mixture was stirred at RT for 12 h. The progress of the reaction was monitored by TLC. TLC indicated formation of a polar spot with completed consumption of starting material. The solvent was removed under reduced pressure to get the residue, which was acidified with 2N HCl at 0° C. until pH 3.0 to get solid compound. The resultant solid was filtered and dried under vacuum to give 200 mg of compound 34-4. ¹H NMR (400 MHz, DMSO-d₆): δ 4.49 (d, J=9.6 Hz, 2H), 1.29 (m, 1H), 0.57 (m, 2H), 0.47 (m, 2H); LC/MS m/z 236 [M+H]⁺.

Step 4

To a stirred solution of compound 34-4 (150 mg) in DMF (10 mL) was added DIPEA (3.0 equiv.) and HATU (2.0 equiv.). The reaction mixture was stirred at RT for 15 min. Then Amino-CBO-1 (1.1 equiv.) was added to the reaction mixture and was stirred at RT for 6 h. TLC indicated formation of a polar spot with complete consumption of both the starting materials. After work-up, the crude mixture was purified via reverse phase chromatography to give 85 mg of I-34 as an off-white solid. ¹H NMR (400 MHz, DMSO-d₆): δ 10.85 (s, 1H), 9.25 (s, 1H), 8.23 (d, J=1.2 Hz, 1H), 7.75 (dd, J=8.4, 2 Hz, 1H), 7.40 (d, J=8 Hz, 1H), 4.97 (s, 2H), 4.54 (d, J=7.6 Hz, 2H), 1.34 (m, 1H), 0.62 (m, 2H), 0.49 (m, 2H); C-MS: m/z=367.23 [M+H]⁺. HPLC purity: 98.14% (220 nm) and 98.47% (254 nm), chiral HPLC purity is 99.07% (215 nm).

Example 35. 1-(cyclopentylmethyl)-N-(1-hydroxy-1,3-dihydrobenzo[c][1,2]oxaborol-6-yl)-5-(trifluoromethyl)-1H-1,2,3-triazole-4-carboxamide (I-35)

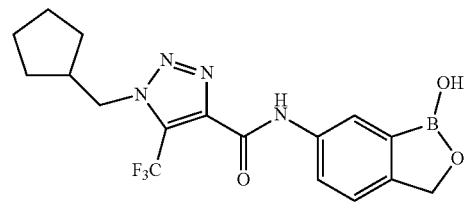

This compound was prepared in a similar manner to step 4 of Example 28 with 1-(cyclopentyl)-5-(trifluoromethyl)-1H-1,2,3-triazole-4-carboxylic acid (Prepared via General Method 3) replacing 1-ethyl-5-(trifluoromethyl)-1H-1,2,3-triazole-4-carboxylic acid, ¹H NMR (400 MHz, DMSO-d₆): δ 10.84 (s, 1H), 9.25 (s, 1H), 8.23 (d, J=1.2 Hz, 1H), 7.75 (dd, J=8.4, 2 Hz, 1H), 7.40 (d, J=8 Hz, 1H), 4.97 (s, 2H), 4.57 (d, J=7.6 Hz, 2H), 2.43 (m, 1H), 1.67 (m, 4H), 1.56 (m, 2H), 1.33 (m, 2H); LC-MS: m/z=395.26 [M+H]⁺. HPLC purity: 99.08% (220 nm) and 99.07% (254 nm), chiral HPLC purity is 99.91% (215 nm).

Example 36. N-(1-hydroxy-1,3-dihydrobenzo[c][1,2]oxaborol-6-yl)-5-methyl-1-propyl-1H-1,2,3-triazole-4-carboxamide (I-37)

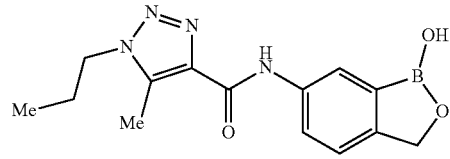

This compound was prepared in a similar manner to step 3 of Example 1 with 5-methyl-1-propyl-1H-1,2,3-triazole-4-carboxylic acid (Prepared via General Method 3) replacing 5-methyl-1-phenyl-1H-1,2,3-triazole-4-carboxylic acid and Amino-CBO-1 replacing Amino-CBO-2. ¹H NMR (400 MHz, DMSO-d₆): δ 10.35 (s, 1H), 9.19 (s, 1H), 8.23 (d, J=2 Hz, 1H), 7.79 (dd, J=8.4, 2 Hz, 1H), 7.36 (d, J=8 Hz, 1H), 4.96 (s, 2H), 4.33 (t, J=7.6 Hz, 1H), 2.59 (s, 3H), 1.85 (m, 2H), 0.89 (t, J=7.2 Hz, 3H); LC-MS: m/z=301.25 [M+H]⁺. HPLC purity: 97.31% (220 nm) and 96.78% (254 nm), chiral HPLC purity is 95.37% (215 nm).

Example 37. N-(1-hydroxy-1,3-dihydrobenzo[c][1,2]oxaborol-6-yl)-1-isopropyl-5-methyl-1H-1,2,3-triazole-4-carboxamide (I-37)

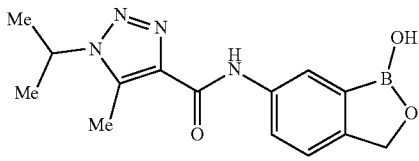

This compound was prepared in a similar manner to step 3 of Example 1 with 1-isopropyl-5-methyl-1H-1,2,3-triazole-4-carboxylic acid (Prepared via General Method 3) replacing 5-methyl-1-phenyl-1H-1,2,3-triazole-4-carboxylic acid and Amino-CBO-1 replacing Amino-CBO-2. $^1$H NMR (400 MHz, DMSO-d$_6$): δ 10.33 (s, 1H), 9.20 (s, 1H), 8.23 (d, J=1.6 Hz, 1H), 7.79 (dd, J=8.4, 2 Hz, 1H), 7.36 (d, J=8 Hz, 1H), 4.96 (s, 2H), 4.75 (m, 1H), 2.61 (s, 3H), 1.54 (d, J=6.8 Hz, 6H); LC-MS: m/z=301.25 [M+H]⁺. HPLC purity: 99.24% (220 nm) and 99.86% (254 nm), chiral HPLC purity is 98.49% (215 nm).

Example 38. 1-cyclopropyl-N-(1-hydroxy-1,3-dihydrobenzo[c][1,2]oxaborol-6-yl)-5-methyl-1H-1,2,3-triazole-4-carboxamide (I-38)

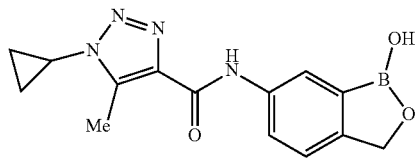

This compound was prepared in a similar manner to step 3 of Example 1 with 1-cyclopropyl-5-methyl-1H-1,2,3-triazole-4-carboxylic acid (Prepared via General Method 3) replacing 5-methyl-1-phenyl-1H-1,2,3-triazole-4-carboxylic acid and Amino-CBO-1 replacing Amino-CBO-2. $^1$H NMR (400 MHz, DMSO-d$_6$): δ 10.35 (s, 1H), 9.19 (s, 1H), 8.23 (d, J=2 Hz, 1H), 7.78 (dd, J=8, 2 Hz, 1H), 7.35 (d, J=8.4 Hz, 1H), 4.96 (s, 2H), 3.74 (m, 1H), 2.65 (s, 3H), 1.21 (m, 4H); LC-MS: m/z=299.23 [M+H]⁺. HPLC purity: 98.98% (220 nm) and chiral HPLC purity is 99.55% (215 nm).

Example 39. N-(1-hydroxy-1,3-dihydrobenzo[c][1,2]oxaborol-6-yl)-5-methyl-1-(2,2,2-trifluoroethyl)-1H-1,2,3-triazole-4-carboxamide (I-39)

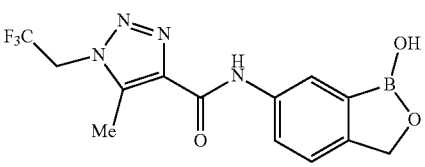

This compound was prepared in a similar manner to step 4 of Example 28 with 5-methyl-1-(2,2,2-trifluoroethyl)-1H-1,2,3-triazole-4-carboxylic acid (Prepared via General Method 3) replacing 5-methyl-1-phenyl-1H-1,2,3-triazole-4-carboxylic acid, $^1$H NMR (400 MHz, DMSO-d$_6$): δ 10.49 (s, 1H), 9.21 (s, 1H), 8.23 (d, J=1.6 Hz, 1H), 7.79 (dd, J=7.6, 2 Hz, 1H), 7.37 (d, J=8.4 Hz, 1H), 5.61 (q, J=9.2 Hz, 2H), 4.96 (s, 2H), 2.64 (s, 3H); LC-MS: m/z=341.25 [M+H]⁺. HPLC purity: 99.61% (220 nm) and 99.69% (254 nm), chiral HPLC purity is 99.72% (215 nm).

Example 40. N-(1-hydroxy-1,3-dihydrobenzo[c][1,2]oxaborol-6-yl)-1-(2-methoxyethyl)-5-methyl-1H-1,2,3-triazole-4-carboxamide (I-40)

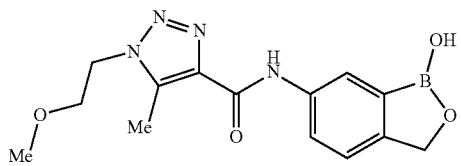

This compound was prepared in a similar manner to step 3 of Example 1 with 1-(2-methoxyethyl)-5-methyl-1H-1,2,3-triazole-4-carboxylic acid (Prepared via General Method 3) replacing 5-methyl-1-phenyl-1H-1,2,3-triazole-4-carboxylic acid and Amino-CBO-1 replacing Amino-CBO-2. $^1$H NMR (400 MHz, DMSO-d$_6$): δ 10.35 (s, 1H), 9.19 (s, 1H), 8.23 (d, J=2 Hz, 1H), 7.79 (dd, J=8.2 Hz, 1H), 7.36 (d, J=8.4 Hz, 1H), 4.96 (s, 2H), 4.55 (t, J=5.6 Hz, 2H), 3.74 (t, J=5.6 Hz, 2H), 3.24 (s, 3H), 2.59 (s, 3H); LC-MS: m/z=317.29 [M+H]⁺. HPLC purity: 97.28% (220 nm) and 97.54% (254 nm), chiral HPLC purity is 98.24% (215 nm).

Example 41. 1-cyclopentyl-N-(1-hydroxy-1,3-dihydrobenzo[c][1,2]oxaborol-6-yl)-5-methyl-1H-1,2,3-triazole-4-carboxamide (I-41)

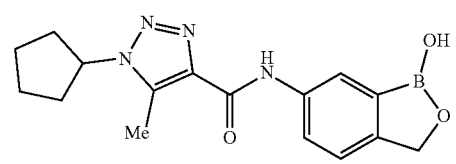

This compound was prepared in a similar manner to step 3 of Example 1 with 1-cyclopentyl-5-methyl-1H-1,2,3-triazole-4-carboxylic acid (Prepared via General Method 3) replacing 5-methyl-1-phenyl-1H-1,2,3-triazole-4-carboxylic acid and Amino-CBO-1 replacing Amino-CBO-2. $^1$H NMR (400 MHz, DMSO-d$_6$): δ 10.32 (s, 1H), 9.19 (s, 1H), 8.23 (d, J=2 Hz, 1H), 7.78 (dd, J=8.4, 2 Hz, 1H), 7.35 (d, J=8.4 Hz, 1H), 4.96 (s, 2H), 4.91 (m, 1H), 2.61 (s, 3H), 2.16 (m, 2H), 2.04 (m, 2H), 1.89 (m, 2H), 1.74 (m, 2H); LC-MS: m/z=327.32 [M+H]⁺. HPLC purity: 99.59% (220 nm) and 99.72% (254 nm), chiral HPLC purity is 99.69% (215 nm).

Example 42. 1-cyclobutyl-N-(1-hydroxy-1,3-dihydrobenzo[c][1,2]oxaborol-6-yl)-5-methyl-1H-1,2,3-triazole-4-carboxamide (I-42)

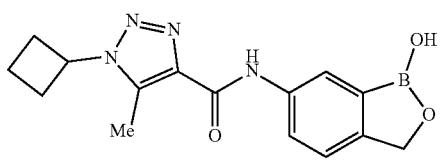

I-42

This compound was prepared in a similar manner to step 3 of Example 1 with 1-cyclobutyl-5-methyl-1H-1,2,3-triazole-4-carboxylic acid (Prepared via General Method 3) replacing 5-methyl-1-phenyl-1H-1,2,3-triazole-4-carboxylic acid and Amino-CBO-1 replacing Amino-CBO-2. $^1$H NMR (400 MHz, DMSO-$d_6$): δ 10.36 (s, 1H), 9.19 (s, 1H), 8.23 (d, J=1.6 Hz, 1H), 7.78 (dd, J=8.4, 2 Hz, 1H), 7.35 (d, J=8 Hz, 1H), 5.04 (m, 1H), 4.96 (s, 2H), 4.91 (m, 1H), 2.65 (m, 2H), 2.59 (s, 3H), 2.55 (m, 2H), 1.93 (m, 2H); LC-MS: m/z=313.29 [M+H]$^+$. HPLC purity: 99.18% (220 nm) and 99.05% (254 nm), chiral HPLC purity is 97.85% (215 nm).

Example 43. 1-(cyclopropylmethyl)-N-(1-hydroxy-1,3-dihydrobenzo[c][1,2]oxaborol-6-yl)-5-methyl-1H-1,2,3-triazole-4-carboxamide (I-43)

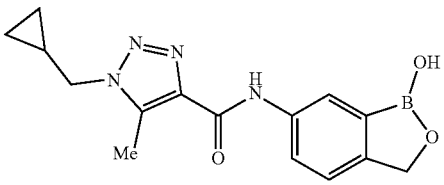

I-43

This compound was prepared in a similar manner to step 3 of Example 1 with 1-(cyclopropylmethyl)-5-methyl-1H-1,2,3-triazole-4-carboxylic acid (Prepared via General Method 3) replacing 5-methyl-1-phenyl-1H-1,2,3-triazole-4-carboxylic acid and Amino-CBO-1 replacing Amino-CBO-2. $^1$H NMR (400 MHz, DMSO-$d_6$): δ 10.34 (s, 1H), 9.20 (s, 1H), 8.23 (d, J=2 Hz, 1H), 7.78 (dd, J=8.4, 2 Hz, 1H), 7.36 (d, J=8.4 Hz, 1H), 4.96 (s, 2H), 4.27 (d, J=7.2 Hz, 2H), 2.62 (s, 3H), 1.31 (m, 1H), 0.57 (m, 2H), 0.43 (m, 2H); LC-MS: m/z=313.26 [M+H]$^+$. HPLC purity: 97.44% (220 nm) and 97.30% (254 nm), chiral HPLC purity is 97.48% (215 nm).

Example 44. 1-(cyclopentylmethyl)-N-(1-hydroxy-1,3-dihydrobenzo[c][1,2]oxaborol-6-yl)-5-methyl-1H-1,2,3-triazole-4-carboxamide (I-44)

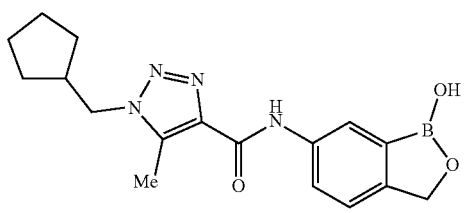

I-44

This compound was prepared in a similar manner to step 3 of Example 1 with 1-(cyclopentylmethyl)-5-methyl-1H-1,2,3-triazole-4-carboxylic acid (Prepared via General Method 3) replacing 5-methyl-1-phenyl-1H-1,2,3-triazole-4-carboxylic acid and Amino-CBO-1 replacing Amino-CBO-2. $^1$H NMR (400 MHz, DMSO-$d_6$): δ 10.35 (s, 1H), 9.20 (s, 1H), 8.23 (d, J=2 Hz, 1H), 7.78 (dd, J=8.4, 2 Hz, 1H), 7.36 (d, J=8.4 Hz, 1H), 4.96 (s, 2H), 4.30 (d, J=7.2 Hz, 2H), 2.60 (s, 3H), 2.41 (m, 1H), 1.65 (m, 4H), 1.53 (m, 2H), 1.30 (m, 2H); LC-MS: m/z=341.32 [M+H]$^+$. HPLC purity: 99.83% (220 nm) and 99.81% (254 nm), chiral HPLC purity is 99.56% (215 nm).

Example 45. 1-cyclobutyl-N-(1-hydroxy-1,3-dihydrobenzo[c][1,2]oxaborol-6-yl)-5-(trifluoromethyl)-1H-1,2,3-triazole-4-carboxamide (I-45)

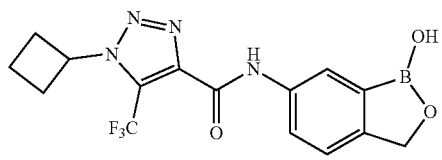

I-45

This compound was prepared in a similar manner to step 4 of Example 28 with 1-cyclobutyl-5-(trifluoromethyl)-1H-1,2,3-triazole-4-carboxylic acid (Prepared via General Method 3) replacing 1-ethyl-5-(trifluoromethyl)-1H-1,2,3-triazole-4-carboxylic acid, $^1$H NMR (400 MHz, DMSO-$d_6$): δ 10.84 (s, 1H), 9.25 (s, 1H), 8.21 (d, J=1.6 Hz, 1H), 7.73 (dd, J=8, 2 Hz, 1H), 7.40 (d, J=8 Hz, 1H), 5.26 (m, 1H), 4.97 (s, 2H), 2.75 (m, 2H), 2.57 (m, 2H), 1.95 (m, 2H); LC-MS: m/z=367.23 [M+H]$^+$. HPLC purity: 98.79% (220 nm) and 99.24% (254 nm), chiral HPLC purity is 99.25% (215 nm).

Example 46. 1-ethyl-N-(1-hydroxy-1,3-dihydrobenzo[c][1,2]oxaborol-6-yl)-5-methyl-1H-1,2,3-triazole-4-carboxamide (I-46)

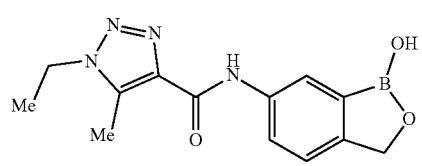

I-46

This compound was prepared in a similar manner to step 3 of Example 1 with 1-ethyl-5-methyl-1H-1,2,3-triazole-4-carboxylic acid (Prepared via General Method 3) replacing 5-methyl-1-phenyl-1H-1,2,3-triazole-4-carboxylic acid and Amino-CBO-1 replacing Amino-CBO-2. $^1$H NMR (400 MHz, DMSO-$d_6$): δ 10.34 (s, 1H), 9.19 (s, 1H), 8.23 (d, J=1.6 Hz, 1H), 7.78 (dd, J=8.4, 2 Hz, 1H), 7.35 (d, J=8.4 Hz, 1H), 4.96 (s, 2H), 4.39 (q, J=1.2 Hz, 2H), 2.60 (s, 3H), 1.42 (t, J=7.2 Hz, 3H); LC-MS: m/z=287.1 [M+H]$^+$. HPLC purity: 99.30% (220 nm) and 99.01% (254 nm), chiral HPLC purity is 99.67% (215 nm).

Example 47. 1-(cyclobutylmethyl)-N-(1-hydroxy-1,3-dihydrobenzo[c][1,2]oxaborol-6-yl)-5-(trifluoromethyl)-1H-1,2,3-triazole-4-carboxamide (I-47)

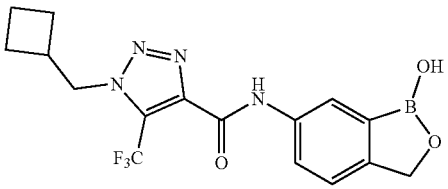

I-47

This compound was prepared in a similar manner to step 4 of Example 28 with 1-cyclobutylmethyl-5-(trifluoromethyl)-1H-1,2,3-triazole-4-carboxylic acid (Prepared via General Method 3) replacing 1-ethyl-5-(trifluoromethyl)-1H-1,2,3-triazole-4-carboxylic acid, $^1$H NMR (400 MHz, DMSO-d$_6$): δ 10.83 (s, 1H), 9.24 (s, 1H), 8.22 (s, 1H), 7.73 (d, J=8 Hz, 1H), 7.39 (d, J=8.4 Hz, 1H), 4.97 (s, 2H), 4.66 (d, J=7.2 Hz, 2H), 4.33 (t, J=7.6 Hz, 1H), 2.86 (m, 1H), 2.03 (m, 2H), 1.86 (m, 4H); LC-MS: m/z=381.0 [M+H]$^+$. HPLC purity: 99.41% (220 nm) and 99.21% (254 nm), chiral HPLC purity is 99.39% (215 nm).

Example 48. N-(1-hydroxy-1,3-dihydrobenzo[c][1,2]oxaborol-6-yl)-5-methyl-1-(6-(trifluoromethyl)pyridin-2-yl)-1H-1,2,3-triazole-4-carboxamide (I-48)

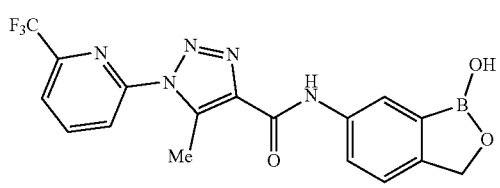

I-48

This compound was prepared in a similar manner to step 3 of Example 1, except using 2-fluoro-6-(trifluoromethyl)pyridine in place of 2-bromopyridine in General Method 5 and using Amino-CBO-1 in place of Amino-CBO-2. It was obtained as a white solid. $^1$H-NMR (400 MHz DMSO-d$_6$): δ 10.59 (s, 1H), 9.21 (s, 1H), 8.47 (t, J=8.4 Hz, 1H), 8.34 (d, J=8.4 Hz, 1H), 8.26 (s, 1H), 8.16 (d, J=7.6 Hz, 1H), 7.81 (dd, J$_1$=8.0 Hz, J$_2$=2.0 Hz, 1H), 7.37 (d, J=8.4 Hz, 1H), 4.96 (s, 2H), 2.87 (s, 3H); MS (ESI+): m/z=404.2 [M+H]$^+$; HPLC purity: 99.5% at 220 nm and 99.7% at 254 nm.

Example 49. 5-ethyl-N-(1-hydroxy-1,3-dihydrobenzo[c][1,2]oxaborol-6-yl)-1-(pyridin-2-yl)-1H-1,2,3-triazole-4-carboxamide (I-49)

I-49

This compound was prepared in a manner similar to Example 24, except using methyl 3-oxopentanoate in place of ethyl 3-oxobutanoate in General Method 5. It was obtained as a white solid.

$^1$H-NMR (400 MHz DMSO-d$_6$): δ 10.56 (s, 1H), 9.21 (s, 1H), 8.71 (d, J=5.2 Hz, 1H), 8.30 (s, 1H), 8.1-8.16 (m, 1H), 7.96 (d, J=8.0 Hz, 1H), 7.82 (d, J=8.4 Hz, 1H), 7.69-7.67 (m, 1H), 7.37 (d, J=8.4 Hz, 1H), 4.96 (s, 2H), 3.26 (q, J=7.2 Hz, 2H), 1.18 (t, J=7.6 Hz, 3H). HPLC purity: 98.4% at 220 nm and 98.7% at 254 nm; MS (ESI+): m/z=350.1 [M+H]$^+$.

Example 50. N-(1-hydroxy-1,3-dihydrobenzo[c][1,2]oxaborol-6-yl)-5-propyl-1-(pyridin-2-yl)-1H-1,2,3-triazole-4-carboxamide (I-50)

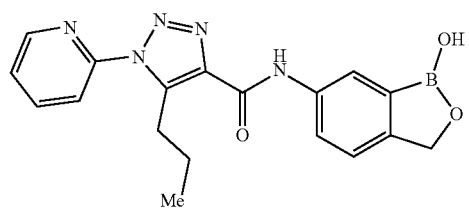

I-50

This compound was prepared in a similar manner to Example 49, except using methyl 3-oxohexanoate in place of methyl 3-oxopentanoate. It was obtained as a white solid. $^1$H-NMR (400 MHz DMSO-d$_6$): δ 10.57 (s, 1H), 9.23 (s, 1H), 8.71 (d, J=4.8 Hz, 1H), 8.32 (s, 1H), 8.20 (t, J=4.0 Hz, 1H), 7.96 (d, J=8.4 Hz, 1H), 7.80 (d, J=8.4 Hz, 1H), 7.70-7.68 (m, 1H), 7.38 (d, J=8.4 Hz, 1H), 4.98 (s, 2H), 3.32-3.26 (m, 2H), 1.64-1.55 (m, 2H), 0.84 (t, J=7.2 Hz, 3H); MS (ESI+): m/z=364.2 [M+H]$^+$; HPLC purity: 98.0% at 220 nm and 98.5% at 254 nm.

Example 51. N-(1-hydroxy-1,3-dihydrobenzo[c][1,2]oxaborol-6-yl)-5-isopropyl-1-(pyridin-2-yl)-1H-1,2,3-triazole-4-carboxamide (I-51)

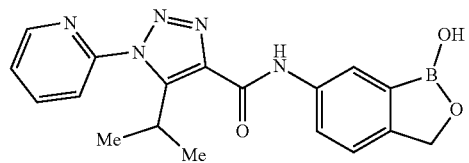

I-51

It was synthesized in a manner similar to Example 24, except using methyl 4-methyl-3-oxopentanoate in place of methyl 3-oxopentanoate in General Method 5. It was obtained as a white solid. $^1$H-NMR (400 MHz DMSO-d$_6$): δ 10.59 (s, 1H), 9.24 (s, 1H), 8.74 (t, J=4.8 Hz, 1H), 8.31 (d, J=2.0 Hz, 1H), 8.22-8.19 (m, 1H), 7.87 (d, J=8.0 Hz, 1H), 7.80 (d, J=8.4 Hz, 1H), 7.75-7.71 (m, 1H), 7.39 (d, J=8.8 Hz, 1H), 4.97 (s, 2H), 3.71-3.64 (m, 1H), 1.34 (d, J=7.2 Hz, 6H). MS (ESI+): m/z=364.1 [M+H]$^+$; HPLC purity: 98.3% at 220 nm and 99.0% at 254 nm.

Example 52. N-(1-hydroxy-1,3-dihydrobenzo[c][1,2]oxaborol-6-yl)-5-(2-methoxyethyl)-1-(pyridin-2-yl)-1H-1,2,3-triazole-4-carboxamide (I-52)

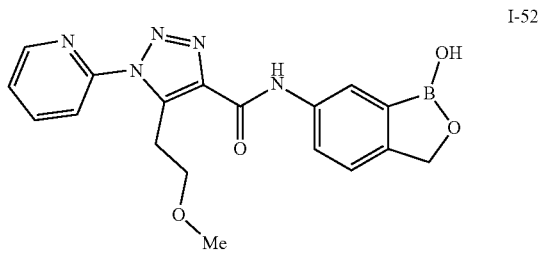 [SMILES: COCCc1c(C(=O)Nc2ccc3c(c2)B(O)OC3)nnn1-c1ccccn1]

This compound was prepared in a similar manner to Example 49, except using methyl 5-methoxy-3-oxopentanoate in place of methyl 3-oxopentanoate. It was obtained as a yellow solid. $^1$H-NMR (400 MHz DMSO-$d_6$): δ 10.64 (s, 1H), 8.71 (d, J=4.4 Hz, 1H), 8.31 (s, 1H), 8.21 (t, J=8.0 Hz, 1H), 7.95 (d, J=8.0 Hz, 1H), 7.82 (d, J=8.4 Hz, 1H), 7.70-7.67 (m, 1H), 7.39 (d, J=7.6 Hz, 1H), 4.98 (s, 2H), 3.59 (s, 4H), 3.09 (s, 3H); MS (ESI+): m/z=380.1 [M+H]$^+$. HPLC purity: 99.8% at 220 nm and 100% at 254 nm.

Example 53. N-(1-hydroxy-1,3-dihydrobenzo[c][1,2]oxaborol-6-yl)-5-(methoxymethyl)-1-(pyridin-2-yl)-1H-1,2,3-triazole-4-carboxamide (I-53)

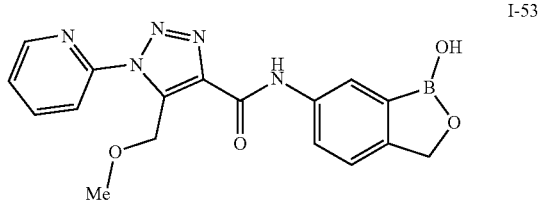 [SMILES: COCc1c(C(=O)Nc2ccc3c(c2)B(O)OC3)nnn1-c1ccccn1]

This compound was prepared in a similar manner to Example 49, except using ethyl 4-methoxy-3-oxobutanoate in place of methyl 3-oxopentanoate. It was obtained as a slightly yellowish solid. $^1$H-NMR (400 MHz DMSO-$d_6$): δ 10.71 (s, 1H), 9.24 (s, 1H), 8.71 (d, J=4 Hz, 1H), 8.27 (d, J=1.6 Hz, 1H), 8.20-8.19 (m, 1H), 7.96 (d, J=8 Hz, 1H), 7.83-7.81 (m, 1H), 7.69-7.68 (m, 1H), 7.40 (d, J=4.4 Hz, 1H), 5.15 (s, 2H), 4.98 (s, 2H), 3.16 (s, 3H); MS (ESI+): m/z=366.1 [M+H]$^+$. HPLC purity: 100% at 220 nm and 100% at 254 nm.

Example 54. 5-cyclopropyl-N-(1-hydroxy-1,3-dihydrobenzo[c][1,2]oxaborol-6-yl)-1-(pyridin-2-yl)-1H-1,2,3-triazole-4-carboxamide (I-54)

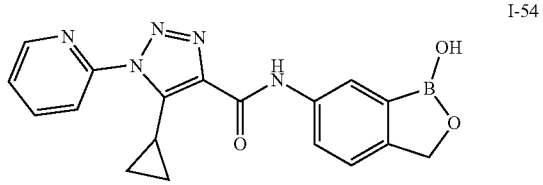 [SMILES: O=C(Nc1ccc2c(c1)B(O)OC2)c1nnn(-c2ccccn2)c1C1CC1]

This compound was prepared in a similar manner to Example 49, except using methyl 3-cyclopropyl-3-oxopropanoate in place of methyl 3-oxopentanoate. It was obtained as a white solid. $^1$H NMR (400 MHz DMSO-$d_6$): δ 10.52 (s, 1H), 9.24 (s, 1H), 8.73 (d, J=3.6 Hz, 1H), 8.27 (d, J=2.0 Hz, 1H), 8.21 (td, J=7.2 & 2.0, 1H), 7.88 (d, J=8.0 Hz, 1H), 7.79 (dd, J=8.0 & 2.0 Hz, 1H), 7.75-7.70 (m, 1H), 7.39 (d, J=8.4 Hz, 1H), 4.97 (s, 2H), 2.36-2.31 (m, 1H), 0.94-0.88 (m, 4H) ppm; MS (ESI+): m/z=362.1 [M+H]$^+$; HPLC: 99.3% in 220 nm and 99.1% in 254 nm.

Example 55. N-(1-hydroxy-1,3-dihydrobenzo[c][1,2]oxaborol-6-yl)-5-(hydroxymethyl)-1-(pyridin-2-yl)-1H-1,2,3-triazole-4-carboxamide (I-55)

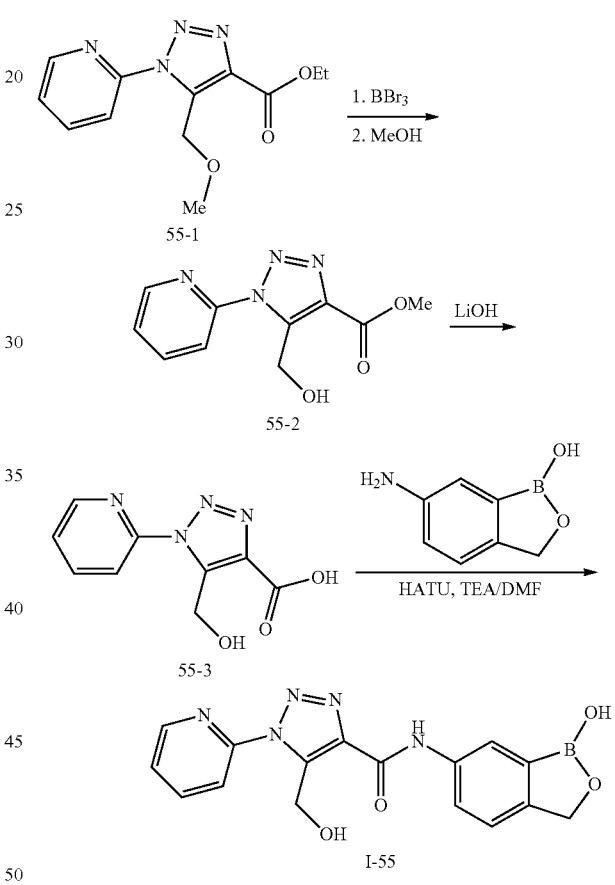

Step 1

BBr$_3$ (15.14 g, 60.42 mmol, 5.82 mL, 3 equiv.) was added to a solution of ethyl 5-(methoxymethyl)-1-(pyridin-2-yl)-1H-1,2,3-triazole-4-carboxylate (55-1) (5.00 g, 20.14 mmol, 1 equiv.) (Prepared via General Method 5) in DCM (15.00 mL) at −78° C. The mixture was stirred at −78° C. for half an hour and warmed to room temperature. TLC showed one new large polarity spot was detected. The reaction was quenched by addition of MeOH until the solution turned clear. The mixture was treated with water (150 mL) and DCM (50 mL), and the pH was adjusted to pH=8 with NaHCO$_3$ aqueous solution. The aqueous solution was extracted with DCM (4×50 mL). The combined organic phases were dried over Na$_2$SO$_4$ and concentrated in vacuo. Methyl 5-(hydroxymethyl)-1-(pyridin-2-yl)-1H-1,2,3-triazole-4-carboxylate (55-2) (3.20 g, 13.66 mmol, 67.84% yield) was obtained as a white solid. $^1$H NMR (400 MHz DMSO-$d_6$): δ 8.69 (dd, J=0.8, 4.8 Hz, 1H), 8.18 (td, J=7.6, 1.6 Hz, 1H), 7.96 (d, J=8.0 Hz, 1H), 7.69-7.66 (m, 1H), 5.35 (t, J=6.0 Hz, 1H), 5.06 (d, J=6.0 Hz, 2H), 3.91 (s, 3H) ppm.

Step 2

LiOH.H$_2$O (268.12 mg, 6.39 mmol, 3 equiv.) was added to a solution of methyl 5-(hydroxymethyl)-1-(pyridin-2-yl)-1H-1,2,3-triazole-4-carboxylate (55-2) (500.00 mg, 2.13 mmol, 1 equiv.) in H$_2$O (10.00 mL) and MeOH (10.00 mL) at 20° C., and the mixture was stirred for 12 h. TLC showed that the reaction was complete. Methanol was evaporated, and the pH was adjusted to less than 4 with 2N HCl aqueous solution. A white precipitate was collected by filtration to give 5-(hydroxymethyl)-1-(2-pyridyl) triazole-4-carboxylic acid (55-3) (270.00 mg, 1.23 mmol, 57.57% yield). $^1$H NMR (400 MHz DMSO-$d_6$): δ 8.69 (dd, J=1.6, 4.8 Hz, 1H), 8.18 (td, J=8.0, 2.0 Hz 1H), 7.96 (d, J=8.0 Hz, 1H), 7.68-7.65 (m, 1H), 5.08 (s, 2H) ppm.

Step 3

HATU (466.24 mg, 1.23 mmol, 1 equiv.) was added to a solution of 6-aminobenzo[c][1,2]oxaborol-1(3H)-ol (182.64 mg, 1.23 mmol, 1 equiv.), 5-(hydroxymethyl)-1-(pyridin-2-yl)-1H-1,2,3-triazole-4-carboxylic acid (55-3) (270.00 mg, 1.23 mmol, 1 equiv.) and TEA (372.60 mg, 3.68 mmol, 509.92 uL, 3 equiv.) in DMF (15.00 mL). The mixture was stirred at 20° C. for 3 h. LCMS showed the reaction was complete. The reaction was quenched by addition of water (50 mL). The resultant white precipitate was filtered to give the crude product. The crude product was refluxed in CH$_3$CN (50 mL) for 2 h. The mixture was filtered to give I-55 (53 mg). The filtrate was concentrated and purified by prep-HPLC to give I-55 (68 mg). N-(1-hydroxy-1,3-dihydrobenzo[c][1,2]oxaborol-6-yl)-5-(hydroxymethyl)-1-(pyridin-2-yl)-1H-1,2,3-triazole-4-carboxamide (121.0 mg, 335.3 umol, 27.3% yield) was obtained as a light yellow solid. $^1$H NMR: (400 MHz DMSO-$d_6$): δ 10.73 (s, 1H), 9.25 (s, 1H), 8.71 (d, J=4 Hz, 1H), 8.26 (s, 1H), 8.20 (t, J=7.0 Hz, 1H), 7.99 (d, J=8.0 Hz, 1H), 7.83 (d, J=8 Hz, 1H), 7.69-7.66 (m, 1H), 7.40 (d, J=8.0 Hz, 1H), 5.46 (t, J=6.0 Hz, 1H), 5.16 (d, J=6.0 Hz, 2H), 4.98 (s, 2H); MS (ESI+): m/z=352.1 [M+H]$^+$. HPLC purity: 97.3% in 220 nm; 97.0% in 254 nm.

Example 56. N-(1-hydroxy-1,3-dihydrobenzo[c][1,2]oxaborol-6-yl)-1-(pyridin-2-yl)-5-(2,2,2-trifluoroethyl)-1H-1,2,3-triazole-4-carboxamide (I-56)

This compound was synthesized using the following scheme:

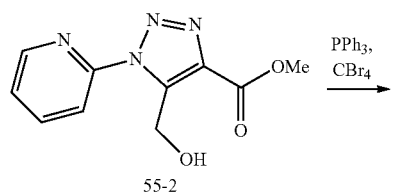

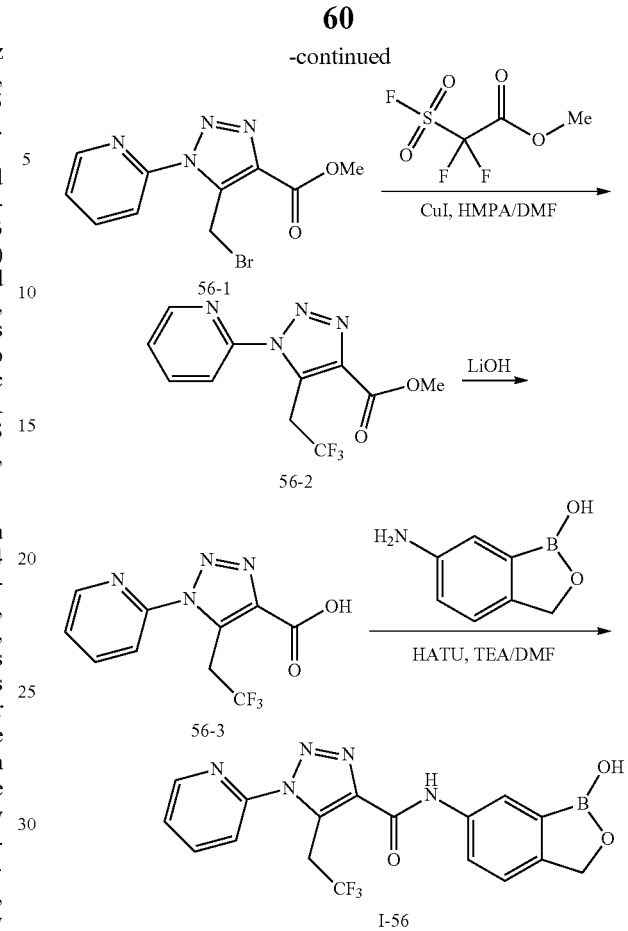

Step 1

PPh$_3$ (2.02 g, 7.69 mmol, 1.80 equiv.) was added to a mixture of methyl 5-(hydroxymethyl)-1-(pyridin-2-yl)-1H-1,2,3-triazole-4-carboxylate (55-2) (1.00 g, 4.27 mmol, 1 equiv.), which can be prepared by the method described in example 55 and CBr$_4$ (1.49 g, 4.48 mmol, 1.05 equiv.) in DCM (30.00 mL) at 0° C., and the mixture was stirred at 20° C. for 12 h. The reaction was quenched with water (100 mL), and extracted with DCM (2×30 mL). The combined organic phase was dried over Na$_2$SO$_4$ and concentrated in vacuo. The residue was purified by flash column chromatography (SiO$_2$, petroleum ether/EtOAc=3/1). Methyl 5-(bromomethyl)-1-(pyridin-2-yl)-1H-1,2,3-triazole-4-carboxylate (56-1) (1.1 g, 3.7 mmol, 86.7% yield) was obtained as white solid. $^1$H NMR (400 MHz DMSO-$d_6$): δ 8.69 (dd, J=1.2 & 4.8 Hz, 1H), 8.10 (d, J=8.0 Hz, 1H), 8.00 (td, J=8.4 & 2.0 Hz, 1H), 7.49 (dd, J=4.8 & 6.4 Hz, 1H), 5.49 (s, 2H), 4.05 (s, 3H) ppm.

Step 2

Methyl 5-(bromomethyl)-1-(pyridin-2-yl)-1H-1,2,3-triazole-4-carboxylate (56-1) (1.16 g, 3.90 mmol, 1 equiv.), CuI (1.49 g, 7.80 mmol, 2 equiv.), HMPA (3.49 g, 19.50 mmol, 3.43 mL, 5 equiv.) and methyl 2,2-difluoro-2-(fluorosulfonyl)acetate (3.75 g, 19.50 mmol, 2.48 mL, 5 equiv.) in DMF (50.00 mL) were stirred at 80-90° C. for 12 h. The reaction was quenched by addition of water (100 mL), and the aqueous solution was extracted with DCM (2×50 mL). The combined organic phase was dried over Na$_2$SO$_4$ and concentrated in vacuo. The residue was purified by flash column chromatography (SiO$_2$, petroleum ether/EtOAc=3/1) to give methyl 1-(pyridin-2-yl)-5-(2,2,2-trifluoroethyl)-1H-1,2,3- triazole-4-carboxylate (56-2) (860.0 mg, 3.00 mmol, 77.1% yield) as a white solid. ¹H NMR (400 MHz CDCl₃): δ 8.58 (dd, J=0.8 & 4.8 Hz, 1H), 8.05 (d, J=8.4 Hz, 1H), 8.02 (td, J=7.2 & 2.0 Hz, 1H), 7.49-7.46 (m, 1H), 4.82 (q, J=10.0 Hz, 2H), 4.04 (s, 3H) ppm.

Steps 3 and 4

The subsequent hydrolysis and amidation reactions were conducted as described in steps 2 and 3 of Example 55. The title compound, N-(1-hydroxy-1,3-dihydrobenzo[c][1,2]oxaborol-6-yl)-1-(pyridin-2-yl)-5-(2,2,2-trifluoroethyl)-1H-1,2,3-triazole-4-carboxamide (56-1), was obtained as a yellowish solid (768.0 mg, 1.90 mmol, 83.2% yield, 99.6% purity). ¹H NMR (400 MHz DMSO-d₆): δ 10.80 (s, 1H), 9.24 (s, 1H), 8.72 (dd, J=3.6 & 0.9 Hz, 1H), 8.30 (d, J=1.6 Hz, 1H), 8.23 (td, J=7.2 & 2.0 Hz, 1H), 8.08 (d, J=8.0 Hz, 1H), 7.82 (dd, J=8.4 & 2.0 Hz, 1H), 7.71-7.65 (m, 1H), 7.40 (d, J=8.0 Hz, 1H), 4.98 (s, 2H), 4.80 (q, J=10.4 Hz, 2H) ppm. MS (ESI+): m/z=404.1 [M+H]⁺. HPLC: 97.7% in 220 nm and 97.9% in 254 nm.

Example 57. N-(1-hydroxy-1,3-dihydrobenzo[c][1,2]oxaborol-6-yl)-1-(6-methyl pyridin-2-yl)-1H-1,2,3-triazole-4-carboxamide (I-57)

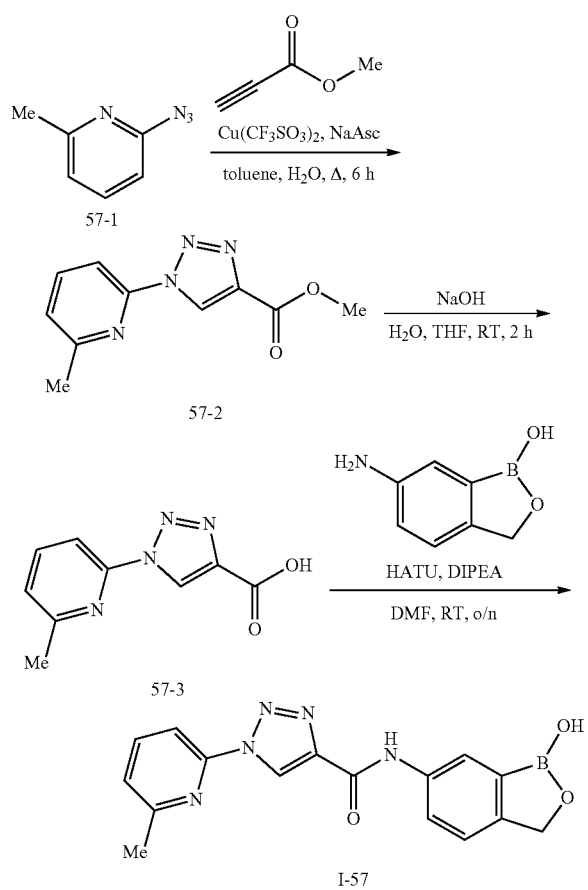

Step 1

To a suspension of commercially-available 57-1 (200 mg, 1 equiv.) in toluene (10 mL) and H₂O (0.1 mL) was added Cu(CF₃SO₃)₂ (108 mg, 0.2 equiv.), NaAsc (89 mg, 0.3 equiv.) and methyl propiolate (176 mg, 1.2 equiv.). The mixture was heated to reflux and stirred for 6 h. The mixture was concentrated and purified by column to get 370 mg of 57-2.

Step 2

To a solution of 57-2 (370 mg, 1 equiv.) in THF (4 mL) and H₂O (1 mL) was added LiOH (72 mg, 2.0 equiv.). The mixture was stirred at room temperature for 2 h. The reaction was completed. The pH was adjusted to 3 with 3 M HCl. The mixture was extracted with EtOAc (5 mL*2). The combined organic layer was dried over Na₂SO₄, filtered and concentrated to get 240 mg of 57-3.

Step 3

To a solution of 57-3 (150 mg, 1 equiv.) in DMF (5 mL) was added HATU (390 mg, 1.5 equiv.), DIPEA (175 mg, 2 equiv.) and 6-aminobenzo[c][1,2]oxaborol-1(3H)-ol (122 mg, 1.2 equiv.). The mixture was stirred at room temperature for 16 h. Then the mixture was purified by prep-HPLC to get 88 mg of I-57 as a yellow solid. ¹H NMR (400 MHz, DMSO-d₆) δ 10.60 (s, 1H), 9.35 (s, 1H), 9.32 (s, 1H), 8.24 (d, J=1.6 Hz, 1H), 8.09-8.02 (m, 1H), 8.02-7.96 (m, 1H), 7.83 (dd, J=8.2, 1.9 Hz, 1H), 7.49 (d, J=7.6 Hz, 1H), 7.41 (d, J=8.0 Hz, 1H), 4.98 (s, 2H), 2.60 (s, 3H).

Example 58. 1-(3-Chloropyridin-2-yl)-N-(1-hydroxy-1,3-dihydrobenzo[c][1,2]oxaborol-6-yl)-1H-1,2,3-triazole-4-carboxamide (I-58)

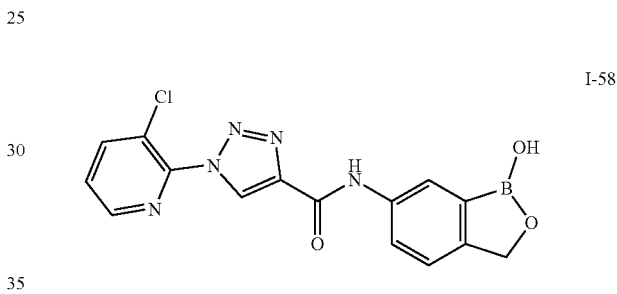

This compound was prepared in a similar way to Example 57 using 1-(3-chloro pyridin-2-yl)-1H-1,2,3-triazole-4-carboxylic acid (Prepared via General Method 4) in place of 1-(6-methylpyridin-2-yl)-1H-1,2,3-triazole-4-carboxylic acid, ¹H NMR (400 MHz, DMSO-d₆) δ 10.70 (s, 1H), 9.28-9.24 (m, 2H), 8.70 (dd, J=4.6, 1.4 Hz, 1H), 8.41 (dd, J=8.2, 1.4 Hz, 1H), 8.24 (d, J=1.5 Hz, 1H), 7.91-7.74 (m, 2H), 7.41 (d, J=8.3 Hz, 1H), 4.99 (s, 2H).

Example 59. 1-(5-Chloropyridin-2-yl)-N-(1-hydroxy-1,3-dihydrobenzo[c][1,2]oxaborol-6-yl)-1H-1,2,3-triazole-4-carboxamide (I-59)

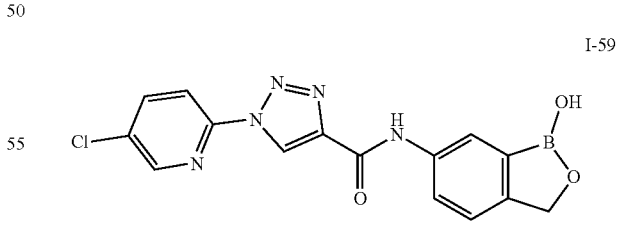

This compound was prepared in a similar way to Example 57 using 1-(5-chloropyridin-2-yl)-1H-1, 2, 3-triazole-4-carboxylic acid (Prepared via General Method 4) in place of 1-(6-methylpyridin-2-yl)-1H-1,2,3-triazole-4-carboxylic acid. ¹H NMR (400 MHz, DMSO-d₆) δ 10.60 (s, 1H), 9.37 (s, 1H), 9.28 (s, 1H), 8.74 (d, J=2.4 Hz, 1H), 8.30-8.28 (m, 1H), 8.23-8.21 (m, 2H), 7.82 (dd, J=8.3, 1.8 Hz, 1H), 7.40 (d, J=8.0 Hz, 1H), 4.98 (s, 2H).

Example 60. 1-(4-Fluorophenyl)-N-(1-hydroxy-1,3-dihydrobenzo[c][1,2]oxaborol-6-yl)-1H-1,2,3-triazole-4-carboxamide (I-60)

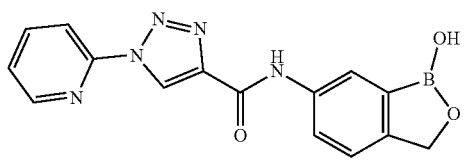

I-61

This compound was prepared in a similar way to Example 57 using 1-(4-fluoro phenyl)-1H-1,2,3-triazole-4-carboxylic acid (Prepared via General Method 1) in place of 1-(6-methylpyridin-2-yl)-1H-1,2,3-triazole-4-carboxylic acid, $^1$H NMR (400 MHz, DMSO-$d_6$) δ 10.63 (s, 1H), 9.44 (s, 1H), 9.27 (s, 1H), 8.23 (d, J=1.6 Hz, 1H), 8.08-8.05 (m, 2H), 7.82 (s, 1H), 7.50 (t, J=8.8 Hz, 2H), 7.40 (d, J=8.0 Hz, 1H), 4.98 (s, 2H).

Example 61. N-(1-hydroxy-1,3-dihydrobenzo[c][1,2]oxaborol-6-yl)-1-(pyridin-2-yl)-1H-1,2,3-triazole-4-carboxamide (I-61)

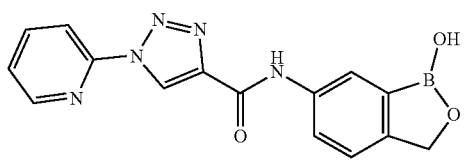

I-61

This compound was prepared in a similar way to Example 57 using 1-(pyridin-2-yl)-1H-1,2,3-triazole-4-carboxylic acid (Prepared via General Method 4) in place of 1-(6-methylpyridin-2-yl)-1H-1,2,3-triazole-4-carboxylic acid. $^1$H NMR (400 MHz, DMSO-$d_6$) δ 10.61 (s, 1H), 9.39 (s, 1H), 9.27 (s, 1H), 8.68 (d, J=4.4 Hz, 1H), 8.24-8.18 (m, 3H), 7.83-7.81 (m, 1H), 7.63 (ddd, J=6.7, 4.9, 1.7 Hz, 1H), 7.41 (d, J=8.4 Hz, 1H), 4.98 (s, 2H).

Example 62. N-(1-hydroxy-3,3-dimethyl-1,3-dihydrobenzo[c][1,2]oxaborol-6-yl)-1-(pyridin-2-yl)-1H-1,2,3-triazole-4-carboxamide (I-62)

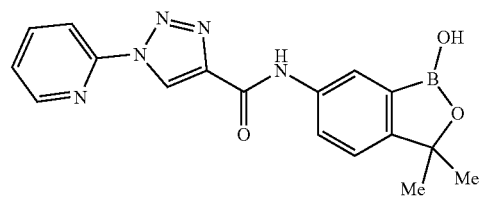

I-62

This compound was prepared in a similar way to Example 57 using 1-(pyridin-2-yl)-1H-1,2,3-triazole-4-carboxylic acid (Prepared via General Method 4) in place of 1-(6-methylpyridin-2-yl)-1H-1,2,3-triazole-4-carboxylic acid and amino CBO4 in place of 6-aminobenzo[c][1,2]oxaborol-1 (3H)-ol. $^1$H NMR (400 MHz, DMSO-$d_6$) δ 10.60 (s, 1H), 9.38 (s, 1H), 9.12 (s, 1H), 8.67 (d, J=5.2 Hz, 1H), 8.20-8.18 (m, 1H), 8.13 (d, J=1.6 Hz, 1H), 7.81-7.80 (m, 1H), 7.78-7.63 (m, 1H), 7.64 (d, J=4.8 Hz, 1H), 7.41 (d, J=8.4 Hz, 1H), 1.45 (s, 6H).

Example 63. N-(1-hydroxy-1,3-dihydrobenzo[c][1,2]oxaborol-6-yl)-1-(pyridin-3-yl)-1H-1,2,3-triazole-4-carboxamide (I-63)

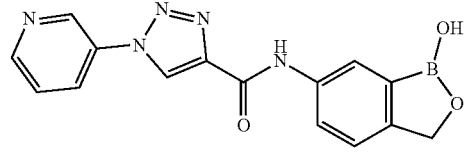

I-63

This compound was prepared in a similar way to Example 57 using 1-(pyridin-3-yl)-1H-1,2,3-triazole-4-carboxylic acid (Prepared via General Method 6) in place of 1-(6-methylpyridin-2-yl)-1H-1,2,3-triazole-4-carboxylic acid. $^1$H NMR (400 MHz, DMSO-$d_6$) δ 10.66 (s, 1H), 9.55 (s, 1H), 9.26-9.24 (m, 2H), 8.76 (dd, J=4.8, 0.8 Hz, 1H), 8.25 (d, J=1.5 Hz, 1H), 7.84 (dd, J=8.4, 2.0 Hz, 1H), 7.71 (dd, J=8.4, 4.8 Hz, 1H), 7.41 (d, J=8.4 Hz, 1H), 4.99 (s, 2H).

Example 64. N-(1-hydroxy-1,3-dihydrobenzo[c][12]oxaborol-6-yl)-1-(6-methoxypyridine-2-yl)-1H-1,2,3-triazole-4-carboxamide (I-64)

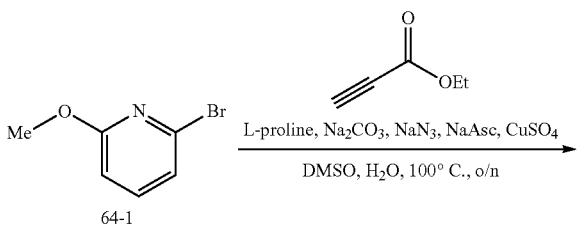

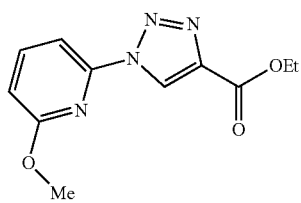 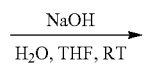

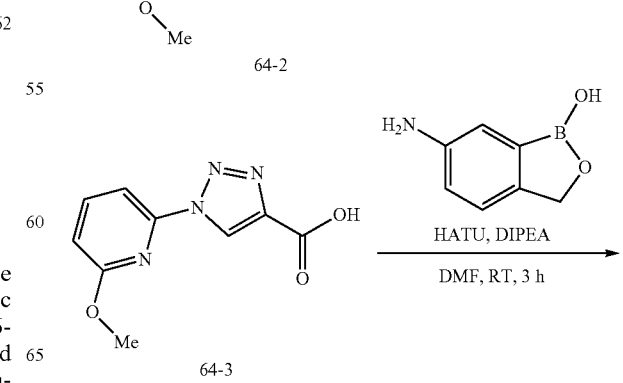

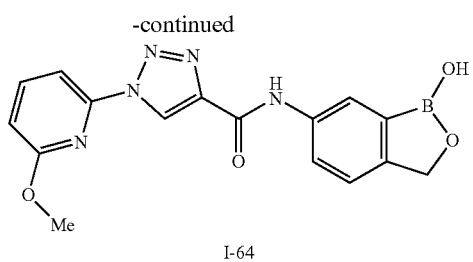

I-64

Step 1

To a solution of 64-1 (5.0 g, 1 equiv.) and ethyl propiolate (2.6 g, 1 equiv.) in DMSO (60 mL) and H₂O (7 mL) was added L-proline (635 mg, 0.2 equiv.), Na₂CO₃ (585 mg, 0.2 equiv.), NaN₃ (2.1 g, 1.2 equiv.), NaAsc (525 mg, 0.1 equiv.) and CuSO₄·5H₂O (330 mg, 0.05 equiv.). The mixture was stirred at 100° C. for 16 h. The reaction was completed. The mixture was cooled to room temperature and H₂O (120 mL) was added. The mixture was extracted with EtOAc (100 mL*2) and the combined organic layer was dried over Na₂SO₄, filtered, concentrated and purified by column to get 1.5 g of 64-2.

Step 2

64-3 was prepared in a similar way to Step 2 of Example 57 using ethyl 1-(6-methoxypyridin-2-yl)-1H-1,2,3-triazole-4-carboxylate in place of methyl 1-(6-methylpyridin-2-yl)-1H-1,2,3-triazole-4-carboxylate.

Step 3

I-64 was prepared in a similar way to Step 3 of Example 57 using 1-(6-methoxy pyridin-2-yl)-1H-1,2,3-triazole-4-carboxylic acid in place of 1-(6-methylpyridin-2-yl)-1H-1,2,3-triazole-4-carboxylic acid. ¹H NMR (400 MHz, DMSO-d₆) δ 10.63 (s, 1H), 9.39 (s, 1H), 9.30 (s, 1H), 8.22 (s, 1H), 8.05 (t, J=8.0 Hz, 1H), 7.84 (dd, J=8.0, 1.8 Hz, 1H), 7.76 (d, J=7.7 Hz, 1H), 7.41 (d, J=8.2 Hz, 1H), 7.03 (d, J=8.4 Hz, 1H), 4.99 (s, 2H), 4.03 (s, 3H).

Example 65. N-(1-hydroxy-1,3-dihydrobenzo[c][1,2]oxaborol-6-yl)-1-(6-methoxypyridin-2-yl)-5-methyl-1H-1,2,3-triazole-4-carboxamide (I-65)

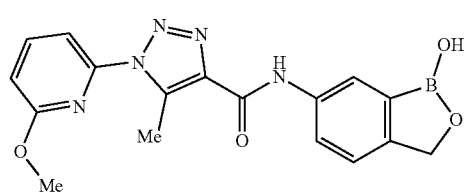

I-65

This compound was prepared in a similar way to Example 64 using 1-(6-methoxypyridin-2-yl)-5-methyl-1H-1,2,3-triazole-4-carboxylic acid (Prepared via General Method 5) in place of 1-(6-methoxypyridin-2-yl)-1H-1,2,3-triazole-4-carboxylic acid. ¹H NMR (400 MHz, DMSO-d6) δ 10.56 (s, 1H), 9.24 (s, 1H), 8.28 (d, J=1.5 Hz, 1H), 8.06 (t, J=7.9 Hz, 1H), 7.83 (dd, J=8.3, 2.0 Hz, 1H), 7.58 (d, J=7.4 Hz, 1H), 7.39 (d, J=8.3 Hz, 1H), 7.08 (d, J=8.2 Hz, 1H), 4.98 (s, 2H), 3.95 (s, 3H), 2.91 (s, 3H).

Example 66. N-(1-hydroxy-1,3-dihydrobenzo[c][1,2]oxaborol-6-yl)-1-phenyl-1H-1,2,3-triazole-4-carboxamide (I-66)

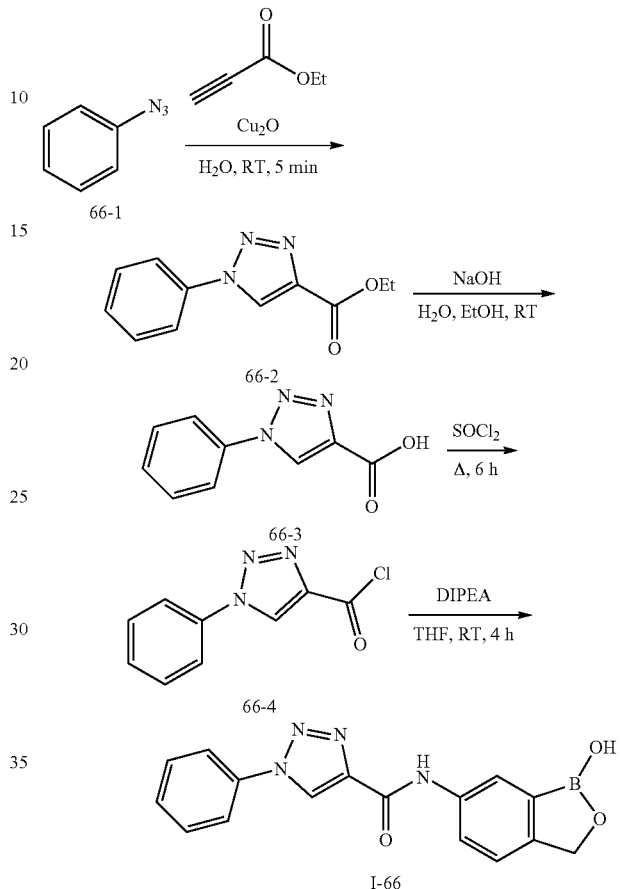

Step 1

To a suspension of 66-1 (687 mg, 1 equiv.) in H₂O (5.7 mL) was added ethyl propiolate (679 mg, 1.2 equiv.) and Cu₂O (82.6 mg, 0.1 equiv.) under N₂. The solution was stirred at room temperature for 5 minutes. The reaction was completed and NH₃·H₂O (10 mL, 30%) was added. The mixture was extracted with EtOAc (30 mL*4) and the combined organic phase was washed with water, brine, dried over Na₂SO₄, filtered, concentrated and purified by column to get 1.1 g of 66-2.

Step 2

66-3 was prepared in a similar way to Example 57 using ethyl 1-phenyl-1H-1,2,3-triazole-4-carboxylate in place of methyl 1-(6-methylpyridin-2-yl)-1H-1,2,3-triazole-4-carboxylate.

Step 3

A suspension of 66-3 (300 mg) in SOCl₂ (30 mL) was stirred at refluxing for 6 h. The reaction was completed. The mixture was concentrated at reduced pressure to get 350 mg of crude 66-4.

Step 4

To a solution of 6-aminobenzo[c][1,2]oxaborol-1(3H)-ol (237 mg, 1 equiv.) and DIPEA (410 mg, 2 equiv.) in THF (10 mL) was added a solution of 66-4 (355 mg, 1 equiv.) in THF (3 mL) dropwise. The reaction suspension was stirred at room temperature for 4 h. The solvent was removed and purified by prep-HPLC get 270 mg of I-66 as a white solid, $^1$H NMR (400 MHz, DMSO-$d_6$) δ 10.63 (s, 1H), 9.46 (s, 1H), 9.27 (s, 1H), 8.24 (s, 1H), 8.02 (d, J=7.6 Hz, 2H), 7.84 (d, J=8.4 Hz 1H), 7.66-7.62 (m, 2H), 7.39-7.55 (m, 1H), 4.98 (s, 2H).

Example 67. 1-(2-Fluorophenyl)-N-(1-hydroxy-1,3-dihydrobenzo[c][1,2]oxaborol-6-yl)-5-(trifluoromethyl)-1H-1,2,3-triazole-4-carboxamide (I-67)

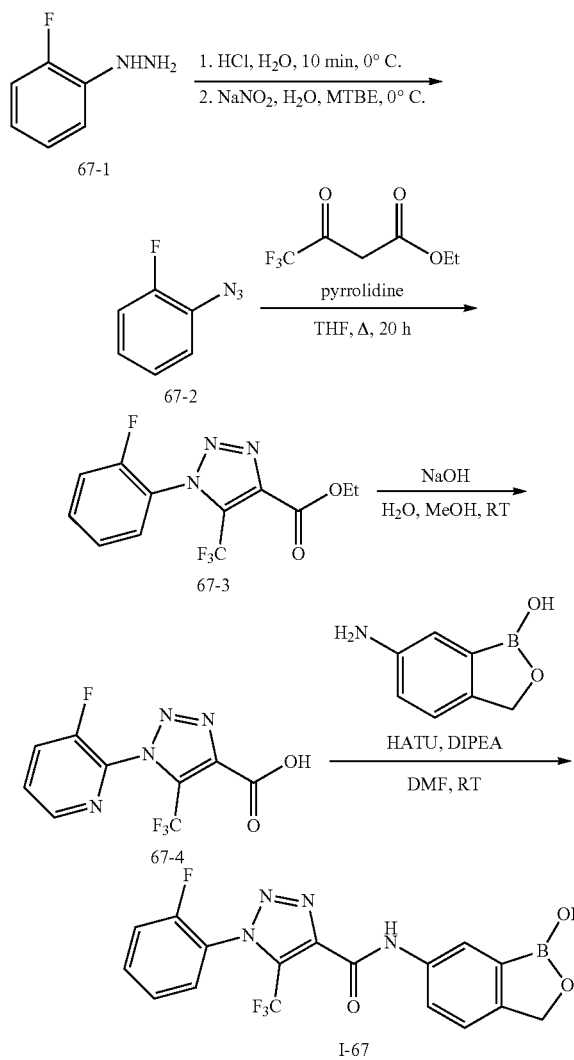

Step 1

67-1 (5.0 g, 1 equiv.) was added in portions to a cold solution of concentrated hydrochloric acid (50.0 mL) over a period of 10 min at 0° C. MTBE (25.0 mL) was added, followed by the dropwise addition of a solution of sodium nitrite (2.7 g, 1.3 equiv.) in water (10.0 mL) and kept the temperature below 5° C. The reaction was stirred at 0° C. for 3 h and then extracted with EtOAc (100 mL*5). The organic layer was washed with water and brine, dried over $Na_2SO_4$ and carefully evaporated in vacuo to get 3.0 g of 67-2.

Step 2

To a solution of 67-2 (3.0 g, 1 equiv.) in THF (50.0 mL) was added ethyl 4,4,4-trifluoro-3-oxobutanoate (4.0 g, 1 equiv.) and pyrrolidine (1.6 g, 1 equiv.) under nitrogen. The reaction mixture was heated to reflux and stirred for 20 h. The reaction was monitored by TLC. The reaction mixture was concentrated and purified by silica gel chromatography to get 3.0 g of 67-3.

Step 3

To a solution of 67-3 (3.0 g, 1 equiv.) in MeOH (20.0 mL) was added sodium hydroxide aqueous solution (10 mL, 4 M, 4 equiv.). The reaction mixture was stirred at room temperature for 2 h. The solvent was evaporated to remove MeOH and then the pH was adjusted to 3 with 2 M hydrochloric acid. The white solid was separated out and the solid was filtered and dried in vacuo to get 800 mg of 67-4.

Step 4

A solution of 67-4 (200 mg, 1 equiv.), 6-aminobenzo[c][1,2]oxaborol-1(3H)-ol (107 mg, 1 equiv.), HATU (410 mg, 1 equiv.) and DIPEA (180 mg, 2 equiv.) in DMF (8 mL) was stirred at room temperature for 16 h. The reaction was completed. The mixture was purified by prep-HPLC to get 93 mg of I-67 as white solid. $^1$H NMR (400 MHz, DMSO-$d_6$) δ 11.06 (s, 1H), 9.29 (s, 1H), 8.31-8.26 (m, 1H), 7.96-7.89 (m, 1H), 7.85-7.75 (m, 2H), 7.71-7.62 (m, 1H), 7.60-7.51 (m, 1H), 7.43 (d, J=8.0 Hz, 1H), 4.99 (s, 2H).

Example 68. N-(1-hydroxy-1,3-dihydrobenzo[c][1,2]oxaborol-6-yl)-1-phenyl-5-(trifluoromethyl)-1H-1,2,3-triazole-4-carboxamide (I-68)

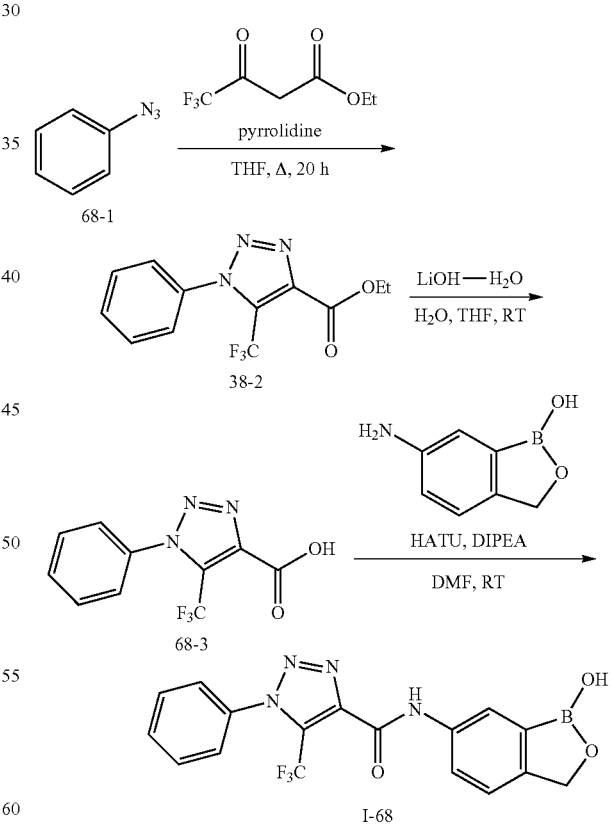

Step 1

To a solution of 68-1 (560 mg, 1 equiv.) in THF (50.0 mL) was added ethyl 4,4,4-trifluoro-3-oxobutanoate (865 mg, 1 equiv.) and pyrrolidine (334 mg, 1 equiv.) under nitrogen. The reaction mixture was heated to reflux and stirred for 20 h. The reaction was monitored by TLC. The reaction mixture was concentrated and purified by silica gel chromatography to give 720 mg of 68-2.

Step 2

To a solution of 68-2 (720 mg, 1 equiv.) in THF (5 mL) and water (5 mL) was added lithium hydroxide monohydrate (424 mg, 4 equiv.). The reaction mixture was stirred at room temperature for 2 h. The solvent was evaporated to remove THF and then the pH was adjusted to 3 with 2 M hydrochloric acid. The white solid was separated out and the solid was filtered and dried in vacuo to get 604 mg of 68-3.

Step 3

A solution of 68-3 (250 mg, 1 equiv.), 6-aminobenzo[c][1,2]oxaborol-1(3H)-ol (145 mg, 1 equiv.), HATU (370 mg, 1 equiv.) and DIPEA (252 mg, 2 equiv.) in DMF (8 mL) was stirred at room temperature for 16 h. The reaction was completed. The mixture was purified by prep-HPLC to get 207 mg of I-68 as white solid. $^1$H NMR (400 MHz, DMSO-$d_6$) δ 11.02 (s, 1H), 9.29 (s, 1H), 8.32-8.22 (m, 1H), 7.78 (dd, J=6.4, 4.8 Hz, 1H), 7.76-7.63 (m, 5H), 7.42 (d, J=8.0 Hz, 1H), 4.99 (s, 2H).

Example 69. 1-(3-Fluorophenyl)-N-(1-hydroxy-1,3-dihydrobenzo[c][1,2]oxaborol-6-yl)-5-(trifluoromethyl)-1H-1,2,3-triazole-4-carboxamide (I-69)

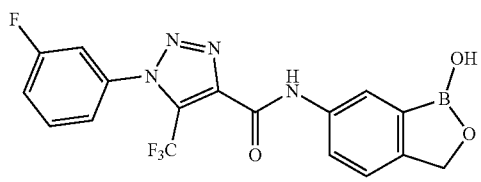

I-69

This compound was prepared in a similar way to Example 67 using 1-(3-fluorophenyl)-5-(trifluoromethyl)-1H-1,2,3-triazole-4-carboxylic acid (Prepared via General Method 2) in place of 1-(2-fluorophenyl)-5-(trifluoromethyl)-1H-1,2,3-triazole-4-carboxylic acid. $^1$H NMR (400 MHz, DMSO-$d_6$) δ 11.03 (s, 1H), 9.29 (s, 1H), 8.31-8.26 (m, 1H), 7.85-7.72 (m, 3H), 7.69-7.53 (m, 2H), 7.43 (d, J=8.0 Hz, 1H), 4.99 (s, 2H).

Example 70. 1-(4-Fluorophenyl)-N-(1-hydroxy-1,3-dihydrobenzo[c][1,2]oxaborol-6-yl)-5-(trifluoromethyl)-1H-1,2,3-triazole-4-carboxamide (I-70)

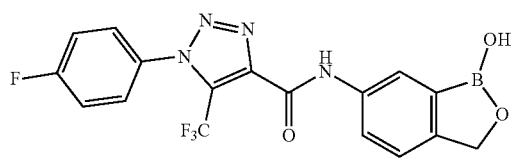

I-70

This compound was prepared in a similar way to Example 67 using 1-(4-fluorophenyl)-5-(trifluoromethyl)-1H-1,2,3-triazole-4-carboxylic acid (Prepared via General Method 2) in place of 1-(2-fluorophenyl)-5-(trifluoromethyl)-1H-1,2,3-triazole-4-carboxylic acid. $^1$H NMR (400 MHz, DMSO-$d_6$) δ 11.00 (s, 1H), 9.28 (s, 1H), 8.31-8.25 (m, 1H), 7.85-7.73 (m, 3H), 7.61-7.52 (m, 2H), 7.45-7.40 (m, 1H), 4.99 (s, 2H).

Example 71. N-(1-hydroxy-1,3-dihydrobenzo[c][1,2]oxaborol-6-yl)-1-(pyridin-3-yl)-5-(trifluoromethyl)-1H-1,2,3-triazole-4-carboxamide (I-71)

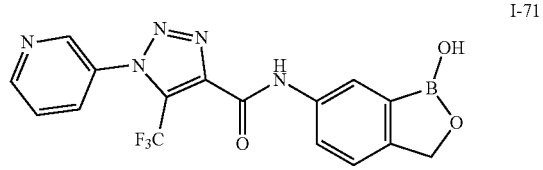 [SMILES: O=C(Nc1ccc2c(c1)B(O)OC2)c1nnn(-c2cccnc2)c1C(F)(F)F]

I-71

This compound was prepared in a similar way to Example 67 using 1-(pyridin-3-yl)-5-(trifluoromethyl)-1H-1,2,3-triazole-4-carboxylic acid in place of 1-(2-fluorophenyl)-5-(trifluoromethyl)-1H-1,2,3-triazole-4-carboxylic acid, $^1$H NMR (400 MHz, DMSO-$d_6$) δ 11.06 (s, 1H), 9.29 (s, 1H), 9.03-8.96 (m, 1H), 8.95-8.88 (m, 3H), 7.61-7.52 (m, 2H), 7.45-7.40 (m, 1H), 4.99 (s, 2H).

Example 72. N-(1-hydroxy-1,3-dihydrobenzo[c][1,2]oxaborol-6-yl)-5-methyl-2-phenyl-2H-1,2,3-triazole-4-carboxamide (I-72)

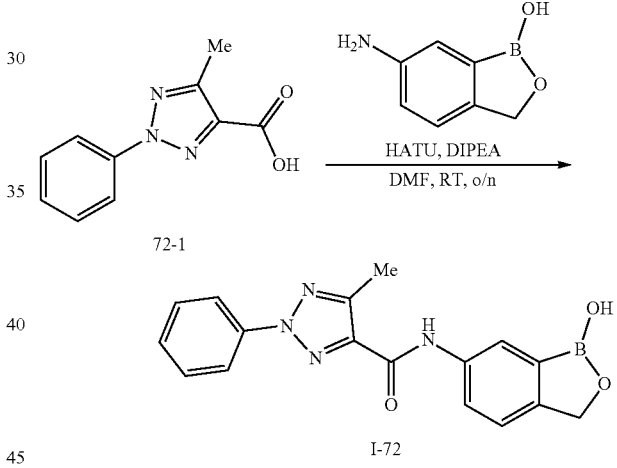

This compound was prepared in a similar way to the last step of Example 57 using 6-aminobenzo[c][1,2]oxaborol-1(3H)-ol in place of 1-(6-methylpyridin-2-yl)-1H-1,2,3-triazole-4-carboxylic acid. $^1$H NMR (400 MHz, DMSO-$d_6$) δ 10.43 (s, 1H), 9.25 (s, 1H), 8.25 (d, J=1.6 Hz, 1H), 8.17-8.09 (m, 2H), 7.80 (dd, J=7.6, 2.0 Hz, 1H), 7.68-7.57 (m, 2H), 7.52-7.44 (m, 1H), 7.42 (d, J=8.4 Hz, 1H), 4.99 (s, 2H).

Example 73. N-(1-hydroxy-1,3-dihydrobenzo[c][1,2]oxaborol-6-yl)-4-methyl-5-(pyridine-2-yl)-4H-1,2,4-triazole-3-carboxamide (I-73)

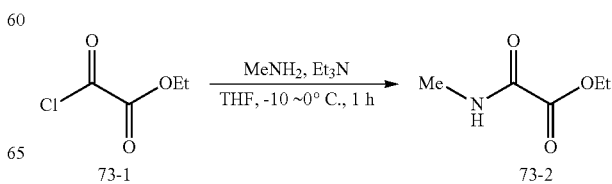

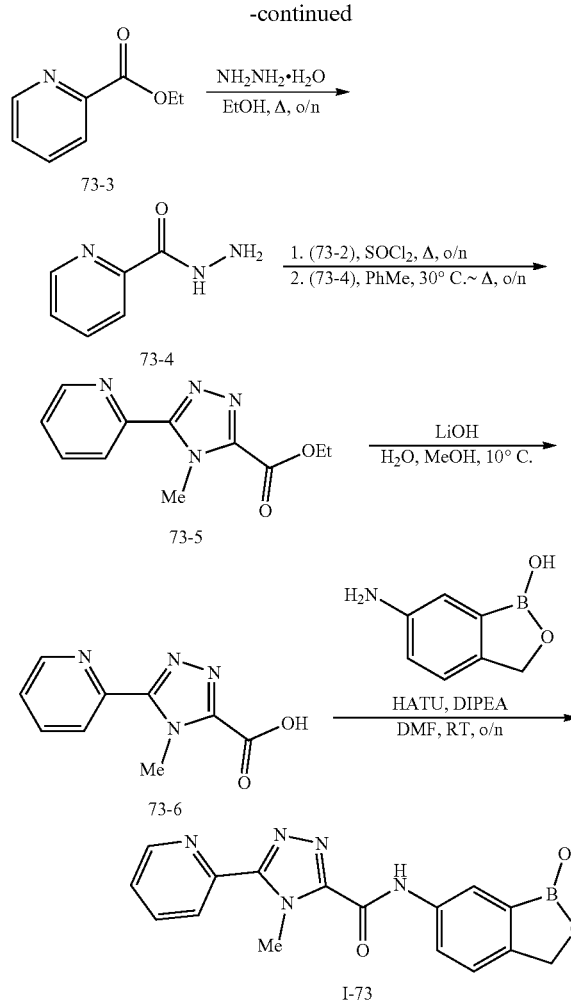

and the reaction mixture was stirred at 10° C. for 10 minutes. The pH of the reaction mixture was adjusted to 5 with 1 M HCl and lyophilized to give 150 mg of crude 73-6.

Step 5

To a solution of crude 73-6 (150 mg, 1 equiv.) in DMF (3 mL) was added HATU (114 mg, 1 equiv.), DIPEA (52 mg, 1.3 equiv.) and Amino-CBO-1 (45 mg, 1 equiv.). The reaction mixture was stirred at room temperature for 16 h. The reaction was completed and purified by prep-HPLC to get 15 mg of I-73 as white solid. $^1$H NMR (400 MHz, DMSO-$d_6$) δ 11.00 (s, 1H), 9.26 (s, 1H), 8.79 (d, J=4.8 Hz, 1H), 8.26 (s, 1H), 8.20 (d, J=8.0 Hz, 1H), 8.06 (td, J=7.6, 1.6 Hz, 1H), 7.84 (dd, J=8.2, 1.8 Hz, 1H), 7.60 (dd, J=7.2, 5.2 Hz, 1H), 7.42 (d, J=8.4 Hz, 1H), 4.99 (s, 2H), 4.28 (s, 3H).

Example 74. N-(1-hydroxy-1,3-dihydrobenzo[c][1,2]oxaborol-6-yl)-1-methyl-5-(6-methylpyridin-2-yl)-1H-1,2,4-triazole-3-carboxamide (I-74)

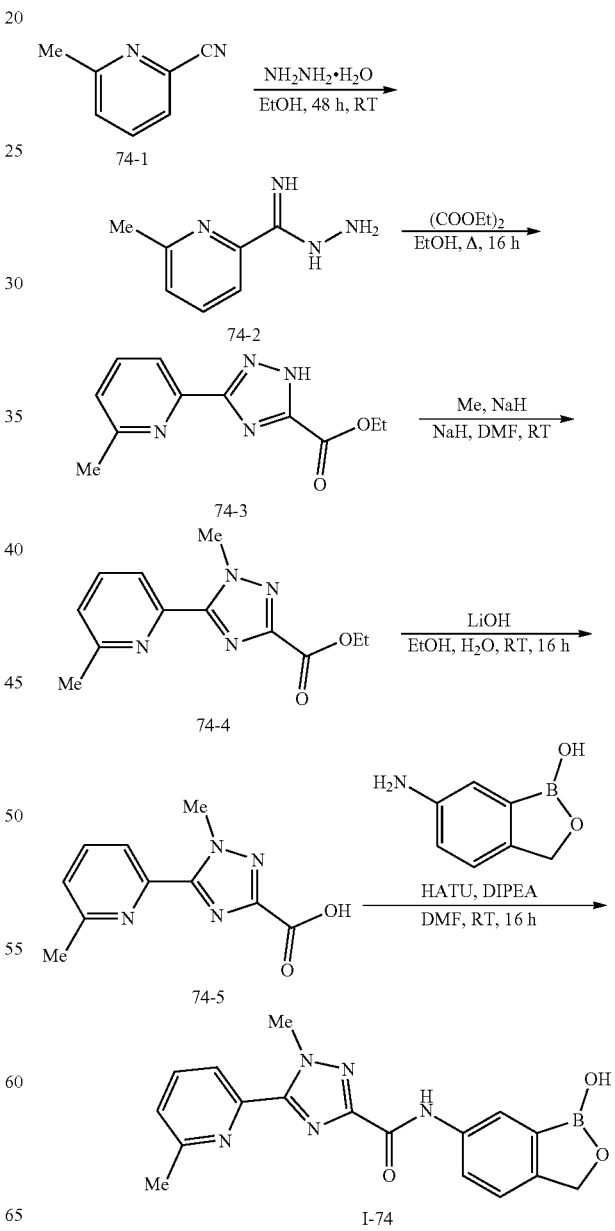

Step 1

To a solution of 73-1 (5.0 g, 1 equiv.) and TEA (7.7 mL, 1.5 equiv.) in THF (200 mL) was added MeNH$_2$ (20.1 mL, 2 M in THF, 1.1 equiv.) at −10° C. The reaction mixture warmed to 0° C. and was stirred at 0° C. for 1 h. The reaction was completed. The reaction was quenched by additional of water (10 mL), extracted with EtOAc (50 mL*2) and the organic layer was washed with 1 M HCl (100 mL), dried over Na$_2$SO$_4$ and concentrated to get 3.8 g of crude 73-2.

Step 2

To a solution of 73-3 (5.0 g, 1 equiv.) in EtOH (30 mL) was added NH$_2$NH$_2$.H$_2$O (2.5 g, 1.5 equiv.). Then the mixture was heated to reflux and stirred for 16 h. The reaction was completed. The reaction mixture was cooled to room temperature and concentrated to get 4.6 g of crude 73-4.

Step 3

A solution of 73-2 (500 mg, 1 equiv.) in SOCl$_2$ (10 mL) was heated to reflux and stirred for 16 h. The mixture was cooled to room temperature and concentrated under vacuum. To the residue was added toluene (10 mL) and 73-4 (520 mg, 1 equiv.) and the mixture was stirred at 30° C. for 2 h and then stirred at reflux for 16 h. The reaction was completed. The reaction mixture was cooled to room temperature, concentrated and purified by prep-TLC to get 90 mg of 73-5.

Step 4

To a solution of 73-5 (90 mg, 1 equiv.) in THF (4 mL) was added LiOH aqueous solution (0.52 mL, 2 M, 2.7 equiv.)

Step 1

To a solution of 74-1 (5 g, 1 equiv.) in EtOH (50 mL) was added NH$_2$NH$_2$·H$_2$O (6.36 g, 3 equiv.). The mixture was stirred at room temperature for 48 h. The solvent was removed in vacuum and the residue was purified by column to get 3.43 g of 74-2.

Step 2

To a solution of 74-2 (3.43 g, 1 equiv.) in EtOH (50 mL) was added diethyl oxalate (10 g, 3 equiv.). The reaction mixture was heated to reflux for 16 h. The solvent was removed in vacuum and the residue was purified by column to get 2.5 g of 74-3.

Step 3

To a suspension of NaH (0.45 g, 1.3 equiv.) in DMF (20 mL) was added a solution of 74-3 (2 g, 1 equiv.) in DMF (20 mL) dropwise at 0° C. The reaction mixture was stirred at 0° C. for 30 minutes, and then MeI (2.11 g, 1.7 equiv.) was added at this temperature. The reaction mixture was stirred at 0° C. for 30 minutes. The reaction was completed and the mixture was poured into saturated NH$_4$Cl aqueous solution (100 mL) and extracted with EtOAc (50 mL*3). The combined organic layers were washed with brine (50 mL), dried over Na$_2$SO$_4$ and concentrated in vacuum. The crude product was purified by flash column to get 870 mg of 74-4.

Step 4

To a solution of 74-4 (400 mg, 1 equiv.) in THF (20 mL) and H$_2$O (2 mL) was added LiOH (156 mg, 4 equiv.). The mixture was stirred at room temperature for 16 h. The solvent was concentrated in vacuum and the residue was dissolved in water (30 mL). The mixture was acidified with 3 M HCl and extracted with DCM (50 mL*5). The combined organic phase was dried over Na$_2$SO$_4$ and concentrated to get 370 mg of 74-5.

Step 5

To a solution of 74-5 (200 mg, 1 equiv.) in DMF (5 mL) was added 6-aminobenzo[c][1,2]oxaborol-1(3H)-ol (205 mg, 1.5 equiv.), DIPEA (474 mg, 4.0 equiv.) and HATU (697 mg, 2 equiv.). The mixture was stirred at room temperature for 16 h. The crude product was purified by prep-HPLC to get 126.5 mg of I-74 as a light red solid. $^1$H NMR (400 MHz, DMSO-d$_6$) δ 10.44 (s, 1H), 9.26 (s, 1H), 8.24 (s, 1H), 8.06 (d, J=8.0 Hz, 1H), 7.97-7.93 (t, J=8.0 Hz, 1H), 7.81-7.79 (m, 1H), 7.45 (d, J=7.6 Hz, 1H), 7.39 (d, J=7.6 Hz, 1H), 4.97 (s, 2H), 4.39 (s, 3H), 2.61 (s, 3H).

Example 75. N-(1-hydroxy-1,3-dihydrobenzo[c][1,2]oxaborol-6-yl)-5-(6-methoxypyridin-2-yl)-1-methyl-1H-1,2,4-triazole-3-carboxamide (I-75)

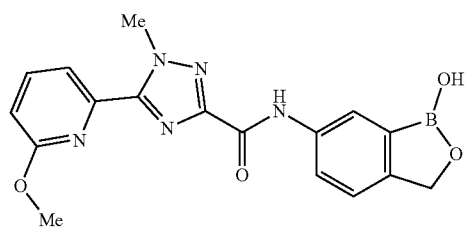

I-75

This compound was prepared in a similar way to Example 74 using 5-(6-methoxypyridin-2-yl)-1-methyl-1H-1,2,4-triazole-3-carboxylic acid (Prepared via General Method 8) in place of 1-methyl-5-(6-methylpyridin-2-yl)-1H-1,2,4-triazole-3-carboxylic acid. $^1$H NMR (400 MHz, DMSO-d$_6$) δ 10.44 (s, 1H), 9.26 (s, 1H), 8.24 (s, 1H), 7.98-7.94 (t, J=8.0 Hz, 1H), 7.88 (d, J=7.2 Hz, 1H), 7.81-7.79 (m, 1H), 7.40 (d, J=8.0 Hz, 1H), 7.03 (d, J=8.0 Hz, 1H), 4.97 (s, 2H), 4.43 (s, 3H), 3.99 (s, 3H).

Example 76. 5-(3-Chloropyridin-2-yl)-N-(1-hydroxy-1,3-dihydrobenzo[c][1,2]oxaborol-6-yl)-1-methyl-1H-1,2,4-triazole-3-carboxamide (I-76)

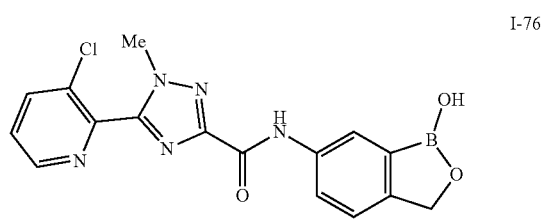 [SMILES: Cn1nc(C(=O)Nc2ccc3c(c2)B(O)OC3)nc1-c1ncccc1Cl]

I-76

This compound was prepared in a similar way to Example 74 using 5-(3-chloropyridin-2-yl)-1-methyl-1H-1,2,4-triazole-3-carboxylic acid (Prepared via General Method 8) in place of 1-methyl-5-(6-methylpyridin-2-yl)-1H-1,2,4-triazole-3-carboxylic acid. $^1$H NMR (400 MHz, DMSO-d$_6$) δ 10.52 (s, 1H), 9.27 (s, 1H), 8.77 (d, J=3.2 Hz, 1H), 8.26-8.24 (m, 2H), 7.81-7.79 (m, 1H), 7.73-7.70 (m, 1H), 7.38 (d, J=8.4 Hz, 1H), 4.97 (s, 2H), 3.97 (s, 3H).

Example 77. 5-(5-Chloropyridin-2-yl)-N-(1-hydroxy-1,3-dihydrobenzo[c][1,2]oxaborol-6-yl)-1-methyl-1H-1,2,4-triazole-3-carboxamide (I-77)

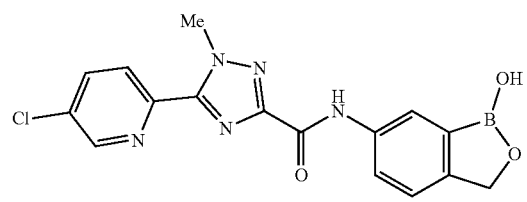

I-77

This compound was prepared in a similar way to Example 74 using 5-(5-chloropyridin-2-yl)-1-methyl-1H-1,2,4-triazole-3-carboxylic acid (Prepared via General Method 8) in place of 1-methyl-5-(6-methylpyridin-2-yl)-1H-1,2,4-triazole-3-carboxylic acid. $^1$H NMR (400 MHz, DMSO-d$_6$) δ 10.48 (s, 1H), 9.26 (s, 1H), 8.85 (d, J=2 Hz, 1H), 8.28 (d, J=7.6 Hz, 1H), 8.24-8.21 (m, 2H), 7.81-7.78 (m, 1H), 7.40 (d, J=8.0 Hz, 1H), 4.97 (s, 2H), 4.35 (s, 3H).

Example 78. N-(1-hydroxy-1,3-dihydrobenzo[c][1,2]oxaborol-6-yl)-1-methyl-5-(pyridin-3-yl)-1H-1,2,4-triazole-3-carboxamide (I-78a) and N-(1-hydroxy-1,3-dihydrobenzo[c][1,2]oxaborol-6-yl)-1-methyl-3-(pyridin-3-yl)-1H-1,2,4-triazole-5-carboxamide (I-78b)

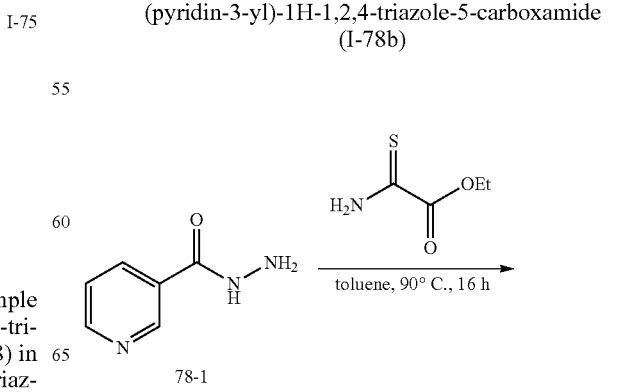

78-1

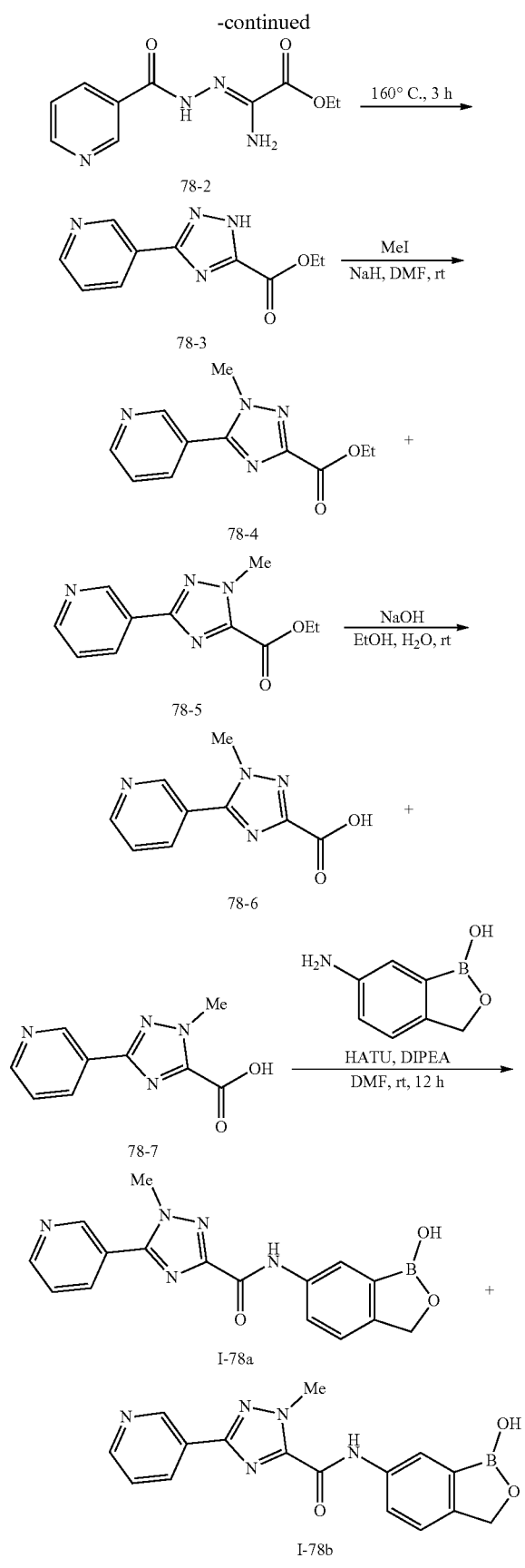

Step 1

The mixture of 78-1 (1 g, 1 equiv.) and ethyl 2-amino-2-thioxoacetate (1.16 g, 1.2 equiv.) with AcOH (0.2 mL) in toluene (50 mL) was heated to 90° C. for 16 h. The mixture of 78-2 was immediately used in the next step without further work up.

Step 2

The mixture of 78-2 in toluene was heated to 160° C. for 3 h. The solvent was removed in vacuum and the residue was dissolved in water (50 mL) and extracted with EtOAc (30 mL×4). The combined organic phases were washed with brine (50 mL), dried over $Na_2SO_4$ and concentrated in vacuum. The crude product was purified by silica gel column chromatography (DCM/MeOH 100:1 to 50:1) to get 800 mg of 78-3.

Step 3

To a stirred mixture of NaH (191 mg, 1.3 equiv.) in DMF (10 mL) was added a solution of 78-3 (800 mg, 1 equiv.) in DMF (20 mL) dropwise at 0° C. The mixture was stirred at 0° C. for further 30 min, then MeI (1.640 g, 1.3 equiv.) was added. After the addition, the mixture was stirred at 0° C. for 2 h. The mixture was poured into saturated $NH_4Cl$ solution (100 mL) and extracted with EtOAc (50 mL×3). The combined organic layers were washed with brine (50 mL), dried over $Na_2SO_4$ and concentrated in vacuum to get 1.15 g of a mixture of 78-4 and 78-5.

Step 4

To a solution of 78-4 and 78-5 (1.15 g, 1 equiv.) in THF (30 mL) was added a solution of LiOH (476 mg, 4 equiv.) in $H_2O$ (5 mL). The mixture was stirred at room temperature for 16 h. The solvent was concentrated in vacuum and the residue was dissolved in water (30 mL). The mixture was acidified with 3 M HCl. The product was purified by pre-HPLC to get 300 mg of a mixture of 78-6 and 78-7.

Step 5

To a solution of 78-6 and 78-7 (300 mg, 1 equiv.) in DMF (10 mL) was added 6-aminobenzo[c][1,2]oxaborol-1 (3/7)-ol (328 mg, 1.5 equiv.), DIPEA (760 mg, 4 equiv.) and HATU (1.12 g, 2 equiv.). The mixture was stirred at room temperature for 16 h. The mixture was poured into water (50 mL) and extracted with EtOAc (50 mL×3). The combined organic phases were washed with brine (100 mL×3), dried over $Na_2SO_4$ and concentrated in vacuum. The crude product was purified by pre-HPLC (FA) to get 32.1 mg of I-78a and 214.8 mg of I-78b as a yellow solid.

Data of I-78a $^1$H NMR (400 MHz, DMSO-$d_6$) δ 10.50 (s, 1H), 9.12 (s, 1H), 8.84-8.83 (d, J=4.4 Hz, 1H), 8.40-8.39 (d, J=7.2 Hz, 1H), 8.24 (s, 1H), 7.80-7.78 (m, 1H), 7.75-7.72 (m, 1H), 7.40-7.37 (d, J=8.4 Hz, 1H), 4.96 (s, 2H), 4.11 (s, 3H); ESI-MS: m/z 336 [M+H]$^+$;

Data of I-78b $^1$H NMR (400 MHz, DMSO-$d_6$) δ 10.78 (s, 1H), 9.27 (s, 2H), 8.69-8.68 (d, J=3.6 Hz, 1H), 8.44-8.42 (d, J=7.6 Hz, 1H), 8.25 (s, 1H), 7.81-7.80 (m, J=7.2 Hz, 1H), 7.60-7.57 (m, 1H), 7.43-7.41 (d, J=8.4 Hz, 1H), 4.98 (s, 2H), 4.25 (s, 3H); ESI-MS: m/z 336 [M+1]$^+$;

Example 79. N-(1-Hydroxy-1,3-dihydrobenzo[c][1,2]oxaborol-6-yl)-1-methyl-5-(pyridin-2-yl)-1H-1,2,4-triazole-3-carboxamide (I-79)

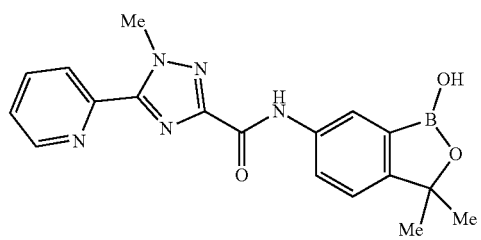

I-79

This compound was prepared in a similar way to Example 74 using 1-methyl-5-(pyridin-2-yl)-1H-1,2,4-triazole-3-carboxylic acid (Prepared via General Method 8) in place of 1-methyl-5-(6-methylpyridin-2-yl)-1H-1,2,4-triazole-3-carboxylic acid and 6-amino-3,3-dimethylbenzo[c][1,2]oxaborol-1(3/7)-ol in place of 6-aminobenzo[c][1,2]oxaborol-1(3H)-ol. $^1$H NMR (400 MHz, DMSO-d$_6$) δ 10.47 (s, 1H), 9.12 (s, 1H), 8.79 (d, J=4.1 Hz, 1H), 8.27 (d, J=7.9 Hz, 1H), 8.14 (d, J=1.8 Hz, 1H), 8.08 (dt, J=1.8, 7.8 Hz, 1H), 7.77 (dd, J=8.2, 2.0 Hz, 1H), 7.60 (ddd, J=7.6, 4.9, 1.1 Hz, 1H), 7.40 (d, J=8.3 Hz, 1H), 4.38 (s, 3H), 1.45 (s, 6H).

Example 80. N-(1-hydroxy-1,3-dihydrobenzo[c][1,2]oxaborol-6-yl)-1-methyl-5-(pyridin-2-yl)-1H-1,2,4-triazole-3-carboxamide (I-80)

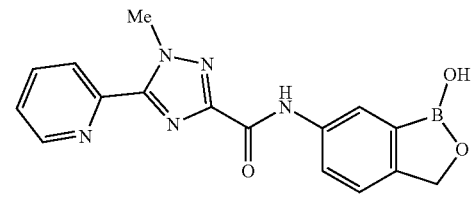

I-80

This compound was prepared in a similar way to Example 74 using 1-methyl-5-(pyridin-2-yl)-1H-1,2,4-triazole-3-carboxylic acid (Prepared via General Method 8) in place of 1-methyl-5-(6-methylpyridin-2-yl)-1H-1,2,4-triazole-3-carboxylic acid, $^1$H NMR (400 MHz, DMSO-d$_6$) δ 10.48 (s, 1H), 9.27 (s, 1H), 8.80 (d, J=4.0 Hz, 1H), 8.29-8.26 (m, 2H), 8.09 (t, J=7.2 Hz, 1H), 7.81 (d, J=8.0 Hz, 1H), 7.63-7.60 (m, 1H), 7.41 (d, J=8.4 Hz, 1H), 4.99 (s, 2H), 4.39 (s, 3H).

Example 81. N-(1-hydroxy-1,3-dihydrobenzo[c][1,2]oxaborol-6-yl)-5-methyl-1-(6-methylpyridin-2-yl)-1H-1,2,3-triazole-4-carboxamide (I-81)

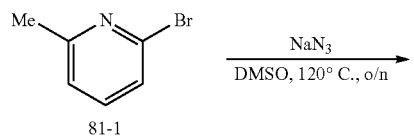

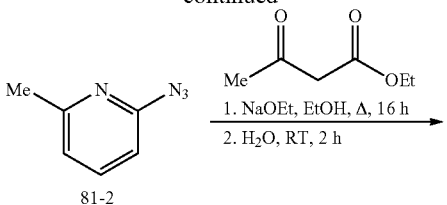

Step 1

To a solution of 81-1 (5.0 g, 1 equiv.) in DMSO (50 mL) was added NaN$_3$ (2.3 g, 1.5 equiv.) and stirred at 120° C. for 16 h. The progress of the reaction was monitored by TLC. The mixture was cooled to room temperature and 5% NaHCO$_3$ aqueous (80 mL) was added and extracted was EtOAc (100 mL*2). The organic layer was dried and concentrated to get 1.7 g of crude 81-2.

Step 2

To a solution of 81-2 (300 mg, 1 equiv.) in EtOH (5 mL) was added ethyl 3-oxobutanoate (286 mg, 1 equiv.) and NaOEt (177 mg, 1.2 equiv.) and was heated to reflux and stirred for 16 h. H$_2$O (2 mL) was added. The mixture was stirred for 2 h and concentrated to remove EtOH. EtOAc (5 mL) and H$_2$O (3 mL) was added and the aqueous phase was adjusted pH to 5 and extracted with EtOAc (5 mL*2). The combined organic phase was dried and concentrated to get 80 mg of crude 81-3.

Step 3

To a solution of 81-3 (80 mg, 1 equiv.) in DMF (3 mL) was added HATU (228 mg, 1.5 equiv.), DIPEA (103 mg, 2 equiv.) and 6-aminobenzo[c][1,2]oxaborol-1(3H)-ol (89 mg, 1.5 equiv.). The mixture was stirred at room temperature for 16 h. The reaction was completed. The mixture was purified by prep-HPLC to get 45 mg of I-81 as a yellow solid. $^1$H NMR (400 MHz, DMSO-d$_6$) δ 10.56 (s, 1H), 9.24 (s, 1H), 8.28 (s, 1H), 8.07 (t, J=8.0 Hz, 1H), 7.83 (d, J=8.0 Hz, 1H), 7.75 (d, J=8.0 Hz, 1H), 7.53 (d, J=7.6 Hz, 1H), 7.39 (d, J=8.0 Hz, 1H), 4.98 (s, 2H), 2.82 (s, 3H), 2.59 (s, 3H).

Example 82. 1-(3-Chloropyridin-2-yl)-N-(1-hydroxy-1,3-dihydrobenzo[c][1,2]oxaborol-6-yl)-5-methyl-1H-1,2,3-triazole-4-carboxamide (I-82)

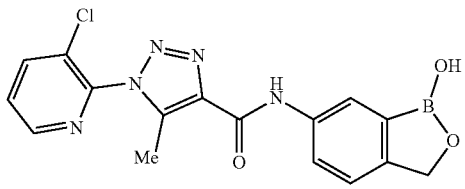

I-82

This compound was prepared in a similar way to Example 81 using 1-(3-chloropyridin-2-yl)-5-methyl-1H-1,2,3-triazole-4-carboxylic acid (Prepared via General Method 5) in place of 5-methyl-1-(6-methylpyridin-2-yl)-1H-1,2,3-triazole-4-carboxylic acid. $^1$H NMR (400 MHz, DMSO-$d_6$) δ 10.64 (s, 1H), 9.25 (s, 1H), 8.75 (dd, J=4.8, 1.4 Hz, 1H), 8.45 (dd, J=8.1, 1.2 Hz, 1H), 8.28 (d, J=1.6 Hz, 1H), 7.88-7.83 (m, 2H), 7.40 (d, J=8.0 Hz, 1H), 4.98 (s, 2H), 2.58 (s, 3H).

Example 83. 1-(5-Chloropyridin-2-yl)-N-(1-hydroxy-1,3-dihydrobenzo[c][1,2]oxaborol-6-yl)-5-methyl-1H-1,2,3-triazole-4-carboxamide (I-83)

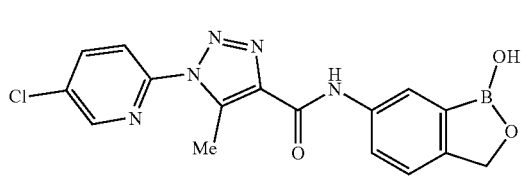

I-83

This compound was prepared in a similar way to Example 81 using 1-(5-chloropyridin-2-yl)-5-methyl-1H-1,2,3-triazole-4-carboxylic acid (Prepared via General Method 5) in place of 5-methyl-1-(6-methylpyridin-2-yl)-1H-1,2,3-triazole-4-carboxylic acid. $^1$H NMR (400 MHz, DMSO-$d_6$) δ 10.60 (s, 1H), 9.27 (s, 1H), 8.79 (d, J=2.4 Hz, 1H), 8.33 (dd, J=8.8, 2.8 Hz, 1H), 8.26 (s, 1H), 8.03 (d, J=8.4 Hz, 1H), 7.83 (dd, J=8.4, 2.0 Hz, 1H), 7.39 (d, J=8.4 Hz, 1H), 4.98 (s, 2H), 2.82 (s, 3H).

Example 84. N-(1-hydroxy-1,3-dihydrobenzo[c][1,2]oxaborol-6-yl)-5-methyl-1-(pyridin-2-yl)-1H-1,2,3-triazole-4-carboxamide (I-84)

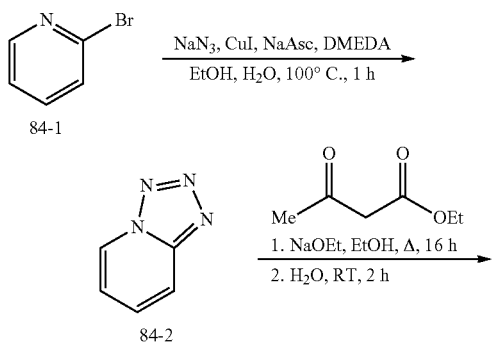

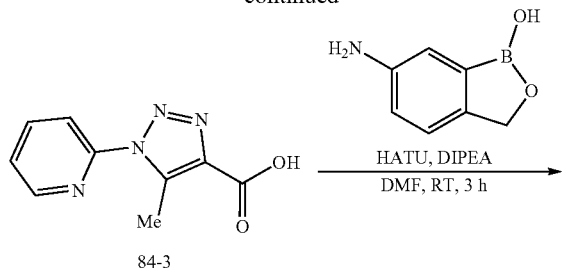

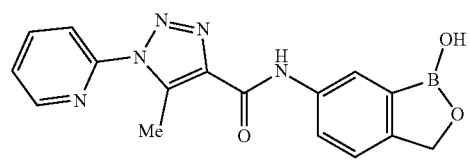

Step 1

To a suspension of 84-1 (25 g, 1 equiv.) in $H_2O$ (200 mL) and EtOH (500 mL) was added sodium azide (31.500 g, 3 equiv.), copper(I) iodide (3.0 g, 0.1 equiv.), sodium ascorbate (1.57 g, 0.05 equiv.) and DMEDA (2.12 g, 0.15 equiv.) at room temperature. The suspension was stirred at refluxing for 1 h. After cooling to room temperature, $H_2O$ (1 L) was added and the pH was adjusted to 9 with $NaHCO_3$ solid. The mixture was extracted with DCM (1 L*4) and the combined organic phase was washed with brine, dried over $Na_2SO_4$, filtered and concentrated and purified by column to get 18 g of crude 84-2 as a grey solid.

Step 2

To a solution of 84-2 (8.0 g, 1 equiv.) in EtOH (200 mL) was added ethyl 3-oxobutanoate (8.67 g, 1 equiv.) and NaOEt (5.44 g, 1.2 equiv.) and was heated to reflux and stirred for 16 h. $H_2O$ (200 mL) was added. The mixture was stirred for 2 h and concentrated to remove EtOH. EtOAc (500 mL) and $H_2O$ (300 mL) was added and the aqueous phase was adjusted pH to 5 and extracted with EtOAc (500 mL*2). The combined organic phase was dried and concentrated to get 6.90 g (33.8 mmol, 51%) of 84-3, which was used without further purification in the next step.

Step 3

To a solution of 84-3 (2.50 g, 1 equiv.) in DMF (50 mL) was added HATU (7.0 g, 1.5 equiv.), DIPEA (3.2 g, 2 equiv.) and 6-aminobenzo[c][1,2]oxaborol-1(3H)-ol (2.74 g, 1.5 equiv.). The mixture was stirred at room temperature for 16 h, at which time TLC indicated the reaction was completed. The mixture was purified by preparative HPLC to get 1.30 g (3.89 mmol, 32%) of I-84 as a yellow solid. $^1$H NMR (400 MHz, DMSO-$d_6$) δ 10.58 (s, 1H), 9.24 (s, 1H), 8.71-8.69 (dd, J=4.8, 0.8 Hz, 1H), 8.27 (s, 1H), 8.19 (m, 1H), 7.98-7.96 (d, J=8.0 Hz, 1H), 7.84-7.81 (dd, J=8.0, 0.2 Hz, 1H), 7.68-7.66 (m, 1H), 7.39-7.37 (d, J=8.0 Hz, 1H), 4.97 (s, 2H), 2.81 (s, 3H). LC/MS m/z 336 [M+H]+.

Example 85. N-(1-hydroxy-3,3-dimethyl-1,3-dihydrobenzo[c][1,2]oxaborol-6-yl)-5-methyl-1-(pyridin-2-yl)-1H-1,2,3-triazole-4-carboxamide (I-85)

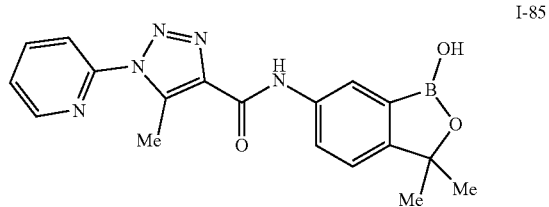 [SMILES: Cc1c(C(=O)Nc2ccc3c(c2)B(O)OC3(C)C)nnn1-c1ccccn1]

This compound was prepared in a similar way to Example 84 using Amino-CBO-4 in place of 6-aminobenzo[c][1,2]oxaborol-1(3H)-ol. $^1$H NMR (400 MHz, DMSO-d$_6$) δ=10.57 (s, 1H), 9.09 (s, 1H), 8.73-8.68 (m, 1H), 8.23-8.13 (m, 2H), 7.97 (d, J=8.2 Hz, 1H), 7.79 (dd, J=8.2, 1.9 Hz, 1H), 7.67 (ddd, J=7.4, 4.9, 0.9 Hz, 1H), 7.39 (d, J=8.3 Hz, 1H), 2.81 (s, 3H), 2.08-2.07 (m, 1H), 1.45 (s, 6H).

Example 86. 1-(4-fluorophenyl)-N-(1-hydroxy-1,3-dihydrobenzo[c][1,2]oxaborol-6-yl)-5-methyl-1H-1,2,3-triazole-4-carboxamide (I-86)

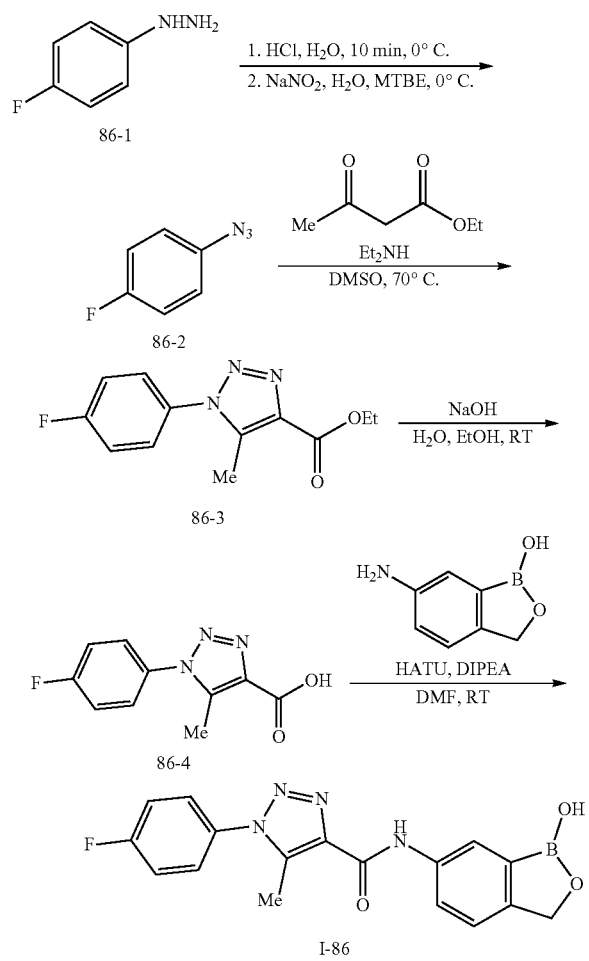

Step 1

86-1 (6.18 g, 1 equiv.) was added dropwise to a cold solution of concentrated hydrochloric acid (40.0 mL) over a period of 10 min at 0° C. MTBE (20.0 mL) was added, followed by the dropwise addition of a solution of sodium nitrite (3.4 g, 1.3 equiv.) in water (5.0 mL) and kept the temperature below 5° C. The reaction was stirred at 0° C. for 3 h and then extracted with EtOAc (40 mL*4). The organic layer was washed with water and brine, dried over Na$_2$SO$_4$ and carefully evaporated in vacuo to get 2.3 g of 86-2 (1-azido-4-fluorobenzene).

Steps 2-4

I-86 was prepared in a similar way to Example 84 using 1-azido-4-fluorobenzene in place of 2-azido-6-methylpyridine. $^1$H NMR (400 MHz, DMSO-d$_6$) δ 10.57 (s, 1H), 9.24 (s, 1H), 8.28 (d, J=1.8 Hz, 1H), 7.82 (dd, J=8.2, 1.9 Hz, 1H), 7.77-7.73 (m, 2H), 7.55-7.49 (m, 2H), 7.38 (d, J=8.4 Hz, 1H), 4.97 (s, 2H), 2.57 (s, 3H).

Example 87. N-(1-hydroxy-1,3-dihydrobenzo[c][1,2]oxaborol-6-yl)-5-methyl-1-(3-(trifluoromethyl)phenyl)-1H-1,2,3-triazole-4-carboxamide (I-87)

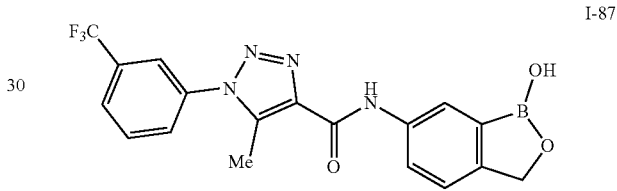

This compound was prepared in a similar way to Example 86 using 5-methyl-1-(3-(trifluoromethyl)phenyl)-1H-1,2,3-triazole-4-carboxylic acid (Prepared via General Method 2) in place of 1-(4-fluorophenyl)-5-methyl-1H-1,2,3-triazole-4-carboxylic acid. $^1$H NMR (400 MHz, DMSO-d$_6$) δ 10.59 (s, 1H), 9.25 (s, 1H), 8.28 (d, J=1.6 Hz, 1H), 8.14 (s, 1H), 8.08-8.01 (m, 2H), 7.97-7.90 (m, 1H), 7.84 (dd, J=8.2, 1.9 Hz, 1H), 7.39 (d, J=8.2 Hz, 1H), 4.98 (s, 2H), 2.63 (s, 3H).

Example 88. N-(1-hydroxy-1,3-dihydrobenzo[c][1,2]oxaborol-6-yl)-1-(2-methoxyphenyl)-5-methyl-1H-1,2,3-triazole-4-carboxamide (I-88)

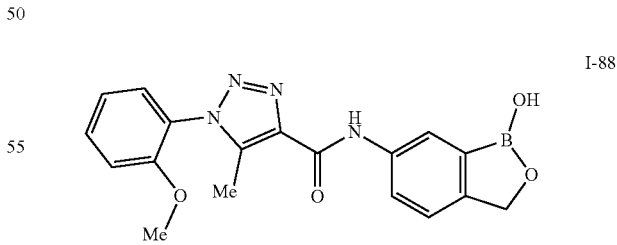

This compound was prepared in a similar way to Example 86 using 1-(2-methoxyphenyl)-5-methyl-1H-1,2,3-triazole-4-carboxylic acid (Prepared via General Method 2) in place of 1-(4-fluorophenyl)-5-methyl-1H-1,2,3-triazole-4-carboxylic acid and 6-aminobenzo[c][1,2]oxaborol-1(3H)-ol. $^1$H NMR (400 MHz, DMSO-d$_6$) δ 10.51 (s, 1H), 9.25 (s, 1H), 8.27 (d, J=1.6 Hz, 1H), 7.83 (dd, J=8.2, 2.0 Hz, 1H), 7.69-7.63 (m, 1H), 7.52 (dd, J=7.6, 1.6 Hz, 1H), 7.38 (t, J=8.4 Hz, 2H), 7.21 (dt, J=7.6, 0.9 Hz, 1H), 4.98 (s, 2H), 3.83 (s, 3H), 2.39 (s, 3H).

Example 89. A-(1-hydroxy-1,3-dihydrobenzo[c][1,2]oxaborol-6-yl)-5-methyl-1-phenyl-1H-1,2,3-triazole-4-carboxamide (I-89)

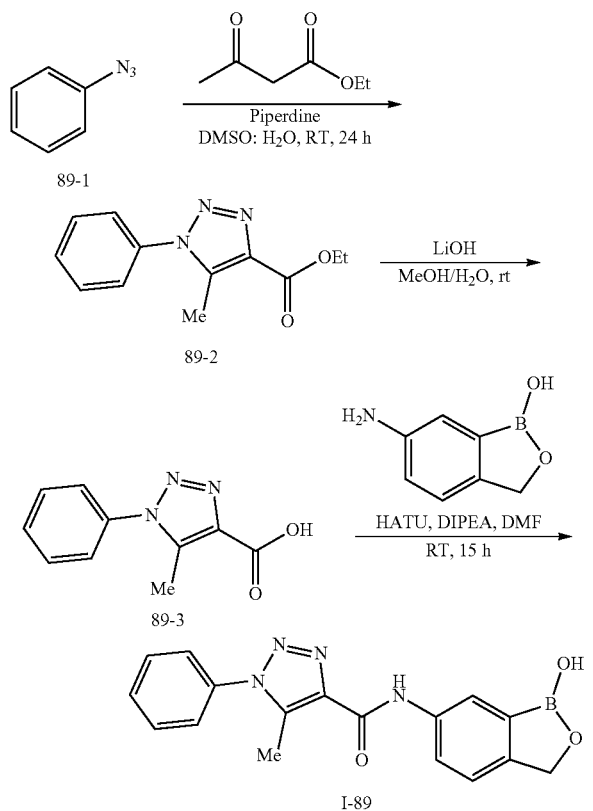

Step 1
To a solution of azidobenzene (500 mg, 1.0 eq) in a mixture of DMSO/water (10:1) was added ethyl 3-oxobutanoate (550 mg, 1.0 equiv) and piperidine (70 mg, 0.2 equiv). The mixture was stirred at RT for 24 h. After workup and column purification, 89-2 (300 mg, 1.30 mmol, 31%) was isolated.

Step 2
To a solution of 89-2 (300 mg, 1 equiv) in THF/H₂O (7:3) was added lithium hydroxide monohydrate (163 mg, 3 equiv). The reaction was stirred at RT for 16 h, then was acidified to pH=2 with 2N HCl. The solid product was isolated by filtration and dried. Trituration of the crude solid with diethyl ether and pentane gave 89-3 (150 mg, 0.74 mmol, 57%) as an off white solid.

Step 3
To a solution of 89-3 (200 mg, 1 equiv) in DMF (5 mL) was added DIPEA (3.0 equiv) and HATU (1.5 equiv). The mixture was stirred at RT for 15 min, then 6-aminobenzo[c][1,2]oxaborol-1(3H)-ol (1.2 equiv) was added. The reaction was stirred at RT for 16 h. After work up and purification by reversed phase chromatography, 1-89 (80 mg, 0.24 mmol, 24%). ¹H NMR (400 MHz, DMSO-d₆) δ=10.56 (s, 1H), 9.26 (s, 1H), 8.29 (d, J=1.2 Hz, 1H), 7.82 (dd, J=8.0, 1.2 Hz, 1H), 7.70-7.69 (m, 5H), 7.40 (d, J=8.4 Hz, 1H), 4.99 (s, 2H), 2.6 (s, 3H). LC/MS: m/z 335 [M+H]+. HPLC: 98.99% (220 nm).

Example 90. 1-(4-chlorophenyl)-N-(1-hydroxy-1,3-dihydrobenzo[c][1,2]oxaborol-6-yl)-5-methyl-1H-1,2,3-triazole-4-carboxamide 1-90

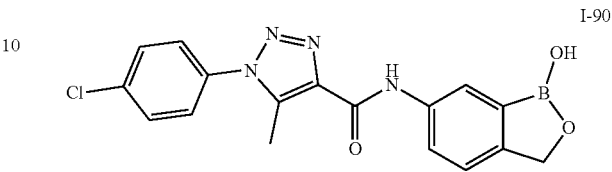

This compound was prepared in a similar manner to Example 89 with 1-(4-chlorophenyl)-5-methyl-1H-1,2,3-triazole-4-carboxylic acid (Prepared via General Method 2) replacing of 5-methyl-1-phenyl-1H-1,2,3-triazole-4-carboxylic acid and Amino-CBO-1 replacing of Amino-CBO-2. ¹H NMR (400 MHz, DMSO-d₆): δ 10.51 (s, 1H), 9.18 (s, 1H), 8.23 (d, J=1.66 Hz, 1H), 7.78 (dd, J=8.25, 2.0 Hz, 1H), 7.70 (d, J=1.56 Hz, 4H), 7.34 (d, J=8.30 Hz, 1H), 4.93 (s, 2H), 2.55 (s, 3H); LC-MS: m/z=369 [M+H]⁺. HPLC purity: 99.6% (220 nm) and 100% (254 nm).

Example 91. N-(1-hydroxy-1,3-dihydrobenzo[c][1,2]oxaborol-6-yl)-1-(4-methoxyphenyl)-5-methyl-1H-1,2,3-triazole-4-carboxamide

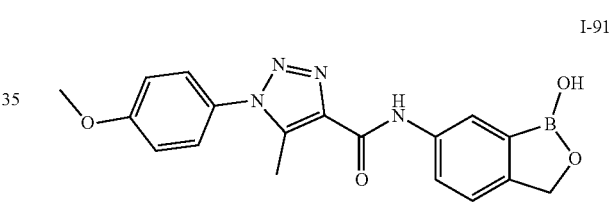

This compound was prepared in a similar manner to Example 89 with 1-(4-methoxyphenyl)-5-methyl-1H-1,2,3-triazole-4-carboxylic acid (Prepared via General Method 2) replacing of 5-methyl-1-phenyl-1H-1,2,3-triazole-4-carboxylic acid and Amino-CBO-1 replacing of Amino-CBO-2. ¹H NMR (400 MHz, DMSO-d₆): δ 10.47 (s, 1H), 9.17 (s, 1H), 8.23 (d, J=1.81 Hz, 1H), 7.78 (dd, J=8.25, 2.0 Hz, 1H), 7.54 (m, 2H), 7.34 (d, J=8.35 Hz, 1H), 7.14 (m, 2H), 4.93 (s, 2H), 2.55 (s, 3H); LC-MS: m/z=365 [M+H]⁺. HPLC purity: 95% (220 nm) and 98% (254 nm).

Example 91. N-(1-hydroxy-3,3-dimethyl-1,3-dihydrobenzo[c][1,2]oxaborol-6-yl)-5-methyl-1-phenyl-1H-1,2,3-triazole-4-carboxamide (I-91)

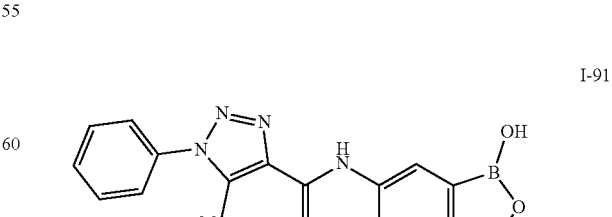

This compound was prepared in a similar way to Example 89 using Amino-CBO-4 in place of 6-aminobenzo[c][1,2]oxaborol-1(3H)-ol. ¹H NMR (400 MHz, DMSO-d₆) δ 10.56 (s, 1H), 9.08 (s, 1H), 8.17 (d, J=1.6 Hz, 1H), 7.79 (d, J=8.4 Hz, 1H), 7.78-7.68 (m, 5H), 2.59 (s, 3H), 1.45 (s, 6H).

Example 93. N-(1-hydroxy-1,3-dihydrobenzo[c][1,2]oxaborol-6-yl)-5-methyl-1-(pyridin-3-yl)-1H-1,2,3-triazole-4-carboxamide (I-93)

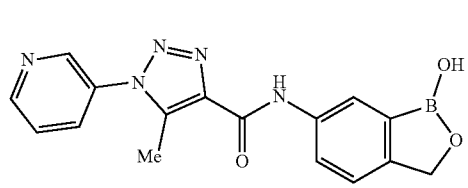

I-93

This compound was prepared in a similar way to Example 89 using pyridin-3-amine in place of aniline. (Prepared via General Method 7) ¹H NMR (400 MHz, DMSO-d₆) δ 11.06 (s, 1H), 9.29 (s, 1H), 8.98 (d, J=2.4 Hz, 1H), 8.92 (dd, J=4.9, 1.4 Hz, 1H), 8.32-8.26 (m, 2H), 7.82-7.76 (m, 2H), 7.43 (d, J=8.3 Hz, 1H), 4.99 (s, 2H).

Example 94. N-(1-hydroxy-1,3-dihydrobenzo[c][1,2]oxaborol-6-yl)-3-(pyridin-2-yl)-1H-1,2,4-triazole-5-carboxamide (I-94)

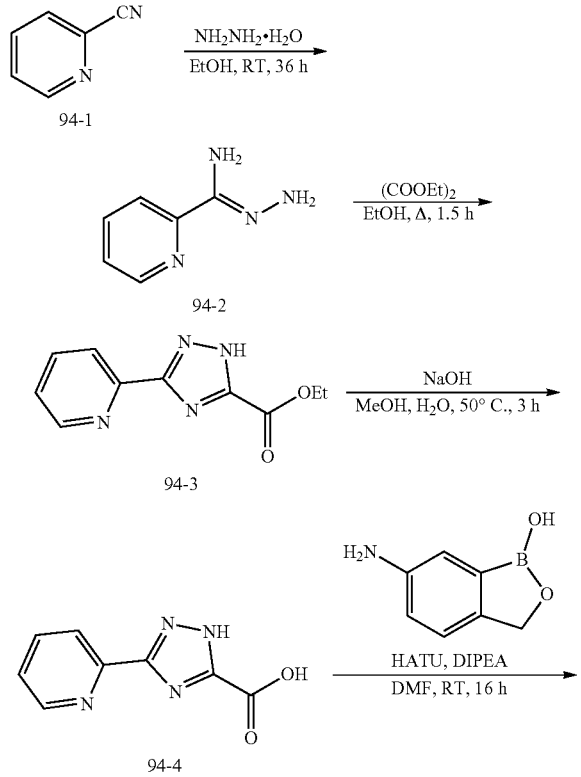

-continued

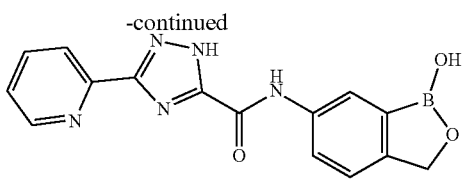

I-94

Step 1

Hydrazine hydrate (3.25 g, 85%, 1.1 equiv.) was added to the solution of 94-1 (5.2 g, 1 equiv.) in EtOH (30 mL) at 0° C. and the mixture was stirred at room temperature for 16 h. TLC showed some starting material was remained. Hydrazine hydrate (5 mL) was added at 0° C. and the mixture was stirred at room temperature for another 20 h. The pH was adjusted to 4 with 2 M HCl and the mixture was concentrated to remove EtOH. The residue was extracted with EtOAc (20 mL*3). The pH of the aqueous layer was adjusted to 9 with saturated NaHCO₃ aqueous solution and extracted with DCM (20 mL*8). The combined DCM layers were dried over Na₂SO₄ and concentrated to get 3.9 g of 94-2.

Step 2

A mixture of diethyl oxalate (5.85 g, 4.0 equiv.) and 94-2 (1.36 g, 1 equiv.) in EtOH (7 mL) was heated to reflux for 1.5 h. The mixture was cooled to room temperature and diluted with EtOAc (50 mL), washed with water (50 mL). The aqueous layer was extracted with EtOAc (20 mL*3). The combined organic layers were washed with brine (30 mL*2), dried over Na₂SO₄ and concentrated to get 1.0 g of 94-3.

Step 3

To a solution of 94-3 (400 mg, 1.0 equiv.) in methanol (3 mL), THF (3 mL) and water (4 mL) was added sodium hydroxide (200 mg, 2.5 equiv.). The mixture was stirred at 50° C. for 3 h. The mixture was cooled to room temperature and stirred for 16 h. The mixture was concentrated and diluted with water (10 mL) and extracted with DCM (10 mL*3). The pH of the aqueous phase was adjusted to 4 and the mixture was concentrated to get 130 mg of crude 94-4.

Step 4

To a solution of 94-4 (80 mg, 1 equiv.), HATU (200 mg, 1.3 equiv.) and DIPEA (200 mg, 3.7 equiv.) in DMF (2 mL) was added 6-aminobenzo[c][1,2]oxaborol-1(3H)-ol (80 mg, 1.3 equiv.). The mixture was stirred at room temperature for 16 h. The reaction was completed and the mixture was purified by prep-HPLC to get 62.8 mg of I-94 as a white solid. ¹H NMR (400 MHz, DMSO-d₆) δ 10.56 (s, 1H), 9.33 (s, 1H), 8.77 (d, J=4.8 Hz, 1H), 8.25-8.21 (m, 2H), 7.84-7.82 (m, 1H), 7.60 (dd, J=6.8, 5.2 Hz, 1H), 7.42 (d, J=8.4 Hz, 1H), 4.99 (s, 2H).

Example 95. N-(1-hydroxy-1,3-dihydrobenzo[c][1,2]oxaborol-6-yl)-1-methyl-3-(pyridine-2-yl)-1H-1,2,4-triazole-5-carboxamide (I-95)

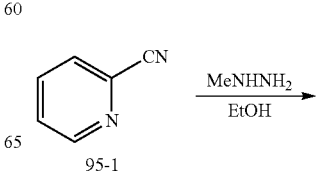

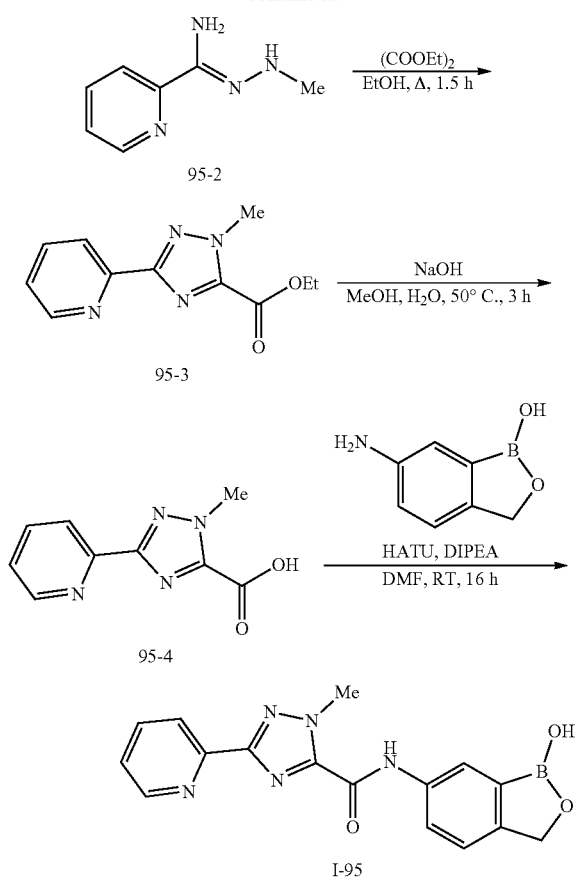

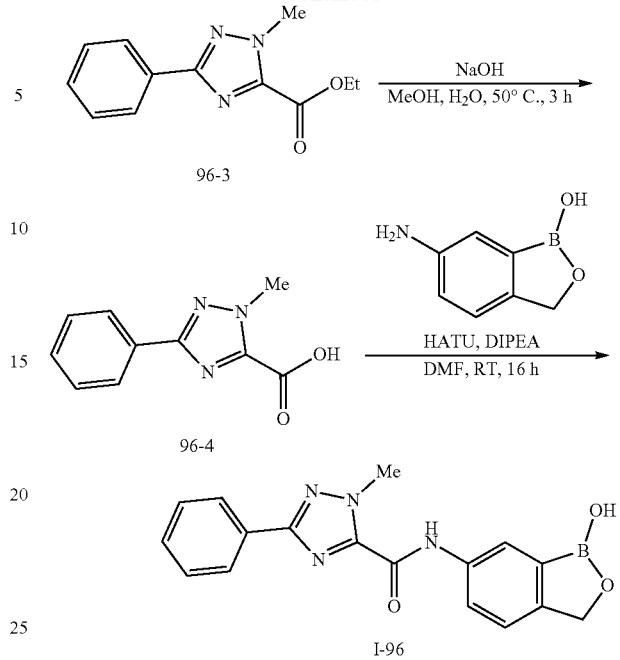

This compound was prepared in a similar manner to Example 94 using methylhydrazine in place of hydrazine hydrate, ¹H NMR (400 MHz, DMSO-d₆) δ 10.86 (s, 1H), 9.28 (s, 1H), 8.71 (d, J=4.4 Hz, 1H), 8.26 (d, J=1.2 Hz, 1H), 8.16 (d, J=4.0 Hz, 1H), 7.90 (d, J=1.6 Hz, 1H), 7.83 (dd, J=8.4, 1.6 Hz, 1H), 7.51 (m, 1H), 7.44 (d, J=8.0 Hz, 1H), 5.00 (s, 2H), 4.27 (s, 3H).

Example 96. N-(1-hydroxy-1,3-dihydrobenzo[c][1,2]oxaborol-6-yl)-1-methyl-3-phenyl-1H-1,2,4-triazole-5-carboxamide (I-96)

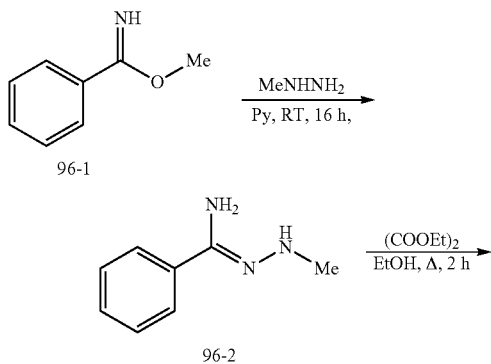

Step 1

A solution of 96-1 (3.0 g, 1 equiv.) and methylhydrazine (2.8 g, 40% in water, 1.5 equiv.) in pyridine (30.0 mL) was stirred at room temperature for 16 h. The reaction was completed. H₂O (30 mL) was added and the mixture was extracted with DCM (30 mL*2). The pH of the aqueous layer was adjusted to 10 with saturated Na₂CO₃ aqueous solution. The mixture was extracted with DCM (30 mL*4). The combined organic layers were dried over Na₂SO₄ and concentrated in vacuum to get 1.5 g of crude 96-2 ((Z)—N'-methylbenzohydrazonamide).

Steps 2-4

I-96 was prepared in a similar way to Example 93 using (Z)—N'-methylbenzohydrazonamide in place of (Z)—N'-methylpicolinohydrazonamide. ¹H NMR (400 MHz, DMSO-d₆) δ=10.30 (s, 1H), 9.29 (s, 1H), 8.25 (d, J=1.6 Hz, 1H), 8.09-8.06 (m, 3H), 7.49-7.46 (m, 4H), 5.02 (s, 2H), 3.72 (s, 3H).

Example 97. 3-(4-fluorophenyl)-N-(1-hydroxy-1,3-dihydrobenzo[c][1,2]oxaborol-6-yl)-1-methyl-1H-1,2,4-triazole-5-carboxamide (I-97)

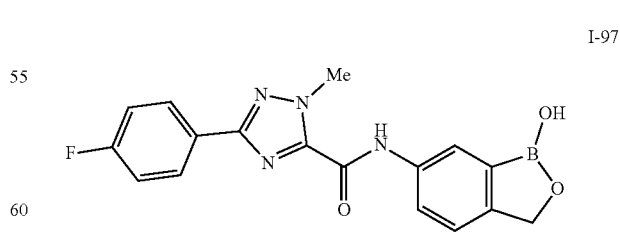

This compound was prepared in a similar way to Example 96 using 3-(4-fluorophenyl)-1-methyl-1H-1,2,4-triazole-5-carboxylic acid (Prepared via General Method 9) in place of 1-methyl-3-phenyl-1H-1,2,4-triazole-5-carboxylic acid. ¹H NMR (400 MHz, DMSO-d₆) δ 10.31 (s, 1H), 9.30 (s, 1H), 8.21 (d, J=1.6 Hz, 1H), 8.14-8.07 (m, 2H), 8.04 (dd, J=8.0, 2.0 Hz, 1H), 7.48 (d, J=8.4 Hz, 1H), 7.29 (d, J=8.8 Hz, 2H), 5.01 (s, 2H), 3.71 (s, 3H).

Example 98. N-(1-hydroxy-1,3-dihydrobenzo[c][1,2]oxaborol-6-yl)-3-(pyridin-3-yl)-1H-1,2,4-triazole-5-carboxamide (I-98)

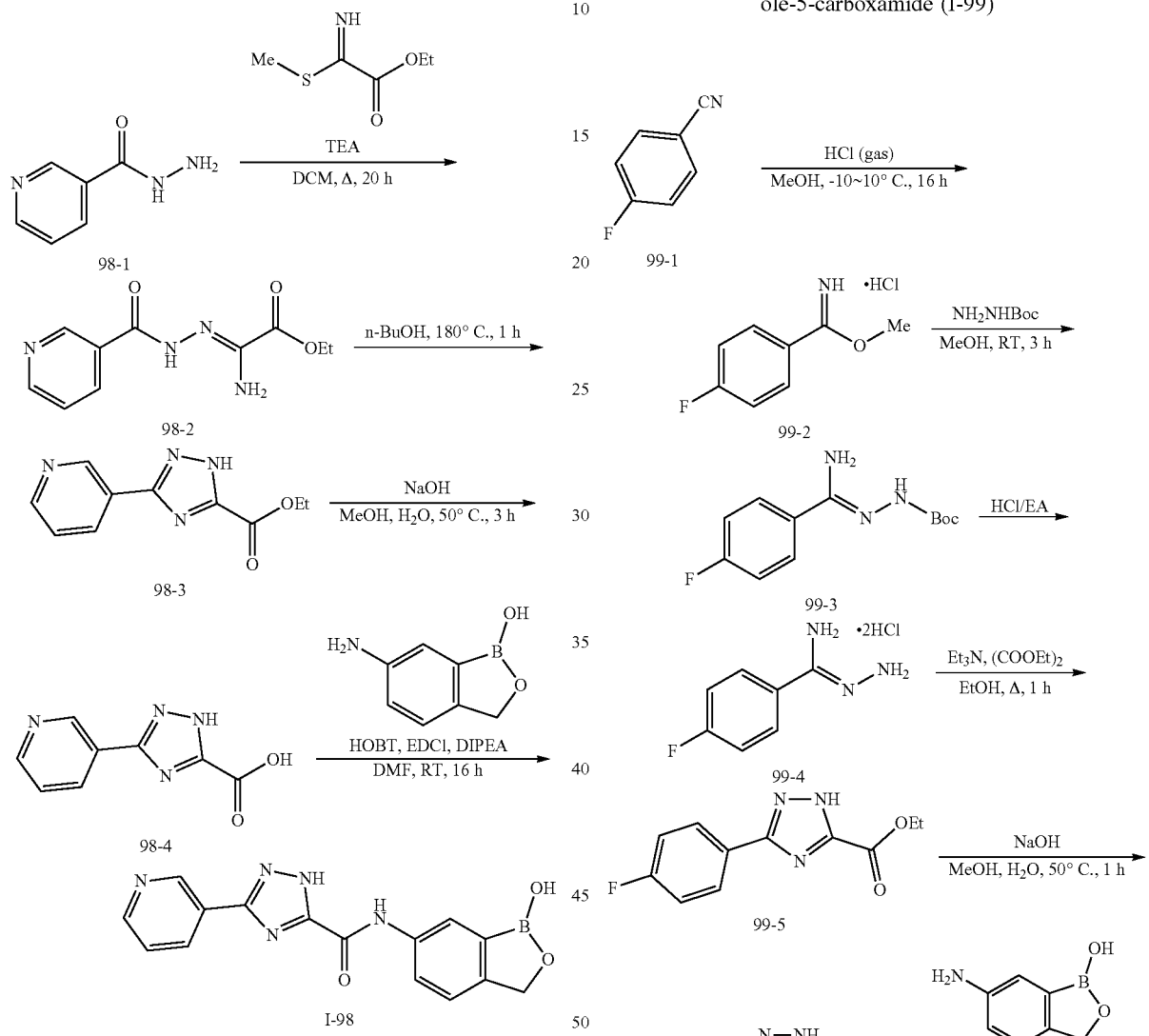

Step 1

To a solution of 98-1 (1.6 g, 1 equiv.) and ethyl 2-imino-2-(methylthio)acetate (4.0 g, 2.3 equiv.) in DCM (30 mL) was added TEA (3 mL). The mixture was stirred at refluxing for 20 h. Yellow precipitate was formed. The mixture was filtered, and the cake was washed with DCM to get 2.1 g of crude 98-2.

Step 2

The solution of 98-2 (1.1 g, 1 equiv.) in n-BuOH (10 mL) was heated to 180° C. for 1 h under microwave. The mixture was cooled to room temperature and concentrated with oil pump to get crude 98-3 (ethyl 3-(pyridin-3-yl)-1H-1,2,4-triazole-5-carboxylate) used for the next step directly.

Steps 3-4

I-98 was prepared in a similar way as Example 94 using ethyl 3-(pyridin-3-yl)-1H-1,2,4-triazole-5-carboxylate in place of ethyl 3-(pyridin-2-yl)-1H-1,2,4-triazole-5-carboxylate. $^1$H NMR (400 MHz, DMSO-$d_6$) δ 10.64 (s, 1H), 9.31 (m, 2H), 8.70 (d, J=3.6 Hz, 1H), 8.46-8.44 (m, 1H), 8.25-8.23 (m, 1H), 7.87-7.84 (m, 1H), 7.60 (dd, J=8.0, 5.2 Hz, 1H), 7.44 (d, J=8.4 Hz, 1H), 5.00 (s, 2H).

Example 99. 3-(4-Fluorophenyl)-N-(1-hydroxy-1,3-dihydrobenzo[c][1,2]oxaborol-6-yl)-1H-1,2,4-triazole-5-carboxamide (I-99)

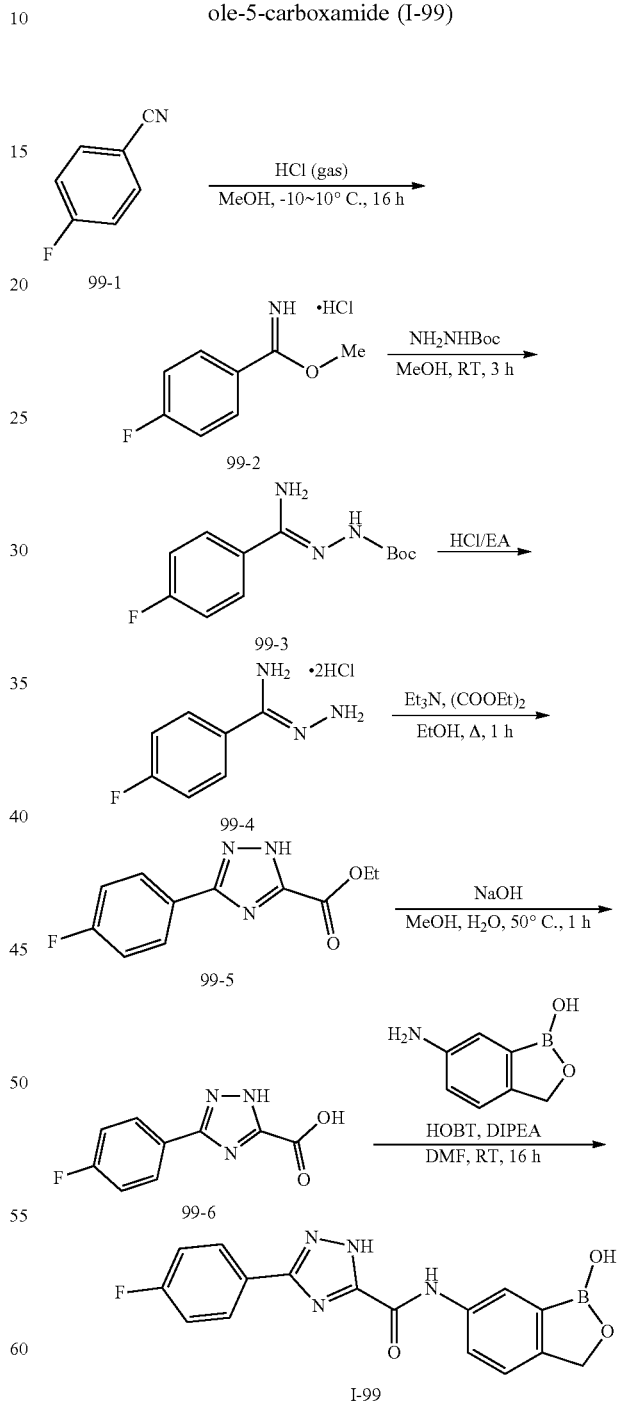

Step 1

To a solution of 99-1 (10 g, 1 equiv.) in MeOH (200 mL) was bubbled with HCl (gas) at −10° C. for 10 minutes. The reaction mixture was stirred at 10° C. for 16 h. The reaction was completed and the mixture was concentrated to get 15.2 g of crude 99-2.

Step 2

To a solution of 99-2 (1.90 g, 1 equiv.) in MeOH (20.0 mL) was added tert-butyl hydrazinecarboxylate (2.6 g, 2 equiv.) at room temperature. The reaction mixture was stirred at room temperature for 30 minutes. The mixture was concentrated to remove MeOH to give a residue. The residue was diluted with water (20 mL), adjusted to pH 2 with 4 M HCl solution and extracted with EtOAc (20 mL*2). The aqueous phase was adjusted to pH 10 and extracted with EtOAc (20 mL*3). The last organic layers were combined and washed with water (30 mL), dried with Na₂SO₄ and concentrated to get 2.73 g of crude 99-3.

Step 3

To a solution of 99-3 (2.73 g, crude) in EtOAc (30 mL) was added HCl/EtOAc (20 mL, 4 M) was added at room temperature. The reaction mixture was stirred at room temperature for 2 h. The mixture was concentrated to get 2.2 g of 99-4 which was used in next step directly.

Step 4

To a solution of 99-4 (1.6 g, 7.1 mmol) and diethyl oxalate (5.0 g, 4.8 equiv.) in EtOH (20 mL) was added TEA (2.5 mL, 2 equiv.). The reaction mixture was stirred at refluxing for 1 h. The mixture was concentrated. The residue was diluted with EtOAc (20 mL) and filtered to remove the hydrochloride salt of triethylamine. The filtrate was washed with water (20 mL*3), dried and concentrated to get 730 mg of 99-5 (ethyl 3-(4-fluorophenyl)-1H-1,2,4-triazole-5-carboxylate).

Steps 5-6

I-99 was prepared in a similar way as Example 92 using ethyl 3-(4-fluorophenyl)-1H-1,2,4-triazole-5-carboxylate in place of ethyl 3-(pyridin-2-yl)-1H-1,2,4-triazole-5-carboxylate. ¹H NMR (400 MHz, DMSO-d₆) δ 15.14 (s, 1H), 10.60 (s, 1H), 9.28 (s, 1H), 8.24 (s, 1H), 8.16 (dd, J=8.8, 5.6 Hz, 2H), 7.83 (dd, J=8.4, 2.0 Hz, 1H), 7.52-7.35 (m, 3H), 4.99 (s, 2H).

Example 100. 5-(4-Fluorophenyl)-N-(1-hydroxy-1,3-dihydrobenzo[c][1,2]oxaborol-6-yl)-1-methyl-1H-1,2,4-triazole-3-carboxamide (I-100)

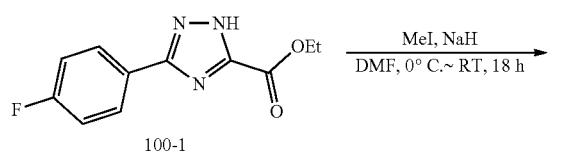

100-1

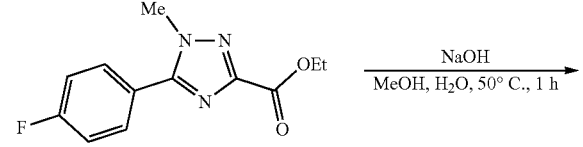

100-2

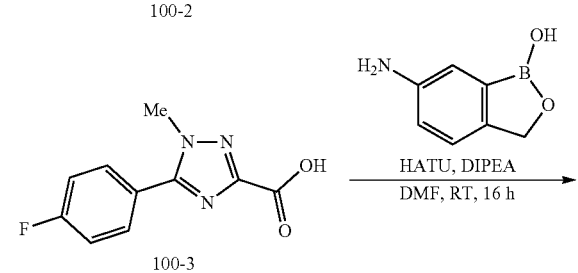

100-3

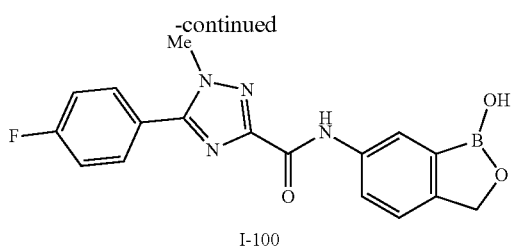

I-100

Step 1

To a solution of 100-1 (353 mg, 1.5 mmol) in DMF (3 mL) was added NaH (90 mg, 60% in oil, 1.5 equiv.) at 0° C. The reaction mixture was stirred at room temperature for 2 h. MeI (2.75 g, 19.4 mmol) was added at room temperature and the mixture was stirred at room temperature for 16 h. The reaction mixture was diluted with EtOAc (20 mL) and poured into ice water (20 mL). The aqueous layer was extracted with EtOAc (20 mL*2). The combined organic layers were washed with water (20 mL*2), dried with Na₂SO₄ and concentrated to get 300 mg of 100-2 (ethyl 5-(4-fluorophenyl)-1-methyl-1H-1,2,4-triazole-3-carboxylate).

Steps 2-3

I-100 was prepared in a similar way as Example 92 using ethyl 5-(4-fluorophenyl)-1-methyl-1H-1,2,4-triazole-3-carboxylate in place of ethyl 3-(pyridin-2-yl)-1H-1,2,4-triazole-5-carboxylate. ¹H NMR (400 MHz, DMSO-d₆) δ 10.46 (s, 1H), 9.27 (s, 1H), 8.25 (s, 1H), 7.97-7.93 (m, 2H), 7.81-7.78 (m, 1H), 7.47 (t, J=8.8 Hz, 2H), 7.39 (d, J=8.4 Hz, 1H), 4.98 (s, 2H), 4.07 (s, 3H).

Example 101. N-(1-hydroxy-1,3-dihydrobenzo[c][1,2]oxaborol-6-yl)-3-phenyl-1H-1,2,4-triazole-5-carboxamide (I-101)

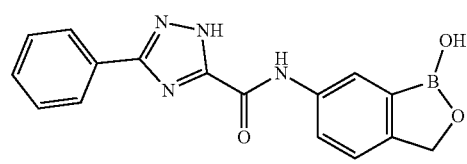

I-101

This compound was prepared in a similar way to Example 99 using benzonitrile in place of 4-fluorobenzonitrile. ¹H NMR (400 MHz, DMSO-d₆) δ 15.08 (s, 1H), 10.57 (s, 1H), 9.28 (s, 1H), 8.24 (d, J=1.6 Hz, 1H), 8.13-8.10 (m, 2H), 7.84 (dd, J=8.4, 2.0 Hz, 1H), 7.56-7.51 (m, 3H), 7.42 (d, J=8.4 Hz, 1H), 4.98 (s, 2H).

Example 102. N-(1-Hydroxy-1,3-dihydrobenzo[c][1,2]oxaborol-6-yl)-1-methyl-5-phenyl-1H-1,2,4-triazole-3-carboxamide (I-102)

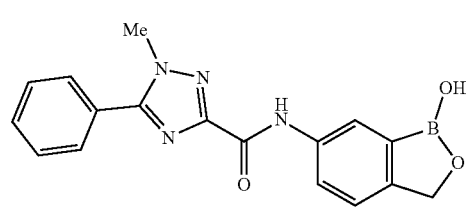

I-102

This compound was prepared in a similar way to Example 98 using 1-methyl-5-phenyl-1H-1,2,4-triazole-3-carboxylic acid (Prepared via General Method 8) in place of 5-(4-fluorophenyl)-1-methyl-1H-1,2,4-triazole-3-carboxylic acid. $^1$H NMR (400 MHz, DMSO-d$_6$) δ 10.43 (s, 1H), 9.25 (s, 1H), 8.25 (d, J=1.6 Hz, 1H), 7.88-7.87 (m, 2H), 7.87 (dd, J=8.0, 2.0 Hz, 1H), 7.62-7.61 (m, 3H), 7.38 (d, J=8.0 Hz, 1H), 4.97 (s, 2H), 4.07 (s, 3H).

Example 103. N-(1-hydroxy-3,3-dimethyl-1,3-dihydrobenzo[c][1,2]oxaborol-6-yl)-1-methyl-5-phenyl-1H-1,2,4-triazole-3-carboxamide (I-103)

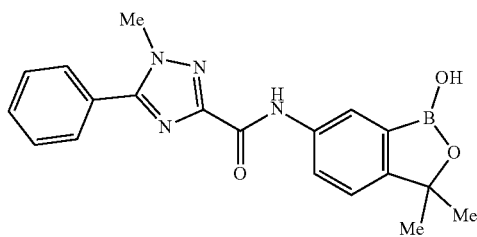

I-103

This compound was prepared in a similar way to Example 102 using 6-amino-3,3-dimethylbenzo[c][1,2]oxaborol-1(3H)-ol (Prepared via General Method 8) in place of 6-aminobenzo[c][1,2]oxaborol-1(377)-ol. $^1$H NMR (400 MHz, DMSO-d$_6$) δ 10.42 (s, 1H), 9.09 (s, 1H), 8.14 (d, J=2.0 Hz, 1H), 7.88-7.86 (m, 2H), 7.76 (dd, J=8.4 Hz, 2.0 Hz, 1H), 7.62-7.61 (m, 3H), 7.40 (d, J=8.0 Hz, 1H), 4.08 (s, 3H), 1.46 (s, 6H).

Example 104. N-(1-hydroxy-1,3-dihydrobenzo[c][1,2]oxaborol-6-yl)-5-methyl-1-(pyridin-2-yl)-1H-1,2,3-triazole-4-carboxamide arginine monohydrate (I-112)

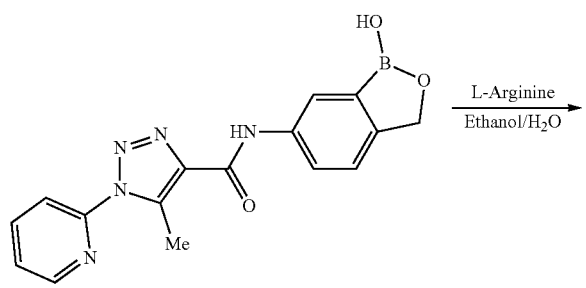

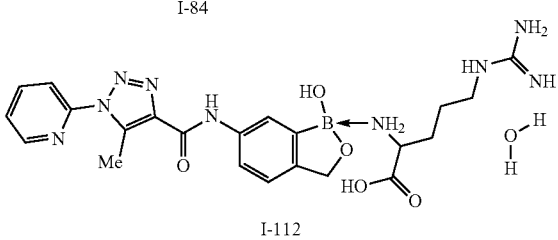

I-112

To a solution of L-Arginine (181.92 g, 1.04 mol, 2.8 equiv.) in water (1625 mL, 12.5 vol) was added 1-84 (125 g, 0.37 mol, 1.0 equiv.), the suspension was stirred for 5 minutes at 25±5° C. To the above suspension was added ethanol (837.5 mL, 6.7 vol) at 25±5° C. The mixture was stirred at 25±5° C. for 4 hours. The solids were filtered under vacuum and washed the filter cake with ethanol:water mixture (1:2 v:v, 6.7 vol). Solids were dried for 16 hours in vacuum oven at 50° C. Solids were grinded in an agate mortar and pestle and further dried in vacuum oven at 50° C. until LOD content is ≤1.0%. After drying, 165 g of I-112 were obtained as off white solid; Yield: 84%. HPLC Purity: 98.89%; Melting range: 178-185° C.; DSC: Onset temp value: 178.85° C.; Peak value: 185.00° C.; C: 49.89%, H: 5.99%, N: 23.82%; $^1$H NMR (400 MHz, DMSO-d$_6$+D2O at 80° C.) δ 10.58 (s, 1H), 8.70-8.71 (d, 1H), 8.17-8.26 (t, 1H), 7.99 (t, 1H), 9.91 (s, 1H), 7.82-7.84 (s, 1H), 7.69 (d, 1H), 7.40 (d, 1H), 4.97 (s, 2H), 3.00-3.12 (s, 1H), 2.9-3.0 (m, 4H), 1.46 (m, 4H).

Example 105. Trypanosoma brucei brucei High-Throughput Screening Assay Procedure All experiments were conducted with the bloodstream-form trypanosome T. brucei brucei 427 strain obtained from Seattle Biomedical Research Institute (Seattle, Wash.). Parasites were cultured in T-25 vented cap flasks and kept in humidified incubators at 37° C. and 5% CO$_2$. The parasite culture media was complete HMI-9 medium containing 10% FBS, 10% Serum Plus medium and penicillin/streptomycin. To ensure log growth phase, trypanosomes were sub-cultured at appropriate dilutions every 2-3 days. Approximately 50 microliters of log phase cultures were diluted 1:10 in HMI-9 and 10 μL of the diluted culture was removed and counted using a hemocytometer to determine parasite concentration. Parasites were diluted by addition of an appropriate volume of HMI-9 to achieve a final parasite concentration of 2×105/mL. Compounds of the invention to be tested were serially diluted in DMSO and 0.5 μL added to 49.5 μL HMI-9 in triplicate 96-well plates using a Biomek NX liquid handler. Parasites from the diluted stock were added to each well (50 μL) using a Multidrop 384 dispenser to give a final concentration of 1.0×105/ml parasites in 0.4% for DMSO. Trypanosomes were incubated with compounds for 72 hrs at 37° C. with 5% CO$_2$. Resazurin (20 μL of 12.5 mg/ml stock) from Sigma-Aldrich was added to each well and plates were incubated for an additional 2-4 hrs. Assay plates were read using an EnVision plate reader at an excitation wavelength of 544 nm and emission of 590 nm. Triplicate data points were averaged to generate sigmoidal dose response curve and determine IC$_{50}$ values using XLfit curve fitting software from IDBS (Guildford, UK). Data are shown below in Table 1, where compounds having an activity designated as "A" provided an IC$_{50}$<0.075 μM; compounds having an activity designated as "B" provided an IC$_{50}$ of 0.075-0.150 μM; and compounds having an activity designed as "C" provided an IC$_{50}$ of 0.151-10.0 μM.

Example 106. In Vitro Alamar Blue 72 h Drug Sensitivity Assay for T. congolense

Compounds were tested in vitro for chemotherapeutic potency against the IL3000 T. congolense (drug sensitive) strain, using the Alamar Blue assay with several modifications. Test compounds were prepared as 10 mg/mL DMSO stocks for each assay run. Compounds were assayed in at least three separate, independent test runs and an 11-point dilution curve was used to determine the IC$_{50}$ values. Bloodstream form trypanosomes were supported in HMI media containing 20% bovine serum and were incubated with test compounds for 69 h at 34° C. in a humidified atmosphere containing 5% $CO_2$. Thereafter, 10 µL of Resazurin dye (12.5 mg in 100 mL of phosphate buffered saline, Sigma-Aldrich, Buchs, Switzerland) were added for an additional 3 h. Plates were then read using a fluorescent plate reader (Spectramax, Gemini XS, Bucher Biotec, Basel, Switzerland) using an excitation wavelength of 536 nm and an emission wavelength of 588 nm. Data points were averaged to generate sigmoidal dose-response curves and IC50 values were determined using Softmax Pro 5.2 software. Data are shown below in Table 1, where compounds having an activity designated as "A" provided an $IC_{50}$<0.1 µM; compounds having an activity designated as "B" provided an $IC_{50}$ of 0.1-0.3 µM; compounds having an activity designed as "C" provided an $IC_{50}$ of 0.31-100 µM; compounds having an activity designed as "D" provided an inhibition of greater than or equal to 75% at a concentration of 1.0 µM; compounds having an activity designated as "E" provided an inhibition of less than 75% at a concentration of 1.0 µM.

Example 107. Assay for *Leishmania major* Intracellular Amastigote Assay in RAW 264.7 Macrophages The intracellular amastigote assay is a microtiter plate drug sensitivity assay that uses the activity of luciferase as a measure of proliferation of luciferase-expressing *L. major* parasites developing intracellularly inside RAW 264.7 macrophages in the presence of antileishmanial drugs or experimental compounds. (Buckner, F. S., and A. J. Wilson. *Am J Prop Med Hyg*, 2005, 72(5): 600-605.) As the activity of luciferase and its associated luminescence after addition of the substrate, luciferin, is relative to parasite growth, a test compound that inhibits the growth of the parasite will result in a lower luminescence. The luciferase-expressing *L. major* parasite used in this assay is genetically modified by adding the luciferase coding region to the pLEXSY-hyg2 vector (Jena Biosciences). The luciferase expression construct was created by digesting the luciferase coding region (1.66 kbp) of pGL3-Basic (Promega) by using two restriction enzymes, NcoI/EagI, followed by electrophoretic separation of the luciferase coding region on a 1% agarose gel. The luciferase coding region was then ligated into pLEXSY-hyg2 vector (Jena Biosciences) which had previously been digested with NcoI/NotI. The vector was linearized with SwaI and subsequently gel purified prior to transfection into *L. major* parasites. Transfections were carried out by electroporation at 480V, 13Ω, and 500 µF (0.4 mL of 1×10⁸ parasites/mL, and 0.1 mL of 10 µg DNA). Selection for transfectants was then carried out using hygromycin B (100 µg/mL). RAW 264.7 macrophages were cultured in DMEM media (ATCC Cat #30-2002) supplemented with heat-inactivated 10% FBS (Invitrogen Cat #10438-034). To begin the assay, macrophages were harvested from culture by removing all spent media, adding in 10 mL fresh media, scraping cells, and counted using Trypan Blue. The cells were resuspended in DMEM/10% HIFBS media at 2.0×10⁵ cells/mL, and then dispensed in a volume of 50 µL to yield a final concentration of 10,000 macrophages/well in 384 well tissue-culture treated sterile white plates (Nunc Cat #12-565-343) using a Tecan EVO Freedom robotics system. The plates were then incubated at 37° C. overnight in 5% $CO_2$ atmosphere for 24 hours. After overnight incubation, the media was removed from each well using the Tecan EVO Freedom robot, and *L. major* promastigotes were added to each well and allowed to invade the RAW macrophages. Promastigotes were cultured in Schneider's medium (Invitrogen Cat #11720-067) supplemented with 20% heat inactivated FBS. Metacyclic stage promastigotes provide the best invasion for this assay, and cultures should be grown to increase the percentage of metacyclic promastigotes for best results. Promastigotes were harvested from culture, counted, suspended at 2×10⁶ promastigotes/mL in DMEM/HIFBS media, and 100,000 promastigotes were dispensed per well in a volume of 50 µL. After overnight incubation, the media was removed from each well using the Tecan Freedom EVO robot, and each well was subsequently washed three times with 40 µF of fresh DMEM/HIFBS medium to remove all extracellular promastigotes. After the third wash, 69.2 µF of DMEM/HIFBS medium was added to each well using the Tecan EVO Freedom robot. Drug plates were prepared with the Tecan EVO Freedom using sterile 96 well plates containing twelve duplicate two-fold serial dilutions of each test compound suspended in DMSO. 7.8 µF of diluted test compound was added to the 69.2 µF of media present in each well providing a 10 fold final dilution of compound. The final concentration range tested was 0.5 to 10,000 ng/ml for all assays. The plates were next incubated at 37° C. and 5% $CO_2$ for 96 hours. After 96 hours of incubation, 7.5 µF of a luciferin solution (Caliper Fife Science) diluted to 150 µg/mF was added to each well, and the plates were incubated for 30 minutes at 37° C., in the dark. Each plate was read using a Infinite M200 plate reader. The 50% inhibitory concentrations ($IC_{50}$s) were then generated for each dose response test using GraphPad Prism (GraphPad Software Inc., San Diego, Calif.) using the nonlinear regression (sigmoidal dose-response/variable slope) equation. Data are shown below in Table 1, where compounds having an activity designated as "A" provided an $IC_{50}$≤1.0 µM; compounds having an activity designated as "B" provided an $IC_{50}$ of 1.1-9.9 µM; and compounds having an activity designed as "C" provided an $IC_{50}$ of 10-50 µM.

Example 108. *Leishmania major* Promastigote Growth Inhibition Assay

The promastigote assay is a microtiter plate drug sensitivity prescreen assay used to determine antileishmanial activity of candidate drugs against promastigote forms of *L. major*. (Shadow et al., PLOS Neglected Tropical Diseases, 2009, e311.) Alamar Blue, or resazurin, is a non-fluorescent indicator dye that is converted to bright red-fluorescent resorufin via the activity of mitochondrial reductases. As the activity of mitochondrial reductases is reduced in cells that are dead or dying, and the intensity of the fluorescence is relative to cell number, a test compound that kills or inhibits growth of a particular target cell, such as *L. major*, will result in a lower production of fluorescent signal. Pre-dosed microtiter drug plates for use in the promastigote drug prescreen assay were produced using sterile 384-well black optical bottom tissue culture plates (Nunc Cat #12-565-344). Candidate drugs were diluted in dimethyl sulfoxide in four 96-well plates to either 10,000 ng/ml or 1,000 ng/ml, and 4.25 µL of diluted drug was subsequently dispensed into each well of a 384-well plate. Duplicate 384 well plates were made at each test concentration (10,000 ng/mL and 1,000 ng/mL) and amphotericin B was used as a batch control. The Tecan EVO Freedom liquid handling system (Tecan US, Inc., Durham, N.C.) was used to produce all drug assay plates and conduct all pipetting operations for this assay. *L. major* parasites were cultured in Schneider's medium (Lonza Cat #04-351Q) supplemented with 20% heat inactivated FBS (Invitrogen Cat #16140-089). Promastigotes in early log growth phase were harvested from culture, counted, suspended at 1.32×10$^5$ cells/mF and 5,000 promastigotes were dispensed into each well of the 384 well plate in a volume of 38.8 μL. The 384 well plates were subsequently incubated at 28° C. for 44 hours. 8.4 μF of Alamar Blue (Promega, Cat #G8081) was added to each well, the plates were subsequently incubated at 28° C. and 5% $CO_2$ for 4 hours and then examined for the relative fluorescence units (RFU) per well using the Tecan Genios Plus (Tecan US, Inc., Durham, N.C.) with excitation set at 560 nm and emission set at 590 nm. The relative fluorescence from each well was used to determine the percent growth inhibition of each candidate compound tested. Compounds with 50% or greater inhibition of growth were selected for further analysis to determine IC50 values. Data are shown below in Table 1, where compounds having an activity designated as "A" provided an $IC_{50}$<0.6 μM; compounds having an activity designated as "B" provided an $IC_{50}$ of 0.6-2.5 μM; and compounds having an activity designed as "C" provided an $IC_{50}$ of 2.51-20 μM.

Example 109. Ex Vivo Alamar Blue 48 h Drug Sensitivity Assay for *T. vivax*

Compounds were tested ex vivo for chemotherapeutic potency against the STIB719/ILRAD560 *T. vivax* (drug sensitive) strain, using the Alamar Blue assay with several modifications. Test compounds were prepared as 10 mg/mL DMSO stocks for each assay run. Compounds were assayed in at least three separate, independent test runs and an 11-point dilution curve was used to determine the $IC_{50}$ values. Bloodstream form trypanosomes were propagated and harvested from a highly parasitemic mouse (via cardiac puncture) and were incubated with test compounds for 45 hrs at 37° C. in a humidified atmosphere containing 5% $CO_2$, supported in HMI media containing 20% bovine serum. Thereafter, 10 μL of Resazurin dye (12.5 mg in 100 mL of phosphate buffered saline, Sigma-Aldrich, Buchs, Switzerland) were added for an additional 3 hrs. Plates were then read using a fluorescent plate reader (Spectramax, Gemini XS, Bucher Biotec, Basel, Switzerland) using an excitation wavelength of 536 nm and an emission wavelength of 588 nm. Data points were averaged to generate sigmoidal dose-response curves and IC50 values were determined using Softmax Pro 5.2 software. Data are shown below in Table 1, where compounds having an activity designated as "A" provided an $IC_{50}$≤0.2 μM; compounds having an activity designated as "B" provided an $IC_{50}$ of 0.201-0.5 μM; and compounds having an activity designed as "C" provided an $IC_{50}$ of 0.51-10 μM.

Example 110. *T. brucei rhodesiense* STIB 900 Growth Inhibition Assay

The parasite strain used in this assay was isolated in 1982 from a human patient in Tanzania and after several mouse passages cloned and adapted to axenic culture conditions, ((a) Baltz, T., D. Baltz, C. Giroud, and J. Crockett. EMBO Journal, 1985, 4:1273-1277. (b) Thuita, J. K., S. M. Karanja, T. Wenzler, R. E. Mdachi, J. M. Ngotho, J. M. Kagira, R. Tidwell, and R. Brun. Acta Tropica 2008, 108:6-10.) Minimum Essential Medium (50 μl) supplemented with 25 mM HEPES, 1 g/l additional glucose, 1% MEM non-essential amino acids (100×), 0.2 mM 2-mercaptoethanol, 1 mM Na-pyruvate and 15% heat inactivated horse serum was added to each well of a 96-well microtiter plate. Serial drug dilutions of seven 3-fold dilution steps covering a range from 90 to 0.123 μg/ml were prepared. Then 10$^4$ bloodstream forms of *T. b. rhodesiense* STIB 900 in 50 μl was added to each well and the plate incubated at 37° C. under a 5% $CO_2$ atmosphere for 72 h. 10 μl Alamar Blue (resazurin, 12.5 mg in 100 ml double-distilled water) was then added to each well and incubation continued for a further 2-4 h, (Raz, B., M. Iten, Y. Grether-Buhler, R. Kaminsky, and R. Brun. Acta Trap 1997, 68:139-47.) Then the plates were read with a Spectramax Gemini XS microplate fluorometer (Molecular Devices Cooperation, Sunnyvale, Calif., USA) using an excitation wave length of 536 nm and an emission wave length of 588 nm. Data were analyzed using the microplate reader software Softmax Pro (Molecular Devices Cooperation, Sunnyvale, Calif., USA). Data are shown below in Table 1, where compounds having an activity designated as "A" provided an $IC_{50}$<0.1 μM; compounds having an activity designated as "B" provided an $IC_{50}$ of 0.1-0.3 μM; and compounds having an activity designed as "C" provided an $IC_{50}$ of 0.31-10 μM.

Example 111. *Leishmania infantum* Intracellular Amastigote Assay in Mouse Macrophages

*L. infantum* MHOM/MA(BE)/67 amastigotes were collected from the spleen of an infected donor hamster and used to infect primary peritoneal mouse macrophages. (Kaiser, M., Maes, L., Tadoori, L. P., Spangenberg, T., Ioset, J.-R. *J. Biomol. Screen.* 2015 20(5), 634-35.) To determine in vitro antileishmanial activity, 3×104 macrophages were seeded in each well of a 96-well plate. Culture medium was RPMI-1640 supplemented with L-glutamine (20 mM), 16.5 mM sodium hydrogen carbonate, and 10% fetal calf serum (FCS). After 2 d of outgrowth, 5×105 amastigotes/well were added and incubated for 2 h at 37° C. Prediluted samples to be tested were subsequently added, and the plates were further incubated for 5 d at 37° C. and 5% $CO_2$. Total parasite burdens in the well were microscopically assessed after Giemsa staining and expressed as a percentage of the total burden in the blank controls without compound. In treated wells with high amastigote burdens, an overall estimate of the total burden per well was made without discrimination between the number of infected macrophages and the number of amastigotes per infected cell. In treated wells with low burdens, exact counting was performed. The 50% inhibitory concentrations ($IC_{50}$s) were then generated for each dose response test using GraphPad Prism (GraphPad Software Inc., San Diego, Calif.) using the nonlinear regression (sigmoidal dose-response/variable slope) equation. Data are shown below in Table 1, where compounds having an activity designated as "A" provided an $IC_{50}$<3.0 μM; compounds having an activity designated as "B" provided an $IC_{50}$ of 3.0-19.9 μM; and compounds having an activity designed as "C" provided an $IC_{50}$ of 20-100 μM.

Example 112. In Vitro $IC_{50}$ Measurement of *T. cruzi* Amastigote Killing Using TdTomato-Modified *T. cruzi* (CL Strain)

The *T. cruzi* parasites used in this assay were genetically modified to express Td Tomato fluorescent protein. Vero cells (African green monkey kidney epithelial cells) were harvested from continuous cultures using trypsin and added to the inner 60 wells of 96-well Greiner Bio One plates (plate catalog #655090) at 200 ul/well of 2.5×10$^6$ cells/mL. Cells were allowed to adhere for 1 h before infection with *T. cruzi*. *T. cruzi* for infection were harvested from previously-infected Vero cells, washed, pelleted and resuspended at 5×10$^6$/mL. 50 uL of parasites were added to each well containing Vero cells. Compounds were prepared from 5 mM stock concentrations in DMSO to final concentrations in wells ranging from 5 uM to 5 nM. Wells were provided for negative controls, lacking compounds. Plates were placed into a 37° C. incubator for 20 min, then a "Day 0" reading was taken on a Synergy H4 plate reader to record initial fluorescence levels, at 544 (excitation) and 612 nm (emission). 96-well plates were placed in Tupperware containers with wet paper towels and incubated at 37° C. incubator for 72 h. After 72 h plates were reread (Day 3 reading) and data analyzed using Excel and/or Graphpad software. Day 0 fluorescence was subtracted from Day 3 to remove input parasite fluorescence. Growth curves are generated and 50% and 90% inhibitory concentrations are determined by nonlinear regression analysis. Data are shown below in Table 1, where compounds having an activity designated as "A" provided an $IC_{50}$<0.6 μM; compounds having an activity designated as "B" provided an $IC_{50}$ of 0.6-1.0 μM; and compounds having an activity designed as "C" provided an $IC_{50}$ of 1.1-10 μM.

Example 113: *Trypanosoma cruzi* C2C4 Screening Assay Procedure

Rat skeletal myoblasts (L-6 cells) were seeded in 96-well microtiter plates at 2×10³ cells/well in 100 μL RPMI 1640 medium with 10% FBS and 2 mM L-glutamine. After 24 h the medium was removed and replaced by 100 μL per well containing 5×10³ trypomastigote forms of *T. cruzi* Tulahuen strain C2C4 containing the β-galactosidase (Lac Z) gene (Buckner, et al., Antimicrobial Agents and Chemotherapy, 40: 2592-2597 (1996)). After 48 h the medium was removed from the wells and replaced by 100 μL fresh medium with or without a serial drug dilution of the seven 3-fold dilution steps covering a range from 90 to 0.123 μg/mL. After 96 h of incubation the plates were inspected under an inverted microscope to assure growth of the controls and sterility. The substrate (50 μL) chlorophenol red-β-D-galactopyranoside (CPRG, Roche Diagnostics, Ltd) in 0.25% Nonidet P-40/PBS was added to all wells and a color reaction developed within 2-6 h which was read photometrically at 540 nm. Data were transferred into the graphic program Softmax Pro (Molecular Devices), which calculated $IC_{50}$ values. Data are shown below in Table 1, where compounds having an activity designated as "A" provided an $IC_{50}$<0.06 μM; compounds having an activity designated as "B" provided an $IC_{50}$ of 0.06-0.10 μM; and compounds having an activity designed as "C" provided an $IC_{50}$ of 0.11-1.0 μM.

Example 114. *Trypanosoma brucei rhodesiense* STIB 900 Screening Assay Procedure The *Trypanosoma brucei rhodesiense* STIB 900 strain was isolated in 1982 from a human patient in Tanzania and after several mouse passages cloned and adapted to axenic culture conditions (Baltz, et al., *EMBO Journal* 4: 1273-1277 (1985); Thuita, et al., *Acta Tropica* 108: 6-10 (2008)). Minimum Essential Medium (50 μL) supplemented with 25 mM HEPES, 1 g/L additional glucose, 1% MEM non-essential amino acids (100×), 0.2 mM 2-mercaptoethanol, 1 mM Na-pyruvate and 15% heat inactivated horse serum was added to each well of a 96-well microtiter plate. Serial drug dilutions of seven 3-fold steps covering a range from 90 to 0.123 μg/mL were prepared. Then 10⁴ bloodstream forms of *T. b. rhodesiense* STIB 900 in 50 μL was added to each well and the plate incubated at 37° C. under a 5% $CO_2$ atmosphere for 72 h. 10 μL Alamar Blue (resazurin, 12.5 mg in 100 mL double-distilled water) was then added to each well and incubation continued for a further 2-4 h (Raz, et al., *Acta Tropica* 68: 139-47 (1997)). Then the plates were read with a Spectramax Gemini XS microplate fluorometer (Molecular Devices Corporation, Sunnyvale, Calif., USA) using an excitation wavelength of 536 nm and an emission wavelength of 588 nm. Data were transferred into the graphic program Softmax Pro (Molecular Devices), which calculated $IC_{50}$ values. Data are shown below in Table 1, where compounds having an activity designated as "A" provided an $IC_{50}$<0.10 μM; compounds having an activity designated as "B" provided an $IC_{50}$ of 0.10-0.25 μM; and compounds having an activity designed as "C" provided an $IC_{50}$ of 0.26-2.0 μM.

TABLE A

| Example | IC50: I Org. Growth T. brucei brucei SBRI 427, 3 d [uM][1] | IC50: I Org. Growth T. congolense IL-3000, 3 d [uM][2] | IC50: I Org. intracellular amastigote Growth L. major, 4 d [uM][3] | IC50: I Org. promastigote Growth L. major, 2 d [uM][4] | IC50: I Hypoxanthine Incorporation T. vivax STIB 719/ILRA D 560, 2 d [ uM][5] |
|---|---|---|---|---|---|
| 1 |  | A | A | A | B |
| 2 |  | A | A | A | A |
| 3 |  | B | A | B | C |
| 4 |  | B | A | B | C |
| 5 |  | B | A | B | C |
| 6 |  | B | A | B | C |
| 7 |  | C | B | C | C |
| 8 |  | C | C | C | C |
| 9 |  | C | C | B | C |
| 10 |  | A | A | A | B |
| 11 |  | A | B | A | B |
| 12 |  | A | B | C | B |
| 13 |  | B | B | B | C |
| 14 |  | A | B | C | B |
| 15 |  | B | C | C | C |
| 16 |  | C | C | B | C |
| 17 |  | C | C | C | C |
| 18 |  | A | A | B | B |
| 19 |  | B | A | B | B |
| 20 |  | C | C | A | C |
| 21 |  | A | A | A | A |
| 22 |  | B | A | A | C |
| 23 |  | A | A | A | B |
| 24 |  | A | A | B | B |

TABLE A-continued

|    |   |   |   |   |   |
|----|---|---|---|---|---|
| 25 |   | C | C | C | C |
| 26 |   | C | B | C | C |
| 27 |   |   | B | B | C |
| 28 |   |   | A |   |   |
| 29 |   |   | A |   |   |
| 30 |   |   | A |   |   |
| 31 |   |   | A |   |   |
| 32 |   |   | A |   |   |
| 33 |   |   | A |   |   |
| 34 |   |   | A |   |   |
| 35 |   |   | A |   |   |
| 36 |   |   | A |   |   |
| 37 |   |   | A |   |   |
| 38 |   |   | A |   |   |
| 39 |   |   | A |   |   |
| 40 |   |   | A |   |   |
| 41 |   |   | A |   |   |
| 42 |   |   | B |   |   |
| 43 |   |   | C |   |   |
| 44 |   |   | C |   |   |
| 45 |   |   | C |   |   |
| 46 |   |   |   | C |   |
| 47 |   |   |   | A |   |
| 48 |   | B |   |   | B |
| 49 |   | A |   |   | A |
| 50 |   | B |   |   | B |
| 51 |   | B |   |   | A |
| 52 |   | B |   |   | A |
| 53 |   | A |   |   | A |
| 54 |   | A |   |   | B |
| 55 |   | A |   |   | A |
| 56 |   | B |   |   | B |
| 57 |   | A |   |   | A |
| 58 |   | A |   |   | A |
| 59 |   | A |   |   | B |
| 60 | B | A |   |   | B |
| 61 | A | A | B | A | A |
| 62 |   | C |   |   | C |
| 63 |   | A |   |   | A |
| 64 |   | A |   |   | B |
| 65 |   | A |   |   | A |
| 66 | B | A | A | A | A |
| 67 |   | B | A |   | B |
| 68 | C | A | A |   | B |
| 69 |   | B | A |   | C |
| 70 |   | B | A |   | C |
| 71 |   | A | A |   | A |
| 72 |   | A |   |   | B |
| 73 |   |   |   |   |   |
| 74 |   |   |   |   |   |
| 75 |   | D |   |   |   |
| 76 |   | D |   |   |   |
| 77 |   | D |   |   |   |
| 78a |   |   |   |   |   |
| 78b |   | D |   |   |   |
| 79 |   | D |   |   |   |
| 80 | A | B |   |   |   |
| 81 |   | A |   |   | A |
| 82 |   | A |   |   | A |
| 83 |   | A |   |   | C |
| 84 | A | A | B | A | A |
| 85 |   | C |   |   | C |
| 86 | B | A |   |   | A |
| 87 |   | B |   |   | C |
| 88 |   | A |   |   | B |
| 89 | A | A | A | A | A |
| 90 | B |   |   |   |   |
| 91 | A | B | B | A | B |
| 92 |   | C |   |   | C |
| 93 |   | B | C | C | C |
| 94 | A | D |   |   |   |
| 95 | C |   |   |   |   |

TABLE A-continued

| | | | | | |
|---|---|---|---|---|---|
| 96 | C | E | | | |
| 97 | C | E | | | |
| 98 | C | | | | |
| 99 | A | | | | |
| 100 | B | | | | |
| 101 | B | D | | | |
| 102 | B | | | | |
| 103 | | | | | |
| | 1. Data obtained through protocol described in Example 105 | 2. Data obtained through protocol described in Example 106 | 3. Data obtained through protocol described in Example 107 | 4. Data obtained through protocol described in Example 108 | 5. Data obtained through protocol described in Example 109 |

| Example | IC50: I Org. Growth T. brucei rhodesiense STIB 900, 3 d [uM][6] | Inhibition of Organism Growth in Leishmania infantum MHOM/MA/BE/67, 5 d [uM][7] | IC50: I Org. amastigote Growth T. cruzi CL TdTomato, 3 d [uM][8] | SCYNEXIS IC50: I Org. Growth T. cruzi Tulahuen C2C4 Lac Z, 4 d [uM][9] | Swiss TPH T b rhodesiense IC50[10] |
|---|---|---|---|---|---|
| 1 | | | A | | |
| 2 | | | A | | |
| 3 | | | C | | |
| 4 | | | B | | |
| 5 | | | B | | |
| 6 | | | B | | |
| 7 | | | C | | |
| 8 | | | C | | |
| 9 | | | C | | |
| 10 | | | A | | |
| 11 | | | C | | |
| 12 | | | B | | |
| 13 | | | B | | |
| 14 | | | C | | |
| 15 | | | C | | |
| 16 | | | C | | |
| 17 | | | C | | |
| 18 | | | A | | |
| 19 | | | B | | |
| 20 | | | C | | |
| 21 | | | A | | |
| 22 | | | A | | |
| 23 | | | A | | |
| 24 | | | A | | |
| 25 | | | B | | |
| 26 | | | C | | |
| 27 | | | A | | |
| 28 | | | | | |
| 29 | | | | | |
| 30 | | | | | |
| 31 | | | | | |
| 32 | | | | | |
| 33 | | | | | |
| 34 | | | | | |
| 35 | | | | | |
| 36 | | | | | |
| 37 | | | | | |
| 38 | | | | | |
| 39 | | | | | |
| 40 | | | | | |
| 41 | | | | | |
| 42 | | | | B | |
| 43 | | | | | |
| 44 | | | | | |
| 45 | | | | | |
| 46 | | | | | |
| 47 | | | | | |
| 48 | | | | | |
| 49 | | | | A | |
| 50 | | | | A | |
| 51 | | | | B | |
| 52 | | | | C | |
| 53 | | | | | |
| 54 | | | | | |
| 55 | | | | | |
| 56 | | | | | |
| 57 | A | A | A | | A |
| 58 | A | B | | | A |

TABLE A-continued

| # | 6 | 7 | 8 | 9 | 10 |
|---|---|---|---|---|---|
| 59 | B | B | | | A |
| 60 | | A | | B | A |
| 61 | A | A | A | A | B |
| 62 | C | C | | | C |
| 63 | B | C | C | | B |
| 64 | B | A | | | A |
| 65 | A | A | A | | A |
| 66 | | | A | B | |
| 67 | B | C | | | B |
| 68 | A | A | | C | A |
| 69 | B | A | | | B |
| 70 | C | A | | | B |
| 71 | B | A | | | B |
| 72 | B | B | | | A |
| 73 | B | B | | | |
| 74 | B | A | | | |
| 75 | A | A | | | |
| 76 | B | B | | | |
| 77 | B | B | | | |
| 78a | C | B | | | |
| 78b | C | C | | | |
| 79 | C | C | | | |
| 80 | B | A | | | |
| 81 | B | B | C | | B |
| 82 | B | B | | | B |
| 83 | A | A | | | A |
| 84 | A | A | B | A | |
| 85 | C | C | | | C |
| 86 | | | B | C | |
| 87 | B | B | | | B |
| 88 | B | A | | | B |
| 89 | A | C | | A | A |
| 90 | | | | | |
| 91 | | | | | |
| 92 | C | C | | | C |
| 93 | C | C | C | | C |
| 94 | A | B | | | |
| 95 | | | | | |
| 96 | | | | | |
| 97 | | | | | |
| 98 | | | | | |
| 99 | B | A | | | |
| 100 | | | | | |
| 101 | | | | | |
| 102 | A | A | | | |
| 103 | C | B | | | A |
| | 6. Data obtained through protocol described in Example 110 | 7. Data obtained through protocol described in Example 111 | 8. Data obtained through protocol described in Example 112 | 9. Data obtained through protocol described in Example 113 | 10. Data obtained through protocol described in Example 114 |

What is claimed is:

1. A compound of formula I:

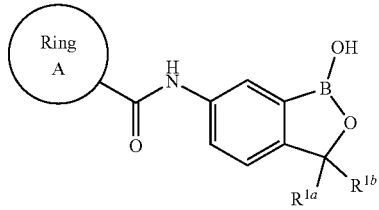

I or a pharmaceutically acceptable salt thereof, wherein:
$R^{1a}$ is hydrogen or $C_{1-6}$-aliphatic;
$R^{1b}$ is hydrogen or $C_{1-6}$-aliphatic;
wherein $R^{1a}$ and $R^{1b}$ are optionally taken together to form an optionally substituted 3- to 6-membered carbocyclic ring;

Ring A is triazolyl substituted with an $R^2$ group and an $R^3$ group;
$R^2$ is hydrogen or an optionally substituted group selected from $C_{1-6}$ aliphatic and 3-6 membered carbocyclyl;
$R^3$ is an optionally substituted group selected from phenyl, $C_{1-6}$ aliphatic, 3-8 membered carbocyclyl, and 5-6 membered heteroaryl containing 1-3 heteroatoms independently selected from nitrogen, oxygen, and sulfur.

2. The compound of claim 1, wherein Ring A is selected from:

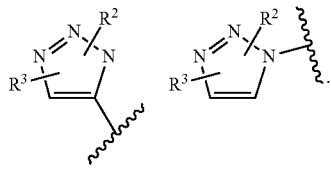

3. The compound of claim 1, wherein Ring A is selected from:

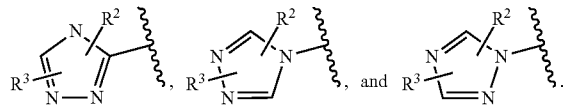

4. The compound of claim 1, wherein $R^{1a}$ is hydrogen or $C_{1-6}$-aliphatic and $R^{1b}$ is hydrogen or $C_{1-6}$-aliphatic.

5. The compound of claim 1, wherein $R^{1a}$ and $R^{1b}$ are taken together to form an optionally substituted 3- to 6-membered carbocyclic ring.

6. The compound of claim 4, wherein $R^2$ is hydrogen.

7. The compound of claim 4, wherein $R^2$ is an optionally substituted group selected from $C_{1-6}$ aliphatic and 3-6 membered carbocyclyl.

8. The compound of claim 6, wherein $R^3$ is optionally substituted phenyl.

9. The compound of claim 7, wherein $R^3$ is optionally substituted phenyl.

10. The compound of claim 6, wherein $R^3$ is optionally substituted 5-6 membered heteroaryl containing 1-3 heteroatoms independently selected from nitrogen, oxygen, and sulfur.

11. The compound of claim 10, wherein $R^3$ is optionally substituted pyridyl.

12. The compound of claim 7, wherein $R^3$ is optionally substituted 5-6 membered heteroaryl containing 1-3 heteroatoms independently selected from nitrogen, oxygen, and sulfur.

13. The compound of claim 12, wherein $R^3$ is optionally substituted pyridyl.

14. The compound of claim 1, wherein the compound is of formula II:

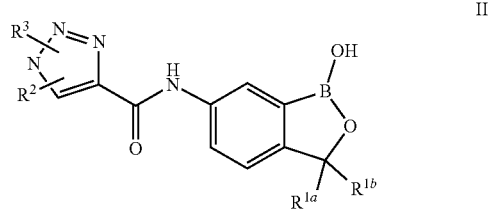

II or a pharmaceutically acceptable salt thereof.

15. A pharmaceutical composition comprising a compound of claim 1, or a pharmaceutically acceptable salt thereof, and at least one pharmaceutically acceptable excipient.

16. A method of treating cutaneous leishmaniasis comprising administering to a subject a compound of claim 1, or a pharmaceutically acceptable salt thereof.

17. A method of treating visceral leishmaniasis comprising administering to a subject a compound of claim 1, or a pharmaceutically acceptable salt thereof.

18. A pharmaceutical composition comprising a compound of claim 14, or a pharmaceutically acceptable salt thereof, and at least one pharmaceutically acceptable excipient.

19. A method of treating cutaneous leishmaniasis comprising administering to a subject a compound of claim 14, or a pharmaceutically acceptable salt thereof.

20. A method of treating visceral leishmaniasis comprising administering to a subject a compound of claim 14, or a pharmaceutically acceptable salt thereof.

* * * * *